US012630559B2

(12) United States Patent
Han et al.

(10) Patent No.: US 12,630,559 B2
(45) Date of Patent: May 19, 2026

(54) SPIROCYCLIC-SUBSTITUTED 6,7-DIHYDRO-PYRANO[2,3- D]PYRIMIDINE INHIBITORS OF KRAS G12C MUTANT

(71) Applicant: Merck Sharp & Dohme LLC, Rahway, NJ (US)

(72) Inventors: Yongxin Han, Needham, MA (US); Elisabeth Hennessy, Weston, MA (US); Andrew J. Hoover, Framingham, MA (US); Jesus Moreno, Dorchester Center, MA (US); David L. Sloman, Newton, MA (US); Uma Swaminathan, Auburndale, MA (US); Yingchun Ye, Belmont, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 409 days.

(21) Appl. No.: 18/038,364

(22) PCT Filed: Nov. 23, 2021

(86) PCT No.: PCT/US2021/060608
§ 371 (c)(1),
(2) Date: May 23, 2023

(87) PCT Pub. No.: WO2022/109487
PCT Pub. Date: May 27, 2022

(65) Prior Publication Data

US 2024/0124478 A1 Apr. 18, 2024

Related U.S. Application Data

(60) Provisional application No. 63/117,171, filed on Nov. 23, 2020.

(51) Int. Cl.
*C07D 491/107* (2006.01)
*A61K 45/06* (2006.01)
*C07D 491/20* (2006.01)

(52) U.S. Cl.
CPC .......... *C07D 491/107* (2013.01); *A61K 45/06* (2013.01); *C07D 491/20* (2013.01)

(58) Field of Classification Search
None
See application file for complete search history.

(56) References Cited

U.S. PATENT DOCUMENTS 4,034,075 A 7/1977 Bays et al.
9,840,516 B2 12/2017 Li et al.
10,125,134 B2 11/2018 Blake et al.
10,144,724 B2 12/2018 Li et al.
10,556,906 B2 2/2020 Kuramoto et al.
10,662,204 B2 5/2020 Planken et al.
10,988,485 B2 4/2021 Minatti et al.
11,045,484 B2 6/2021 Wurz et al.
(Continued)

FOREIGN PATENT DOCUMENTS

CN 104011054 A 8/2014
CN 107556289 A 1/2018
(Continued)

OTHER PUBLICATIONS

D.S. Hong, et al., “KRASG12C Inhibition with Sotorasib in Advanced Solid Tumors”, The New England Journal of Medicine, vol. 383 No. 13 pp. 1207-1217 (2020).
(Continued)

*Primary Examiner* — Jeffrey S Lundgren
*Assistant Examiner* — Anthony Joseph Seitz
(74) *Attorney, Agent, or Firm* — Venable LLP

(57) ABSTRACT

The disclosure provides compounds of Formula (I)

(I)

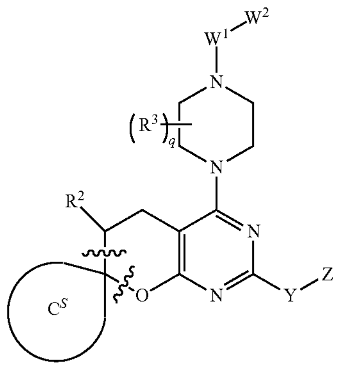

or a pharmaceutically acceptable salt thereof, wherein $W^1$, $W^2$, Y, Z, $C^S$, $R^2$, and $R^3$ are as described herein. The compounds or their pharmaceutically acceptable salts can inhibit the G12C mutant of Kirsten rat sarcoma (KRAS) protein and are expected to have utility as therapeutic agents, for example, for treating cancer. The disclosure also provides pharmaceutical compositions which comprise compounds of Formula (I) or pharmaceutically acceptable salts thereof. The disclosure also relates to methods for use of the compounds or their pharmaceutically acceptable salts in the therapy and prophylaxis of cancer and for preparing pharmaceuticals for this purpose.

19 Claims, No Drawings

Specification includes a Sequence Listing.

(56) References Cited

U.S. PATENT DOCUMENTS

| | | | |
|---|---|---|---|
| 11,090,304 | B2 | 8/2021 | Allen et al. |
| 11,096,939 | B2 | 8/2021 | Booker et al. |
| 11,299,491 | B2 | 4/2022 | Parsons et al. |
| 11,453,683 | B1 | 9/2022 | Wang et al. |
| 11,459,327 | B1 | 10/2022 | Lv et al. |
| 11,530,218 | B2 | 12/2022 | Zhao et al. |
| 11,697,657 | B2 | 7/2023 | Bharathan et al. |
| 11,932,633 | B2 | 3/2024 | Marx et al. |
| 12,208,099 | B2 | 1/2025 | Aranda et al. |
| 2006/0135532 | A1 | 6/2006 | Bryant et al. |
| 2010/0331305 | A1 | 12/2010 | Bergeron et al. |
| 2014/0275070 | A1 | 9/2014 | Grembecka et al. |
| 2014/0288045 | A1 | 9/2014 | Ren et al. |
| 2014/0371203 | A1 | 12/2014 | Madge et al. |
| 2015/0176010 | A1 | 6/2015 | Wersinger |
| 2015/0239900 | A1 | 8/2015 | Li et al. |
| 2015/0246934 | A1 | 9/2015 | Bensen et al. |
| 2016/0046647 | A1 | 2/2016 | Grembecka et al. |
| 2016/0108019 | A1 | 4/2016 | Li et al. |
| 2016/0137665 | A1 | 5/2016 | Grembecka et al. |
| 2016/0152634 | A1 | 6/2016 | Madge et al. |
| 2016/0159738 | A1 | 6/2016 | Ren et al. |
| 2016/0297774 | A1 | 10/2016 | Li et al. |
| 2016/0318866 | A1 | 11/2016 | Becker-Pelster et al. |
| 2017/0131278 | A1 | 5/2017 | Patricelli et al. |
| 2017/0197945 | A1 | 7/2017 | Li et al. |
| 2017/0253611 | A1 | 9/2017 | Grembecka et al. |
| 2018/0072723 | A1 | 3/2018 | Blake et al. |
| 2018/0118757 | A1 | 5/2018 | Li et al. |
| 2018/0127396 | A1 | 5/2018 | Li et al. |
| 2018/0141927 | A1 | 5/2018 | Li et al. |
| 2018/0162812 | A1 | 6/2018 | Ren et al. |
| 2018/0177767 | A1 | 6/2018 | Lanman et al. |
| 2018/0334454 | A1 | 11/2018 | Anman et al. |
| 2019/0062313 | A1 | 2/2019 | Li et al. |
| 2019/0062330 | A1 | 2/2019 | Blake et al. |
| 2019/0127336 | A1 | 5/2019 | Li et al. |
| 2019/0144444 | A1 | 5/2019 | Blake et al. |
| 2019/0233440 | A1 | 8/2019 | Planken et al. |
| 2019/0248767 | A1 | 8/2019 | Planken et al. |
| 2019/0270743 | A1 | 9/2019 | Marx et al. |
| 2019/0276432 | A1 | 9/2019 | Beaumont et al. |
| 2019/0284144 | A1 | 9/2019 | Li et al. |
| 2019/0292182 | A1 | 9/2019 | Kuramoto et al. |
| 2019/0343838 | A1 | 11/2019 | Allen et al. |
| 2019/0374542 | A1 | 12/2019 | Allen et al. |
| 2019/0375749 | A1 | 12/2019 | Chen et al. |
| 2020/0055845 | A1 | 2/2020 | Anman et al. |
| 2020/0069657 | A1 | 3/2020 | Anman et al. |
| 2020/0115363 | A1 | 4/2020 | Li et al. |
| 2020/0115375 | A1 | 4/2020 | Barda et al. |
| 2020/0140437 | A1 | 5/2020 | Kuramoto et al. |
| 2020/0165231 | A1 | 5/2020 | Shin et al. |
| 2020/0181118 | A1 | 6/2020 | Malhotra et al. |
| 2020/0237771 | A1 | 7/2020 | Hallur et al. |
| 2020/0262837 | A1 | 8/2020 | Marx et al. |
| 2020/0289503 | A1 | 9/2020 | Huang |
| 2020/0331911 | A1 | 10/2020 | Marx et al. |
| 2021/0009577 | A1 | 1/2021 | Lanman et al. |
| 2021/0024501 | A1 | 1/2021 | Li et al. |
| 2021/0040089 | A1 | 2/2021 | Gao et al. |
| 2021/0047297 | A1 | 2/2021 | Schulze et al. |
| 2021/0122764 | A1 | 4/2021 | Bharathan et al. |
| 2021/0395234 | A1 | 12/2021 | Sakamoto et al. |
| 2022/0064141 | A1 | 3/2022 | Fang et al. |
| 2022/0112204 | A1 | 4/2022 | Fan et al. |
| 2022/0298174 | A1 | 9/2022 | Guo et al. |
| 2022/0315597 | A1 | 10/2022 | Su et al. |
| 2022/0315598 | A1 | 10/2022 | Xu et al. |
| 2022/0370416 | A1 | 11/2022 | Chu et al. |
| 2022/0389029 | A1 | 12/2022 | Guo et al. |
| 2022/0402916 | A1 | 12/2022 | Hoover et al. |
| 2023/0023023 | A1 | 1/2023 | Shibata et al. |
| 2023/0049402 | A1 | 2/2023 | Sakamoto et al. |
| 2023/0174518 | A1 | 6/2023 | Kawai |
| 2023/0181536 | A1 | 6/2023 | Abe et al. |
| 2023/0348495 | A1 | 11/2023 | Kawai et al. |
| 2023/0416266 | A1 | 12/2023 | Han et al. |
| 2024/0043448 | A1 | 2/2024 | Bharathan et al. |
| 2024/0083913 | A1 | 3/2024 | Bharathan et al. |
| 2024/0174691 | A1 | 5/2024 | Jiang et al. |
| 2024/0239788 | A1 | 7/2024 | Sloman et al. |
| 2024/0246968 | A1 | 7/2024 | Shibata et al. |
| 2024/0262842 | A1 | 8/2024 | Shibata et al. |
| 2024/0317759 | A1 | 9/2024 | Kobayakawa et al. |
| 2024/0376123 | A1 | 11/2024 | Zhou et al. |
| 2024/0417408 | A1 * | 12/2024 | Shibata .................. A61P 35/00 |
| 2025/0136615 | A1 | 5/2025 | Kawamura et al. |

FOREIGN PATENT DOCUMENTS

| | | | |
|---|---|---|---|
| CN | 109843856 | A | 6/2019 |
| CN | 112390788 | A1 | 2/2021 |
| CN | 112430234 | A | 3/2021 |
| CN | 114615981 | A | 6/2022 |
| EP | 3871673 | A1 | 9/2021 |
| EP | 4053120 | A1 | 9/2022 |
| EP | 4397664 | A1 | 10/2024 |
| JP | 2016-519072 | A | 6/2016 |
| JP | 2016-532656 | A | 10/2016 |
| JP | 2017-528498 | A | 9/2017 |
| WO | 03/037898 | A1 | 5/2003 |
| WO | 2005/019177 | A1 | 3/2005 |
| WO | 2009/114575 | A1 | 9/2009 |
| WO | 2010/064705 | A1 | 6/2010 |
| WO | 2013/072694 | A1 | 5/2013 |
| WO | 2014/043272 | A1 | 3/2014 |
| WO | 2014/143659 | A1 | 9/2014 |
| WO | 2014/152588 | A1 | 9/2014 |
| WO | 2014/164543 | A1 | 10/2014 |
| WO | 2015/054572 | A1 | 4/2015 |
| WO | 2015/091415 | A1 | 6/2015 |
| WO | 2015/131005 | A1 | 9/2015 |
| WO | 2016/029454 | A1 | 3/2016 |
| WO | 2016/044772 | A1 | 3/2016 |
| WO | 2016/049524 | A1 | 3/2016 |
| WO | 2016/049565 | A1 | 3/2016 |
| WO | 2016/049568 | A1 | 3/2016 |
| WO | 2016/164675 | A1 | 10/2016 |
| WO | 2016/168540 | A1 | 10/2016 |
| WO | 2017/015562 | A1 | 1/2017 |
| WO | 2017/058728 | A1 | 4/2017 |
| WO | 2017/058768 | A1 | 4/2017 |
| WO | 2017/058792 | A1 | 4/2017 |
| WO | 2017/058805 | A1 | 4/2017 |
| WO | 2017/058807 | A1 | 4/2017 |
| WO | 2017/058902 | A1 | 4/2017 |
| WO | 2017/058915 | A1 | 4/2017 |
| WO | 2017/070256 | A2 | 4/2017 |
| WO | 2017/087528 | A1 | 5/2017 |
| WO | 2017/100546 | A1 | 6/2017 |
| WO | 2017/172979 | A1 | 10/2017 |
| WO | 2017/201161 | A1 | 11/2017 |
| WO | 2018/022897 | A1 | 2/2018 |
| WO | 2018/064510 | A1 | 4/2018 |
| WO | 2018/068017 | A1 | 4/2018 |
| WO | 2018/119183 | A2 | 6/2018 |
| WO | 2018/140512 | A1 | 8/2018 |
| WO | 2018/140513 | A1 | 8/2018 |
| WO | 2018/140514 | A1 | 8/2018 |
| WO | 2018/140598 | A1 | 8/2018 |
| WO | 2018/140599 | A1 | 8/2018 |
| WO | 2018/140600 | A1 | 8/2018 |
| WO | 2018/143315 | A1 | 8/2018 |
| WO | 2018/206539 | A1 | 11/2018 |
| WO | 2018/217651 | A1 | 11/2018 |
| WO | 2018/218069 | A1 | 11/2018 |
| WO | 2018/218070 | A2 | 11/2018 |
| WO | 2018/218071 | A1 | 11/2018 |
| WO | 2019/051291 | A1 | 3/2019 |
| WO | 2019/058132 | A1 | 3/2019 |
| WO | 2019/058393 | A1 | 3/2019 |
| WO | 2019/077631 | A1 | 4/2019 |
| WO | 2019/099524 | A1 | 5/2019 |

(56) References Cited

FOREIGN PATENT DOCUMENTS

| | | | |
|---|---|---|---|
| WO | 2019/099703 | A1 | 5/2019 |
| WO | 2019/110751 | A1 | 6/2019 |
| WO | 2019/155399 | A1 | 8/2019 |
| WO | 2019/167000 | A1 | 9/2019 |
| WO | 2019/185525 | A1 | 10/2019 |
| WO | 2019/215203 | A1 | 11/2019 |
| WO | 2019213526 | A1 | 11/2019 |
| WO | 2019217307 | A1 | 11/2019 |
| WO | 2019217691 | A1 | 11/2019 |
| WO | 2019232419 | A1 | 12/2019 |
| WO | 2020/035031 | A1 | 2/2020 |
| WO | 2020/041331 | A1 | 2/2020 |
| WO | 2020/050890 | A2 | 3/2020 |
| WO | 2020047192 | A1 | 3/2020 |
| WO | 2020055755 | A1 | 3/2020 |
| WO | 2020055756 | A1 | 3/2020 |
| WO | 2020055758 | A1 | 3/2020 |
| WO | 2020055760 | A1 | 3/2020 |
| WO | 2020055761 | A1 | 3/2020 |
| WO | 2020/085493 | A1 | 4/2020 |
| WO | 2020/097537 | A2 | 5/2020 |
| WO | 2020/101736 | A1 | 5/2020 |
| WO | 2020102730 | A1 | 5/2020 |
| WO | 2020/113071 | A1 | 6/2020 |
| WO | 2020118066 | A1 | 6/2020 |
| WO | 2020/146613 | A1 | 7/2020 |
| WO | 2020/156285 | A1 | 8/2020 |
| WO | 2020/177629 | A1 | 9/2020 |
| WO | 2020/178282 | A1 | 9/2020 |
| WO | 2020/221239 | A1 | 11/2020 |
| WO | 2020/233592 | A1 | 11/2020 |
| WO | 2020/234103 | A1 | 11/2020 |
| WO | 2020/236940 | A1 | 11/2020 |
| WO | 2020/238791 | A1 | 12/2020 |
| WO | 2020/239077 | A1 | 12/2020 |
| WO | 2020/239123 | A1 | 12/2020 |
| WO | 2020/244637 | A1 | 12/2020 |
| WO | 2020/259432 | A1 | 12/2020 |
| WO | 2020/259513 | A1 | 12/2020 |
| WO | 2020/259573 | A1 | 12/2020 |
| WO | 2021/000885 | A1 | 1/2021 |
| WO | 2021/023154 | A1 | 2/2021 |
| WO | 2021/027911 | A1 | 2/2021 |
| WO | 2021/027943 | A1 | 2/2021 |
| WO | 2021/031952 | A1 | 2/2021 |
| WO | 2021/037018 | A1 | 3/2021 |
| WO | 2021/041671 | A1 | 3/2021 |
| WO | 2021/043322 | A1 | 3/2021 |
| WO | 2021/052499 | A1 | 3/2021 |
| WO | 2021/055728 | A1 | 3/2021 |
| WO | 2021/057832 | A1 | 4/2021 |
| WO | 2021/058018 | A1 | 4/2021 |
| WO | 2021/063346 | A1 | 4/2021 |
| WO | 2021/078312 | A1 | 4/2021 |
| WO | 2021/081212 | A1 | 4/2021 |
| WO | 2021/083167 | A1 | 5/2021 |
| WO | 2021/084765 | A1 | 5/2021 |
| WO | 2021/085653 | A1 | 5/2021 |
| WO | 2021/086833 | A1 | 5/2021 |
| WO | 2021/088458 | A1 | 5/2021 |
| WO | 2021/093758 | A1 | 5/2021 |
| WO | 2021/098859 | A1 | 5/2021 |
| WO | 2021/104431 | A1 | 6/2021 |
| WO | 2021/106230 | A1 | 6/2021 |
| WO | 2021/106231 | A1 | 6/2021 |
| WO | 2021/107160 | A1 | 6/2021 |
| WO | 2021/109737 | A1 | 6/2021 |
| WO | 2021/113595 | A1 | 6/2021 |
| WO | 2021/118877 | A1 | 6/2021 |
| WO | 2021/121330 | A1 | 6/2021 |
| WO | 2021/121367 | A1 | 6/2021 |
| WO | 2021/121371 | A1 | 6/2021 |
| WO | 2021/124222 | A1 | 6/2021 |
| WO | 2021/127404 | A1 | 6/2021 |
| WO | 2021/129824 | A1 | 7/2021 |
| WO | 2021/147965 | A1 | 7/2021 |
| WO | 2021/147967 | A1 | 7/2021 |
| WO | 2021142252 | A1 | 7/2021 |
| WO | 2021150613 | A1 | 7/2021 |
| WO | 2021/215544 | A1 | 10/2021 |
| WO | 2021/215545 | A1 | 10/2021 |
| WO | 2021211864 | A1 | 10/2021 |
| WO | 2021/219072 | A1 | 11/2021 |
| WO | 2022002102 | A1 | 1/2022 |
| WO | 2022015375 | A1 | 1/2022 |
| WO | 2022031678 | A1 | 2/2022 |
| WO | 2022/066646 | A1 | 3/2022 |
| WO | 2022042630 | A1 | 3/2022 |
| WO | 2022047260 | A1 | 3/2022 |
| WO | 2022061251 | A1 | 3/2022 |
| WO | 2022068921 | A1 | 4/2022 |
| WO | 2022083569 | A1 | 4/2022 |
| WO | 2022087371 | A1 | 4/2022 |
| WO | 2022087375 | A1 | 4/2022 |
| WO | 2022/105857 | A1 | 5/2022 |
| WO | 2022/109485 | A1 | 5/2022 |
| WO | 2022/132200 | A1 | 6/2022 |
| WO | 2022/133038 | A1 | 6/2022 |
| WO | 2022/148421 | A1 | 7/2022 |
| WO | 2022/148422 | A1 | 7/2022 |
| WO | 2022/173870 | A1 | 8/2022 |
| WO | 2022/177917 | A2 | 8/2022 |
| WO | 2022187688 | A1 | 9/2022 |
| WO | 2022/221739 | A1 | 10/2022 |
| WO | 2022/228568 | A1 | 11/2022 |
| WO | 2022/232318 | A1 | 11/2022 |
| WO | 2022/232320 | A1 | 11/2022 |
| WO | 2022/247760 | A1 | 12/2022 |
| WO | 2022/250170 | A1 | 12/2022 |
| WO | 2022/251576 | A1 | 12/2022 |
| WO | 2022/256459 | A1 | 12/2022 |
| WO | 2022/266206 | A1 | 12/2022 |
| WO | 2022248885 | A2 | 12/2022 |
| WO | 2022258974 | A1 | 12/2022 |
| WO | 2022261210 | A1 | 12/2022 |
| WO | 2022262686 | A1 | 12/2022 |
| WO | 2022266069 | A1 | 12/2022 |
| WO | 2022271658 | A1 | 12/2022 |
| WO | 2023018699 | A1 | 2/2023 |
| WO | 2023018809 | A1 | 2/2023 |
| WO | 2023018812 | A1 | 2/2023 |
| WO | 2023020518 | A1 | 2/2023 |
| WO | 2023020519 | A1 | 2/2023 |
| WO | 2023020521 | A1 | 2/2023 |
| WO | 2023020523 | A1 | 2/2023 |
| WO | 2023/046135 | A1 | 3/2023 |
| WO | 2023034290 | A1 | 3/2023 |
| WO | 2023049697 | A1 | 3/2023 |
| WO | 2023/059596 | A1 | 4/2023 |
| WO | 2023/059597 | A1 | 4/2023 |
| WO | 2023/059598 | A1 | 4/2023 |
| WO | 2023056421 | A1 | 4/2023 |
| WO | 2023056951 | A1 | 4/2023 |
| WO | 2023060253 | A1 | 4/2023 |
| WO | 2023061294 | A1 | 4/2023 |
| WO | 2023061463 | A1 | 4/2023 |
| WO | 2023064857 | A1 | 4/2023 |
| WO | 2023072188 | A1 | 5/2023 |
| WO | 2023/097227 | A1 | 6/2023 |
| WO | 2023/103523 | A1 | 6/2023 |
| WO | 2023098425 | A1 | 6/2023 |
| WO | 2023098426 | A1 | 6/2023 |
| WO | 2023098832 | A1 | 6/2023 |
| WO | 2023099592 | A1 | 6/2023 |
| WO | 2023099608 | A1 | 6/2023 |
| WO | 2023099612 | A1 | 6/2023 |
| WO | 2023099620 | A1 | 6/2023 |
| WO | 2023099623 | A1 | 6/2023 |
| WO | 2023099624 | A1 | 6/2023 |
| WO | 2023101928 | A1 | 6/2023 |
| WO | 2023103906 | A1 | 6/2023 |
| WO | 2023104018 | A1 | 6/2023 |
| WO | 2023105491 | A1 | 6/2023 |
| WO | 2023114733 | A1 | 6/2023 |

(56) References Cited

FOREIGN PATENT DOCUMENTS

| | | | |
|---|---|---|---|
| WO | 2023117681 | A1 | 6/2023 |
| WO | 2023122154 | A1 | 6/2023 |
| WO | 2023125627 | A1 | 7/2023 |
| WO | 2023125989 | A1 | 7/2023 |
| WO | 2023133183 | A | 7/2023 |
| WO | 2023/150284 | A2 | 8/2023 |
| WO | 2023/159087 | A1 | 8/2023 |
| WO | 2023/173017 | A1 | 9/2023 |
| WO | 2023/179703 | A1 | 9/2023 |
| WO | 2023/193085 | A1 | 10/2023 |
| WO | 2023/197984 | A1 | 10/2023 |
| WO | 2023/244615 | A1 | 12/2023 |
| WO | 2024/009191 | A1 | 1/2024 |
| WO | 2024/012519 | A1 | 1/2024 |
| WO | 2024/015262 | A1 | 1/2024 |
| WO | 2024/032704 | A1 | 2/2024 |
| WO | 2024/041573 | A1 | 2/2024 |
| WO | 2024/044667 | A2 | 2/2024 |
| WO | 2024031088 | A1 | 2/2024 |
| WO | 2024/063578 | A1 | 3/2024 |
| WO | 2024/083168 | A1 | 4/2024 |
| WO | 2024/088069 | A1 | 5/2024 |
| WO | 2024/103010 | A1 | 5/2024 |
| WO | 2024/120433 | A1 | 6/2024 |
| WO | 2024/209339 | A1 | 10/2024 |
| WO | 2024/213979 | A1 | 10/2024 |
| WO | 2024/233776 | A1 | 11/2024 |
| WO | 2024/238343 | A1 | 11/2024 |
| WO | 2025/019819 | A1 | 1/2025 |
| WO | 2025/019823 | A1 | 1/2025 |
| WO | 2025/085748 | A1 | 4/2025 |
| WO | 2025/230961 | A1 | 11/2025 |
| WO | 2025/235740 | A1 | 11/2025 |
| WO | 2025/240740 | A1 | 11/2025 |
| WO | 2025/240742 | A1 | 11/2025 |

OTHER PUBLICATIONS

D. Gentile, et al., "Ras Binder Induces a Modified Switch-II Pocket in GTP and GDP States", Cell Chemical Biology, 24, pp. 1455-1466 (2017).
D. Kessler, et al., "Drugging an undruggable pocket on KRAS", Proceedings of the National Academy of Sciences (PNAS), vol. 116, No. 32, pp. 15823-15829 (2019).
Y. Mao, et al., "Design, synthesis and biological evaluation of novel pyrimidine, 3-cyanopyridine and m-amino-N-phenylbenzamide based monocyclic EGFR tyrosine kinase inhibitors", Bioorganic & Medicinal Chemistry, 21, pp. 3090-3104 (2013).
PubChem CID 10121096, PubChem release Jun. 18, 2019, modify date Nov. 21, 2020, retrieved on Feb. 10, 2021 (9 pages).
G. Palfy, et al., "1H, 15N backbone assignment and comparative analysis of the wild type and G12C, G12D, G12V mutants of K-Ras bound to GDP at physiological pH", Biomolecular NMR Assignment, vol. 14, No. 1, pp. 1-7 (2019).
M.R. Janes, et al., "Targeting KRAS Mutant Cancers with a Covalent G12C-Specific Inhibitor", Cell, 172, pp. 578-589 (2018).
M.P. Patricelli, et al., "Selective Inhibition of Oncogenic KRAS Output with Small Molecules Targeting the Inactive State", Cancer Discovery, 6(3), pp. 316-329 (2016).
H. Chuang, et al., "Pharmacological strategies to target oncogenic KRAS signaling in pancreatic cancer", Pharmacological Research, 117, pp. 370-376 (2017).
Lopez-Tapia, F., et al., "Linker Variation and Structure-Activity Relationship Analyses of Carboxylic Acid-based Small Molecule STAT3 Inhibitors", ACS Med. Chem. Lett. 2018, 9, 250-255.
R.B. Kargbo, "Small Molecule Inhibitors of KRAS G12C Mutant", Acs Med. Chem. Lett., vol. 12, pp. 1210-1211 (2021).
International Search Report and Written Opinion in corresponding international application No. PCT/US21/60608 dated Jan. 22, 2022 (8 pages).
PubChem SID 469710826, available Jul. 28, 2022.
J.G. Kettle, et al., "Structure-Based Design and Pharmacokinetic Optimization of Covalent Allosteric Inhibitors of the Mutant GTPase KRAS G12C", J. Med. Chem., vol. 63, pp. 4468-4483 (2020).
Q. Zheng, et al., "Drugging the Next Undruggable KRAS Allele-Gly12Asp", J. Med. Chem, vol. 65, pp. 3119-3122 (2022).
Examination Report in co-pending European Patent Application No. 21895831.2 dated Sep. 17, 2024 (7 pages).
El-Meligie, Salwa E. M. et al., "New synthetic approaches to thieno[3,2-d]pyrimidine and thieno[3, 4-b]pyridine derivatives", Chemical Papers, vol. 74, pp. 2501-2514 (2020).
El-Kashef, H et al., "Pyridine-Based Heterocycles. Synthesis of New Pyrido[4', 3':4,5]thieno[2,3-d]pyrimidines and Related Heterocycles", Molecules, vol. 15, pp. 2651-2666 (2010).
Szanto, Get al., "New P2X3 receptor antagonists. Part 2: Identification and SAR of quinazolinones," Bioorganic and Medicinal Chemistry Letters, vol. 26, No. 16, pp. 3905-3912, abstract (2016).
Sanad, SMH et al., "Efficient Synthesis and Characterization of Novel Pyrido[3',2':4,5]thieno[3,2-d]pyrimidines and Their Fused [1,2,4]triazole Derivatives", Journal of Heterocyclic Chemistry, vol. 55, No. 12, pp. 2823-2833, abstract (2018).
Showalter, H.D. Hollis et al., "Tyrosine Kinase Inhibitors. 16. 6,5,6-Tricyclic Benzothieno[3,2-d]pyrimidines and Pyrimido[S,4-b]- and -[4,5-b]indoles as Potent Inhibitors of the Epidermal Growth Factor Receptor Tyrosine Kinase", Journal of Medicinal Chemistry, vol. 42, No. 26, pp. 5464-5474, abstract (1999).
Wang, H. et al., "Annual review of KRAS inhibitors in 2022", European J. of Medicinal Chem., 249, p. 1-14 (2023).
Sanad, SMH et al., "New thieno[2,3-b ]pyridine-fused pyrimidin-4(3H)-ones as potentialinhibitors: Synthesis, SAR, in vitro and in silica study", Journal of Molecular Structure, vol. 1282, (2023).
Hamarsheh S., et al., "Immune modulatory effects of oncogenic KRAS in cancer", Nature Commun., 11:5439 (2020).

* cited by examiner

SPIROCYCLIC-SUBSTITUTED 6,7-DIHYDRO-PYRANO[2,3- D]PYRIMIDINE INHIBITORS OF KRAS G12C MUTANT

CROSS REFERENCE TO RELATED APPLICATIONS

This application is a national-stage entry under 35 U.S.C. § 371 of International Application No. PCT/US2021/060608 filed on Nov. 23, 2021, and claims the benefit of priority of provisional Appl. No. 63/117,171, filed Nov. 23, 2020.

FIELD OF THE INVENTION

The present disclosure relates to certain spirocyclic-substituted 6,7-dihydro-5H-pyrano[2,3-d]pyrimidines and pharmaceutically acceptable salts thereof that inhibit the G12C mutant of Kirsten rat sarcoma (KRAS) protein and are expected to have utility as therapeutic agents, for example, for treatment of cancer. The present application also relates to pharmaceutical compositions containing such compounds as well as methods of using the compounds for treating cancer.

BACKGROUND OF THE INVENTION

RAS proteins are membrane-associated guanine nucleotide-binding proteins which function as molecular switches. RAS proteins function as components of signalling pathways transmitting signals from cell-surface receptors to regulate cellular proliferation, survival and differentiation. RAS proteins cycle between an inactive GDP-bound state and an active GTP-bound state.

The most notable members of the RAS subfamily are HRAS, KRAS and NRAS, mainly being implicated in many types of cancer. However, there are many other members including DIRAS1; DIRAS2; DIRAS3; ERAS; GEM; MRAS; KIRAS1; KIRAS2; NRAS; RALA; RALB; RAPIA; RAPIB; RAP2A; RAP2B; RAP2C; RASD1; RASD2; RASL10A; RASL10B; RASL11A; RASL11B; RASL12; REM1; REM2; RERG; RERGL; RRAD; RRAS and RRAS2.

Mutations in any one of the three main isoforms of RAS (HRAS, NRAS, or KRAS) genes are among the most common events in human tumorigenesis. KRAS mutations are detected in 25-30% of tumors. By comparison, the rates of oncogenic mutation occurring in the NRAS and HRAS family members are much lower (8% and 3% respectively).

Exchange of a glycine for a cysteine at residue 12 of RAS (the G12C mutation) results from a mutation commonly found in RAS genes. Large-scale cancer sequencing studies indicate that the G12C mutation appeared most frequently in lung, colorectal and pancreatic cancers. Histological analysis of seven cancer types indicated non-small cell lung cancer contributed the most, 70-75%, to cancer cases having the KRAS G12C mutation. See Lindsay, C. R., et al., *Br J Cancer* 121, 197-198 (2019).

Accordingly, while progress has been made in this field, there remains a need in the art for improved compounds and methods for treatment of cancer, for example, by inhibition of a mutant KRAS, HRAS or NRAS protein (e.g., KRAS G12C). Embodiments of the present disclosure fulfill this need and provide further related advantages.

SUMMARY OF THE DISCLOSURE

The present disclosure provides 6,7-dihydro-5H-pyrano[2,3-d]pyrimidines which modulate mutant KRAS, HRAS, and/or NRAS proteins and may be valuable pharmaceutically active compounds for the treatment of cancer. In some embodiments the disclosed compounds selectively inhibit the KRAS (G12C) protein. The compounds of Formula (I)

(I)

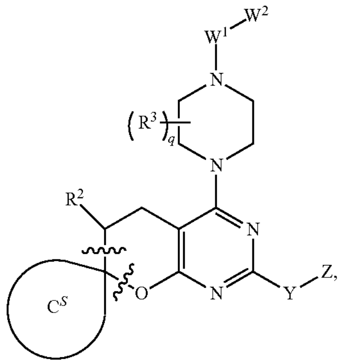

and their pharmaceutically acceptable salts, can modulate the activity of KRAS, HRAS and/or NRAS activity and thereby affect the signaling pathway which regulates cell growth, differentiation, and proliferation associated with oncological disorders. In certain embodiments, the compounds of Formula (I) can inhibit the KRAS (G12C) protein. The disclosure furthermore provides processes for preparing compounds of Formula (I), methods for using such compounds to treat oncological disorders, and pharmaceutical compositions which comprise compounds of Formula (I).

DETAILED DESCRIPTION OF THE INVENTION

Compounds of the Disclosure

In embodiment no. 1, the present disclosure provides a compound having structural Formula (I) as shown above wherein:

the substructure is

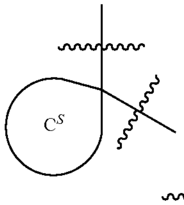

is

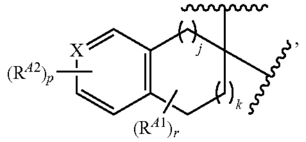

,

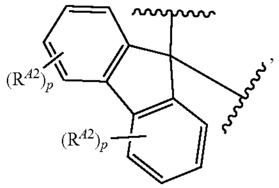

, or

-continued

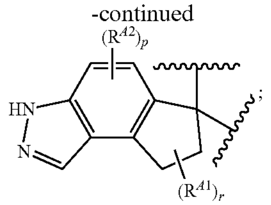

X is C(H) or N;

$R^{A1}$ is fluoro, $C_1$-$C_3$ alkyl, or $C_1$-$C_3$ fluoroalkyl;

$R^{A2}$ is halo, $C_1$-$C_3$ alkyl, $C_1$-$C_3$ fluoroalkyl, $C_1$-$C_3$ alkoxy, hydroxy or cyano;

the subscript j is 0 or 1;

the subscript k is 0, 1 or 2;

the subscript r is 0, 1, 2, or 3;

the subscript p is 0, 1, 2, 3, or 4;

$R^2$ is H, $C_1$-$C_3$ alkyl, or fluoro;

each $R^3$ is independently:

(a) $C_1$-$C_4$ alkyl, $C_1$-$C_4$ cyanoalkyl, $C_1$-$C_4$ fluoroalkyl, $C_1$-$C_4$ hydroxyalkyl, $C_1$-$C_4$ alkylphenyl, oxo, or carboxy;

(b) or, alternatively, two $R^3$ substituents, together with the carbon atoms to which they are attached, can form a 3- to 6-membered bicyclo- or spirocyclic ring system with the illustrated piperazine ring;

the subscript q is 0, 1, 2, or 3;

$W^1$ is —C(O)— or —$S(O)_2$—

$W^2$ is a group of the formula:

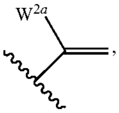, 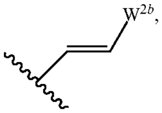, 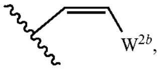,

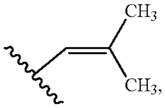 or 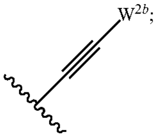;

wherein $W^{2a}$ is H, $CH_3$, F, cyano, $CH_2OH$, $CH_2CH_2OH$, or $CH_2Br$;

$W^{2b}$ is $CH_3$, $CH_2NH_2$, $CH_2N(H)CH_3$, $CH_2N(CH_3)_2$, $CH_2$—NH-cyclopropyl,

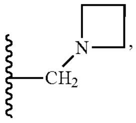, 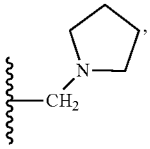, or 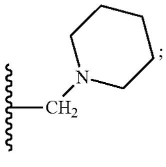;

Y is —$O(C(R^y)_2)_m$—, —C(O)—N(H)—$(C(R^y)_2)_m$—, or absent;

each $R^y$ is independently H or $C_1$-$C_3$ alkyl, or alternatively two $R^y$ together with the carbon atom to which they are attached form a cyclopropyl, cyclobutyl, cyclopentyl or cyclohexyl ring;

the subscript m is 1, 2, or 3;

Z is (a)

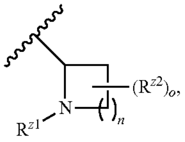

wherein $R^{z1}$ is $C_1$-$C_3$ alkyl;

each $R^{z2}$ is independently fluoro or $C_1$-$C_3$ alkyl;

the subscript n is 1, 2, or 3;

the subscript o is 0, 1, or 2;

(b) —$N(Rz^3)_2$; or (c) —$C(O)N(Rz^3)_2$, wherein each $R^{z3}$ is independently H or $C_1$-$C_3$ alkyl; or alternatively, two $R^{z3}$, together with the nitrogen atom to which they are attached, form a ring $C^z$, wherein ring $C^z$ is an aziridinyl, azetidinyl, pyrrolidinyl, piperidinyl, or azepinyl ring;

wherein ring $C^z$ is unsubstituted or substituted by 1 to 3 fluoro, $C_1$-$C_3$ alkyl, amino, —N(H)($C_1$-$C_3$ alkyl), or —$N(C_1$-$C_3$ $alkyl)_2$, or a pharmaceutically acceptable salt thereof.

In embodiment no. 2, the present disclosure provides a compound of Formula (I) wherein the group

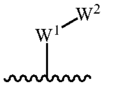 is 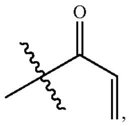, 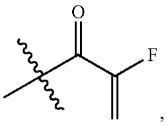,

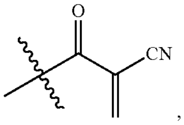, 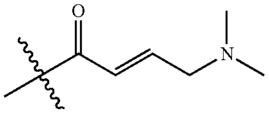,

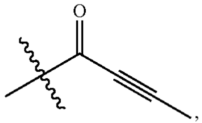, 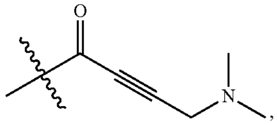,

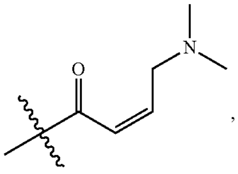, 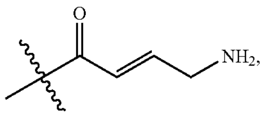,

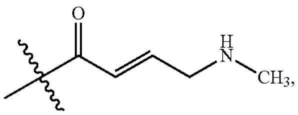,

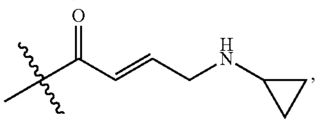,

-continued

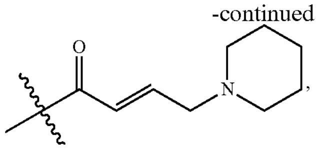,
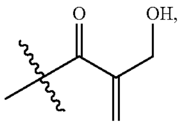,
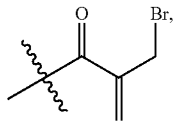,
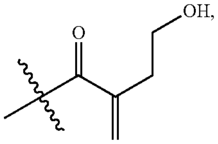,
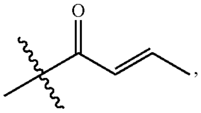,
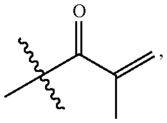,
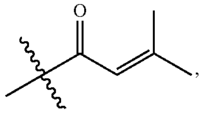, or 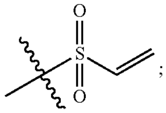;

and the remaining variables are as set forth in embodiment no. 1.

In embodiment no. 3, the group —$W^1$—$W^2$ is —C(O)—C(H)═$CH_2$, and the remaining variables are as set forth in embodiment no. 1.

In embodiment no. 4, the subscript q is 0 or 1, and the remaining variables are as set forth in embodiment no. 1.

In embodiment no. 5, $R^3$ is methyl or —$CH_2$CN, and the remaining variables are as set forth in embodiment no. 1.

In embodiment no. 5, the subscript q is 0 or 1, $R^3$ is methyl or —$CH_2$CN, and the remaining variables are as set forth in embodiment no. 1.

In embodiment no. 6, the group

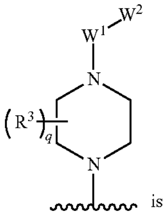 is 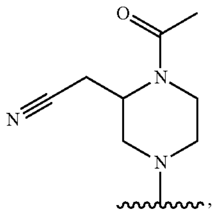, and the remaining variables are as set forth in embodiment no. 1.

In embodiment no. 7, the present disclosure provides a compound of Formula (I) wherein the substructure

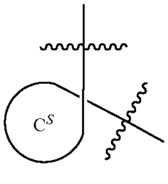 is 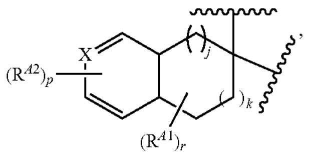, and the remaining variables are as set forth in embodiment no. 1.

In embodiment no. 8, the present disclosure provides a compound as set forth in embodiment no. 7, wherein the subscript j is 0 and the subscript k is 2.

In embodiment no. 9, the present disclosure provides a compound as set forth in embodiment no. 7, wherein the subscript j is 0 and the subscript k is 1.

In embodiment no. 10, the present disclosure provides a compound of Formula (I) wherein the substructure

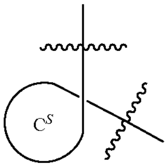 is 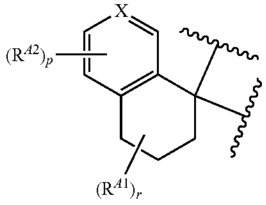

and the remaining variables are as set forth in embodiment no. 1.

In embodiment no. 11, the present disclosure provides a compound as set forth in embodiment no. 7 or 10, wherein X is C(H).

In embodiment no. 12, the present disclosure provides a compound of Formula (I) wherein the substructure is

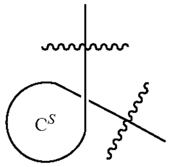 is 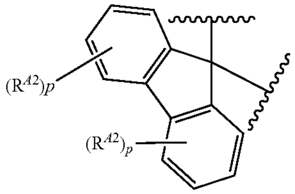

and the remaining variables are as set forth in embodiment no. 1.

In embodiment no. 13, the present disclosure provides a compound of Formula (I) wherein the substructure is

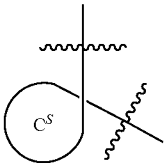 is 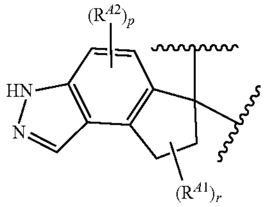

and the remaining variables are as set forth in embodiment no. 1.

In embodiment no. 14, the present disclosure provides a compound of Formula (I) wherein $R^2$ is H and the remaining variables are as set forth in embodiment no. 1.

In embodiment no. 15, the present disclosure provides a compound of Formula (I) wherein Y is —$O(C(R^y)_2)_m$—, the subscript m is 1 or 2, and the remaining variables are as set forth in embodiment no. 1.

In embodiment no. 16, the present disclosure provides a compound as set forth in embodiment no. 15, wherein Z is

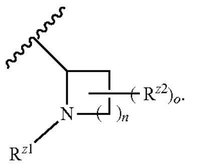

In embodiment no. 17, the present disclosure provides a compound as set forth in embodiment no. 16, wherein the subscript n is 2.

In embodiment no. 18, the present disclosure provides a compound of Formula (I) wherein the group —Y—Z is

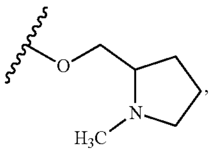
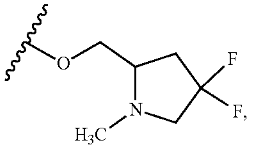
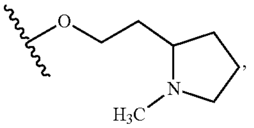
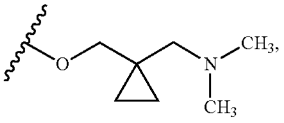
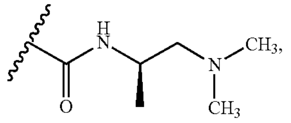
or
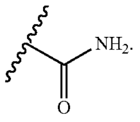

In embodiment no. 19, the present disclosure provides a compound as described in any one of Examples 1-30 as set forth below, or a pharmaceutically acceptable salt thereof.

The present disclosure includes the pharmaceutically acceptable salts of the compounds defined herein, including the pharmaceutically acceptable salts of all structural formulas, embodiments and classes defined herein.

Definitions

Unless defined otherwise, all technical and scientific terms used herein have the same meaning as is commonly understood by one of skill in the art to which this invention belongs.

As used throughout this disclosure, "a compound of Formula (I)" is to be understood to include "a compound of Formula (I) or a pharmaceutically acceptable salt thereof".

"Alkyl", as well as other groups having the prefix "alk", such as alkoxy, and the like, means carbon chains which may be linear or branched, or combinations thereof, containing the indicated number of carbon atoms. In particular embodiments, linear alkyl groups have 1-6 carbon atoms and branched alkyl groups have 3-7 carbon atoms. Examples of alkyl groups include methyl, ethyl, propyl, isopropyl, butyl, sec- and tert-butyl, pentyl, hexyl, heptyl, octyl, nonyl and the like.

"Alkoxy" and "alkyl-O—" are used interchangeably and refer to an alkyl group linked to oxygen.

"Alkylphenyl" refers to a $C_1$-$C_4$ alkyl substituted with a phenyl group. The phenyl group may be anywhere on the carbon chain, e.g., at the end of the carbon chain.

"Bicyclo-ring system" or "bicyclic ring system" refers to two joined rings, wherein the rings are fused, i.e., share two adjacent atoms, or "spirocyclic", i.e., share only a single atom.

"Cyanoalkyl" refers to an alkyl group substituted with a cyano group.

"Cycloalkyl" means a saturated cyclic hydrocarbon radical. In particular embodiments, the cycloalkyl group has 3-12 carbon atoms, forming 1-3 carbocyclic rings that are fused. Examples of cycloalkyl include cyclopropyl, cyclobutyl, cyclopentyl, cyclohexyl, cycloheptyl, adamantyl, and the like.

"Fluoroalkyl" include mono-substituted as well as multiple fluoro-substituted alkyl groups, up to perfluoro substituted alkyl. For example, fluoromethyl, 1,1-difluoroethyl, trifluoromethyl or 1,1,1,2,2-pentafluorobutyl are included.

"Halogen" or "halo" unless otherwise indicated, includes fluorine (fluoro), chlorine (chloro), bromine (bromo) and iodine (iodo). In one embodiment, halo is fluoro (—F) or chloro (—Cl).

"Hydroxyalkyl" includes mono-substituted as well as multiple hydroxy-substituted alkyl groups.

"Spiro-ring system" or "spirocyclic ring system" refers to two joined rings, wherein the rings share only a single atom.

When any variable (e.g., $R^3$) occurs more than one time in any constituent or in Formula (I) or other generic formulas herein, its definition on each occurrence is independent of its definition at every other occurrence. Combinations of substituents and/or variables are permissible only if such combinations result in stable compounds. In choosing compounds of the present disclosure, one of ordinary skill in the art will recognize that the various substituents, e.g., $R^3$, $R^y$, are to be chosen in conformity with well-known principles of chemical structure connectivity and stability. Unless expressly stated to the contrary, substitution by a named substituent is permitted on any atom in a ring (e.g., aryl, a heteroaryl ring, or a saturated heteroaryl ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Unless expressly depicted or described otherwise, variables depicted in a structural formula with a "floating" bond, such as $R^3$ in Formula (I), are permitted on any available carbon atom in the ring to which the variable is attached. When a moiety is noted as being "optionally substituted" in Formula (I) or any embodiment thereof, it means that Formula (I) or the embodiment thereof encompasses compounds that contain the noted substituent (or substituents) on the moiety and also compounds that do not contain the noted substituent (or substituents) on the moiety.

The wavy line , as used herein, indicates a point of attachment to the rest of the compound.

Compounds of Formula (I) may contain one or more asymmetric centers and can thus occur as racemates and racemic mixtures, single enantiomers, diastereoisomeric mixtures and individual diastereoisomers. Centers of asymmetry that are present in the compounds of Formula (I) can all independently of one another have S configuration or R configuration. The compounds of this disclosure include all possible enantiomers and diastereomers and mixtures of two or more stereoisomers, for example, mixtures of enantiomers and/or diastereomers, in all ratios. Thus, enantiomers are a subject of the disclosure in enantiomerically pure form, both as levorotatory and as dextrorotatory antipodes, in the form of racemates and in the form of mixtures of the two enantiomers in all ratios. In the case of a cis/trans isomerism, the disclosure includes both the cis form and the trans form as well as mixtures of these forms in all ratios. The present disclosure is meant to comprehend all such stereoisomeric forms of the compounds of Formula (I). Where a structural formula or chemical name specifies a particular configuration at a stereocenter, the enantiomer or stereoisomer of the compound resulting from that specified stereocenter is intended. Where a structural formula of the compounds of Formula (I) indicates a straight line at a chiral center, the structural formula includes both the S and R stereoisomers associated with the chiral center and mixtures thereof.

Compounds of Formula (I) may be separated into their individual diastereoisomers by, for example, fractional crystallization from a suitable solvent, for example, methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Vibrational circular dichroism (VCD) may also be used to determine the absolute stereochemistry. Alternatively, any stereoisomer or isomers of a compound of Formula (I) may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds of Formula (I) described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of Formula I of the present disclosure.

In the compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present disclosure as described and claimed herein is meant to include all suitable isotopic variations of the compounds of Formula (I) and embodiments thereof. For example, different isotopic forms of hydrogen (H) include protium ($^{1}H$) and deuterium ($^{2}H$, also denoted herein as D). Protium is the predominant hydrogen isotope found in nature. Enriching for deuterium may afford certain therapeutic advantages, such as increasing in vivo half-life or reducing dosage requirements or may provide a compound useful as a standard for characterization of biological samples. Isotopically-enriched compounds of Formula (I), can be prepared without undue experimentation by conventional techniques well known to those skilled in the art or by processes analogous to those described in the Schemes and Examples herein using appropriate isotopically-enriched reagents and/or intermediates.

The term "pharmaceutically acceptable salts" refers to salts prepared from pharmaceutically acceptable non-toxic bases or acids. When the compound of the present disclosure is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present disclosure is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids. If the compounds of Formula (I) simultaneously contain acidic and basic groups in the molecule, the disclosure also includes, in addition to the salt forms mentioned, inner salts or betaines (zwitterions). Salts can be obtained from the compounds of Formula (I) by customary methods which are known to the person skilled in the art, for example, by combination with an organic or inorganic acid or base in a solvent or dispersant, or by anion exchange or cation exchange from other salts. The present disclosure also includes all salts of the compounds of Formula (I) which, owing to low physiological compatibility, are not directly suitable for use in pharmaceuticals but which can be used, for example, as intermediates for chemical reactions or for the preparation of pharmaceutically acceptable salts.

Furthermore, compounds of the present disclosure may exist in amorphous form and/or one or more crystalline forms, and as such all amorphous and crystalline forms and mixtures thereof of the compounds of Formula (I), including the Examples, are intended to be included within the scope of the present disclosure. In addition, some of the compounds of the instant disclosure may form solvates with water (i.e., a hydrate) or common organic solvents such as but not limited to ethyl acetate. Such solvates and hydrates, particularly the pharmaceutically acceptable solvates and hydrates, of the instant compounds are likewise encompassed within the scope of this disclosure, along with un-solvated and anhydrous forms.

Any pharmaceutically acceptable pro-drug modification of a compound of this disclosure which results in conversion in vivo to a compound within the scope of this disclosure is also within the scope of this disclosure.

The present disclosure also relates to processes for the preparation of the compounds of Formula (I) which are described in the following and by which the compounds of the disclosure are obtainable.

The terms "therapeutically effective (or efficacious) amount" and similar descriptions such as "an amount efficacious for treatment" are intended to mean that amount of a compound of Formula (I) that will elicit the biological or medical response of a tissue, a system, animal or human that is being sought by a researcher, veterinarian, medical doctor or other clinician. In a preferred embodiment, the term "therapeutically effective amount" means an amount of a compound of Formula (I) that alleviates at least one clinical symptom in a human patient. The terms "prophylactically effective (or efficacious) amount" and similar descriptions such as "an amount efficacious for prevention" are intended to mean that amount of a compound of Formula (I) that will prevent or reduce the risk of occurrence of the biological or medical event that is sought to be prevented in a tissue, a system, animal or human by a researcher, veterinarian, medical doctor or other clinician.

Dosages of the Compounds of Formula (I)

The dosage regimen utilizing a compound of the instant disclosure is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of an oncological condition, and a prophylactically effective amount, e.g., for prevention of an oncological condition.

While individual needs vary, determination of optimal ranges of effective amounts of the compound of the disclosure is within the skill of the art. For administration to a human in the curative or prophylactic treatment of the conditions and disorders identified herein, for example, typical dosages of the compounds of the present disclosure can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg×5 kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 3 mg/day to about 500 mg/day, about 5 mg/day to about 250 mg/day, about 10 mg/day to about 100 mg/day, about 3 mg/day to about 10 mg/day, or about 100 mg/day to about 250 mg/day. Such doses may be administered in a single dose or may be divided into multiple doses.

Pharmaceutical Compositions

The compounds of Formula (I) and their pharmaceutically acceptable salts can be administered to animals, preferably to mammals, and in particular to humans, as pharmaceuticals by themselves, in mixtures with one another or in the form of pharmaceutical compositions. The term "subject" or "patient" includes animals, preferably mammals and especially humans, who use the instant active agents for the prevention or treatment of a medical condition. Administering of the drug to the subject includes both self-administration and administration to the patient by another person. The subject may be in need of, or desire, treatment for an existing disease or medical condition, or may be in need of or desire prophylactic treatment to prevent or reduce the risk of occurrence of said disease or medical condition. As used herein, a subject "in need" of treatment of an existing condition or of prophylactic treatment encompasses both a determination of need by a medical professional as well as the desire of a patient for such treatment.

The present disclosure therefore also provides the compounds of Formula (I) and their pharmaceutically acceptable salts for use as pharmaceuticals, their use for modulating the activity of mutant KRAS, HRAS and/or NRAS proteins and in particular their use in the therapy and prophylaxis of the below-mentioned diseases or disorders as well as their use for preparing medicaments for these purposes. In certain embodiments, the compounds of Formula (I) and their pharmaceutically acceptable salts inhibit the KRAS G12C protein.

Furthermore, the present disclosure provides pharmaceutical compositions which comprise as active component an effective dose of at least one compound of Formula (I) and/or a pharmaceutically acceptable salt thereof and a customary pharmaceutically acceptable carrier, i.e., one or more pharmaceutically acceptable carrier substances and/or additives.

Thus, the present disclosure provides, for example, said compound and its pharmaceutically acceptable salts for use as pharmaceutical compositions which comprise as active component an effective dose of the compound of Formula (I) and/or a pharmaceutically acceptable salt thereof and a customary pharmaceutically acceptable carrier, and the uses of said compound and/or a pharmaceutically acceptable salt thereof in the therapy or prophylaxis of the below-mentioned diseases or disorders, e.g., cancer, as well as their use for preparing medicaments for these purposes.

The pharmaceutical compositions according to the disclosure can be administered orally, for example, in the form of pills, tablets, lacquered tablets, sugar-coated tablets, granules, hard and soft gelatin capsules, aqueous, alcoholic or oily solutions, syrups, emulsions or suspensions, or rectally, for example, in the form of suppositories. Administration can also be carried out parenterally, for example subcutaneously, intramuscularly or intravenously in the form of solutions for injection or infusion.

Other suitable administration forms are, for example, percutaneous or topical administration, for example, in the form of ointments, tinctures, sprays or transdermal therapeutic systems, or, for example, microcapsules, implants or rods. The preferred administration form depends, for example, on the disease to be treated and on its severity.

The amount of active compound of Formula (I) and/or its pharmaceutically acceptable salts in the pharmaceutical composition normally is from 0.01 to 200 mg, such as from 0.1 to 200 mg, preferably from 1 to 200 mg, per dose, but depending on the type of the pharmaceutical composition, it can also be higher. In some embodiments, the amount of active compound of Formula (I) and/or its pharmaceutically acceptable salts in the pharmaceutical composition is from 0.01 to 10 mg per dose. The pharmaceutical compositions usually comprise 0.5 to 90 percent by weight of the compound of Formula (I) and/or their pharmaceutically acceptable salts. The preparation of the pharmaceutical compositions can be carried out in a manner known per se. For this purpose, one or more compounds of Formula (I) and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules, it is possible to use, for example, lactose, starch, for example, maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example, of solutions for injection, or of emulsions or syrups are, for example, water, physiologically acceptable sodium chloride solution, alcohols such as ethanol, glycerol, polyols, sucrose, invert sugar, glucose, mannitol, vegetable oils, etc. It is also possible to lyophilize the compounds of Formula (I) and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical compositions can also contain customary additives, for example, fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Methods of Using the Compounds of Formula (I)

The present application provides a method of inhibiting RAS-mediated cell signaling comprising contacting a cell with a compound of Formula (I) or a pharmaceutically acceptable salt thereof. Inhibition of RAS-mediated signal transduction can be assessed and demonstrated by a wide variety of ways known in the art. Non-limiting examples include (a) a decrease in GTPase activity of RAS; (b) a decrease in GTP binding affinity or an increase in GDP binding affinity; (c) an increase in $K_{off}$ of GTP or a decrease in $K_{off}$ of GDP; (d) a decrease in the levels of signaling transduction molecules downstream in the RAS pathway, such as a decrease in pMEK, pERK, or pAKT levels; and/or (e) a decrease in binding of RAS complex to downstream signaling molecules including but not limited to Raf. Kits and commercially available assays can be utilized for determining one or more of the above.

The present application also provides methods of using the compounds of Formula (I) (or their pharmaceutically acceptable salts) or pharmaceutical compositions containing such compounds to treat disease conditions, including but not limited to, conditions implicated by mutant KRAS, HRAS and/or NRAS proteins (e.g., cancer), and in some embodiments the KRAS G12C mutant.

In some embodiments, a method for treatment of cancer is provided, the method comprising administering a therapeutically effective amount a compound of Formula (I) (or a pharmaceutically acceptable salt thereof) or any of the foregoing pharmaceutical compositions comprising such a compound to a subject in need of such treatment. In some embodiments, the cancer is mediated by a KRAS, HRAS or NRAS mutation, e.g., the KRAS G12C mutation. In various embodiments, the cancer is pancreatic cancer, colorectal cancer or lung cancer. In some embodiments, the cancer is gall bladder cancer, thyroid cancer, or bile duct cancer.

In some embodiments the present disclosure provides a method of treating a disorder in a subject in need thereof, wherein said method comprises determining if the subject has a KRAS, HRAS or NRAS mutation (e.g., KRAS G12C mutation) and if the subject is determined to have the KRAS, HRAS or NRAS mutation, then administering to the subject a therapeutically effective amount of a compound of Formula (I) or a pharmaceutically acceptable salt thereof.

The disclosed compounds inhibit anchorage-independent cell growth and therefore have the potential to inhibit tumor metastasis. Accordingly, another embodiment of the present disclosure provides a method for inhibiting tumor metastasis, the method comprising administering an effective amount a compound disclosed herein.

KRAS, HRAS or NRAS mutations have also been identified in hematological malignancies (e.g., cancers that affect blood, bone marrow and/or lymph nodes). Accordingly, certain embodiments are directed to administration of the compounds of Formula (I) (e.g., in the form of a pharmaceutical composition) to a subject in need of treatment of a hematological malignancy. Such malignancies include, but are not limited to leukemias and lymphomas. For example, the presently disclosed compounds can be used for treatment of diseases such as acute lymphoblastic leukemia (ALL), acute myelogenous leukemia (AML), chronic lymphocytic leukemia (CLL), small lymphocytic lymphoma (SLL), chronic myelogenous leukemia (CML), acute monocytic leukemia (AMoL) and/or other leukemias. In other embodiments, the compounds are useful for treatment of lymphomas such as Hodgkins lymphoma or non-Hodgkins lymphoma. In various embodiments, the compounds are useful for treatment of plasma cell malignancies such as multiple myeloma, mantle cell lymphoma, and Waldenstrom's macroglubunemia.

Determining whether a tumor or cancer comprises a KRAS, HRAS or NRAS mutation (e.g., the KRAS G12C mutation) can be undertaken by assessing the nucleotide sequence encoding the KRAS, HRAS or NRAS protein, by assessing the amino acid sequence of the KRAS, HRAS or NRAS protein, or by assessing the characteristics of a putative KRAS, HRAS or NRAS mutant protein. The sequences of wild-type human KRAS, HRAS or NRAS are known in the art.

Methods for detecting a mutation in a KRAS, HRAS or NRAS nucleotide sequence are also known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for KRAS, HRAS or NRAS mutations (e.g., the KRAS G12C mutation) by real-time PCR. In real-time PCR, fluorescent probes specific for the KRAS, HRAS or NRAS G12C mutation are used. When a mutation is present, the probe binds and fluorescence is detected. In some embodiments, the KRAS, HRAS or NRAS mutation is identified using a direct sequencing method of specific regions (e.g., exon 2 and/or exon 3) in the KRAS, HRAS or NRAS gene.

Methods for detecting a mutation in a KRAS, HRAS or NRAS protein (e.g., the KRAS G12C mutation) are known by those of skill in the art. These methods include, but are not limited to, detection of a KRAS, HRAS or NRAS mutant using a binding agent (e.g., an antibody) specific for the mutant protein, protein electrophoresis and Western blotting, and direct peptide sequencing.

A number of tissue samples can be assessed for determining whether a tumor or cancer comprises a KRAS, HRAS or NRAS mutation (e.g., the KRAS G12C mutation). In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a circulating tumor cell (CTC) sample. In some embodiments, the sample is processed to a cell lysate. In some embodiments, the sample is processed to DNA or RNA.

The present application also provides a method of treating a hyperproliferative disorder comprising administering a therapeutically effective amount of a compound of the disclosure, or a pharmaceutically acceptable salt thereof to a subject in need thereof. In some embodiments, said method relates to the treatment of a subject who suffers from a cancer such as acute myeloid leukemia, cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer; multiple endocrine neoplasia syndromes, multiple myeloma/plasma cell neoplasm, mycosis fungoides, myelodysplasia syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer; small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

In some embodiments, the methods for treatment are directed to treating lung cancers, and the methods comprise administering a therapeutically effective amount of the compounds of the disclosure (or pharmaceutical composition comprising such compounds) to a subject in need thereof. In certain embodiments, the lung cancer is a non-small cell lung carcinoma (NSCLC), for example, adenocarcinoma, squamous-cell lung carcinoma or large-cell lung carcinoma. In some embodiments, the lung cancer is a small cell lung carcinoma. Other lung cancers which the compounds of Formula (I) may provide therapeutic benefit for include, but are not limited to, glandular tumors, carcinoid tumors and undifferentiated carcinomas.

The present disclosure also provides methods of modulating a mutant KRAS, HRAS or NRAS protein activity (e.g., activity resulting from the KRAS G12C mutation) by contacting the protein with an effective amount of a compound of Formula (I). Modulation can be inhibiting or activating protein activity. In some embodiments, the present disclosure provides methods of inhibiting protein activity by contacting the mutant KRAS, HRAS or NRAS protein (e.g., KRAS G12C mutant) with an effective amount of a compound of Formula (I) in solution. In some embodiments, the present disclosure provides methods of inhibiting the mutant KRAS, HRAS or NRAS protein activity by contacting a cell, tissue, or organ that expresses the protein of interest. In some embodiments, the disclosure provides methods of inhibiting protein activity in subjects including, but not limited to, rodents and mammals (e.g., humans) by administering into the subjects an effective amount of a compound of Formula (I).

Combination Therapies

One or more additional pharmacologically active agents may be administered in combination with a compound of Formula (I) (or a pharmaceutically acceptable salt thereof). An additional active agent (or agents) is intended to mean a pharmaceutically active agent (or agents) that is active in the body, including pro-drugs that convert to pharmaceutically active form after administration, which are different from the compound of Formula (I). The additional active agents also include free-acid, free-base and pharmaceutically acceptable salts of said additional active agents. Generally, any suitable additional active agent or agents, including chemotherapeutic agents or therapeutic antibodies, may be used in any combination with the compound of Formula (I) in a single dosage formulation (e.g., a fixed dose drug combination), or in one or more separate dosage formulations which allows for concurrent or sequential administration of the active agents (co-administration of the separate active agents) to subjects. In addition, the compounds of Formula (I) (or pharmaceutically acceptable salts thereof) can be administered in combination with radiation therapy, hormone therapy, surgery or immunotherapy.

The present application also provides methods for combination therapies in which the additional active agent is known to modulate other pathways, or other components of the same pathway, or even overlapping sets of target enzymes which are used in combination with a compound of Formula (I), or a pharmaceutically acceptable salt thereof. In one embodiment, such therapy includes, but is not limited to, the combination of one or more compounds of Formula (I) with chemotherapeutic agents, immunotherapeutic agents, hormonal and anti-hormonal agents, targeted therapy agents, and anti-angiogenesis agents, to provide a synergistic or additive therapeutic effect. In another embodiment, such therapy includes radiation treatment to provide a synergistic or additive therapeutic effect.

Examples of additional active agents (i.e., additional anti-cancer agents) include chemotherapeutic agents (e.g., cytotoxic agents), immunotherapeutic agents, hormonal and anti-hormonal agents, targeted therapy agents, and anti-angiogenesis agents. Many anti-cancer agents can be classified within one or more of these groups. While certain anti-cancer agents have been categorized within a specific group(s) or subgroup(s) herein, many of these agents can also be listed within one or more other group(s) or subgroup (s), as would be presently understood in the art. It is to be understood that the classification herein of a particular agent into a particular group is not intended to be limiting. Many anti-cancer agents are presently known in the art and can be used in combination with the compounds of the present disclosure.

Further, an agent can be an agonist, antagonist, allosteric modulator, toxin or, more generally, may act to inhibit or stimulate its target (e.g., receptor or enzyme activation or inhibition). For example, suitable for use are one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

In an embodiment, the additional anti-cancer agent is a chemotherapeutic agent, an immunotherapeutic agent, a hormonal agent, an anti-hormonal agent, a targeted therapy agent, or an anti-angiogenesis agent (or angiogenesis inhibitor). In an embodiment, the additional anti-cancer agent is selected from the group consisting of a chemotherapeutic agent, a mitotic inhibitor, a plant alkaloid, an alkylating agent, an anti-metabolite, a platinum analog, an enzyme, a topoisomerase inhibitor, a retinoid, an aziridine, an antibiotic, a hormonal agent, an anti-hormonal agent, an anti-estrogen, an anti-androgen, an anti-adrenal, an androgen, a targeted therapy agent, an immunotherapeutic agent, a biological response modifier, a cytokine inhibitor, a tumor vaccine, a monoclonal antibody, an immune checkpoint inhibitor, an anti-PD-1 agent, an anti-PD-L1 agent, a colony-stimulating factor, an immunomodulator, an immunomodulatory imide (IMiD), an anti-CTLA4 agent, an anti-LAG1 agent, an anti-OX40 agent, a GITR agonist, a CAR-T cell, a BiTE, a signal transduction inhibitor, a growth factor inhibitor, a tyrosine kinase inhibitor, an EGFR inhibitor, a histone deacetylase (HDAC) inhibitor, a proteasome inhibitor, a cell-cycle inhibitor, an anti-angiogenesis agent, a matrix-metalloproteinase (MMP) inhibitor, a hepatocyte growth factor inhibitor, a TOR inhibitor, a KDR inhibitor, a VEGF inhibitor, a HIF-1a inhibitor a HIF-2a inhibitor, a fibroblast growth factor (FGF) inhibitor, a RAF inhibitor, a MEK inhibitor, an ERK inhibitor, a PI3K inhibitor, an AKT inhibitor, an MCL-1 inhibitor, a BCL-2 inhibitor, an SHP2 inhibitor, a HER-2 inhibitor, a BRAF-inhibitor, a gene expression modulator, an autophagy inhibitor, an apoptosis inducer, an antiproliferative agent, and a glycolysis inhibitor.

In one embodiment, the additional anti-cancer agent(s) is a chemotherapeutic agent. Non-limiting examples of chemotherapeutic agents include mitotic inhibitors and plant alkaloids, alkylating agents, anti-metabolites, platinum analogs, enzymes, topoisomerase inhibitors, retinoids, aziridines, and antibiotics.

Non-limiting examples of mitotic inhibitors and plant alkaloids include taxanes such as cabazitaxel, docetaxel, larotaxel, ortataxel, paclitaxel, and tesetaxel; demecolcine; epothilone; eribulin; etoposide (VP-16); etoposide phosphate; navelbine; noscapine; teniposide; thaliblastine; vinblastine; vincristine; vindesine; vinflunine; and vinorelbine.

Non-limiting examples of alkylating agents include nitrogen mustards such as chlorambucil, chlornaphazine, cholophosphamide, cytophosphane, estramustine, ifosfamide, mannomustine, mechlorethamine, mechlorethamine oxide hydrochloride, melphalan, novembichin, phenesterine, prednimustine, tris(2-chloroethyl)amine, trofosfamide, and uracil mustard; alkyl sulfonates such as busulfan, improsulfan, and piposulfan; nitrosoureas such as carmustine, chlorozotocin, fotemustine, lomustine, nimustine, ranimustine, streptozotocin, and TA-07; ethylenimines and methylamelamines such as altretamine, thiotepa, triethylenemelamine, triethylenethiophosphaoramide, trietylenephosphoramide, and trimethylolomelamine; ambamustine; bendamustine; dacarbazine; etoglucid; irofulven; mafosfamide; mitobronitol; mitolactol; pipobroman; procarbazine; temozolomide; treosulfan; and triaziquone.

Non-limiting examples of anti-metabolites include folic acid analogues such as aminopterin, denopterin, edatrexate, methotrexate, pteropterin, raltitrexed, and trimetrexate; purine analogs such as 6-mercaptopurine, 6-thioguanine, fludarabine, forodesine, thiamiprine, and thioguanine; pyrimidine analogs such as 5-fluorouracil (5-FU), 6-azauridine, ancitabine, azacytidine, capecitabine, carmofur, cytarabine, decitabine, dideoxyuridine, doxifiuridine, doxifluridine, enocitabine, floxuridine, galocitabine, gemcitabine, and sapacitabine; 3-aminopyridine-2-carboxaldehyde thiosemicarbazone; broxuridine; cladribine; cyclophosphamide; cytarabine; emitefur; hydroxyurea; mercaptopurine; nelarabine; pemetrexed; pentostatin; tegafur; and troxacitabine.

Non-limiting examples of platinum analogs include carboplatin, cisplatin, dicycloplatin, heptaplatin, lobaplatin, nedaplatin, oxaliplatin, satraplatin, and triplatin tetranitrate.

Non-limiting examples of enzymes include asparaginase and pegaspargase.

Non-limiting examples of topoisomerase inhibitors include acridine carboxamide, amonafide, amsacrine, belotecan, elliptinium acetate, exatecan, indolocarbazole, irinotecan, lurtotecan, mitoxantrone, razoxane, rubitecan, SN-38, sobuzoxane, and topotecan.

Non-limiting examples of retinoids include alitretinoin, bexarotene, fenretinide, isotretinoin, liarozole, RII retinamide, and tretinoin.

Non-limiting examples of aziridines include benzodopa, carboquone, meturedopa, and uredopa.

Non-limiting examples of antibiotics include intercalating antibiotics; anthracenediones; anthracycline antibiotics such as aclarubicin, amrubicin, daunomycin, daunorubicin, doxorubicin, epirubicin, idarubicin, menogaril, nogalamycin, pirarubicin, and valrubicin; 6-diazo-5-oxo-L-norleucine; aclacinomysins; actinomycin; authramycin; azaserine; bleomycins; cactinomycin; calicheamicin; carabicin; carminomycin; carzinophilin; chromomycins; dactinomycin; detorubicin; esorubicin; esperamicins; geldanamycin; marcellomycin; mitomycins; mitomycin C; mycophenolic acid; olivomycins; novantrone; peplomycin; porfiromycin; potfiromycin; puromycin; quelamycin; rebeccamycin; rodorubicin; streptonigrin; streptozocin; tanespimycin; tubercidin; ubenimex; zinostatin; zinostatin stimalamer; and zorubicin.

In one embodiment, the additional anti-cancer agent(s) is a hormonal and/or anti-hormonal agent (i.e., hormone therapy). Non-limiting examples of hormonal and anti-hormonal agents include anti-androgens such as abiraterone, apalutamide, bicalutamide, darolutamide, enzalutamide, flutamide, goserelin, leuprolide, and nilutamide; anti-estrogens such as 4-hydroxy tamoxifen, aromatase inhibiting 4(5)-imidazoles, EM-800, fosfestrol, fulvestrant, keoxifene, LY 117018, onapristone, raloxifene, tamoxifen, toremifene, and trioxifene; anti-adrenals such as aminoglutethimide, dexaminoglutethimide, mitotane, and trilostane; androgens such as calusterone, dromostanolone propionate, epitiostanol, mepitiostane, and testolactone; abarelix; anastrozole; cetrorelix; deslorelin; exemestane; fadrozole; finasteride; formestane; histrelin (RL 0903); human chorionic gonadotropin; lanreotide; LDI 200 (Milkhaus); letrozole; leuprorelin; mifepristone; nafarelin; nafoxidine; osaterone; prednisone; thyrotropin alfa; and triptorelin.

In one embodiment, the additional anti-cancer agent(s) is an immunotherapeutic agent (i.e., immunotherapy). Non-limiting examples of immunotherapeutic agents include biological response modifiers, cytokine inhibitors, tumor vaccines, monoclonal antibodies, immune checkpoint inhibitors, colony-stimulating factors, and immunomodulators.

Non-limiting examples of biological response modifiers, including cytokine inhibitors (cytokines) such as interferons and interleukins, include interferon alfa/interferon alpha such as interferon alfa-2, interferon alfa-2a, interferon alfa-2b, interferon alfa-n1, interferon alfa-n3, interferon alfacon-1, peginterferon alfa-2a, peginterferon alfa-2b, and leukocyte alpha interferon; interferon beta such as interferon beta-1a, and interferon beta-1b; interferon gamma such as natural interferon gamma-1a, and interferon gamma-1b; aldesleukin; interleukin-1 beta; interleukin-2; oprelvekin; sonermin; tasonermin; and virulizin.

Non-limiting examples of tumor vaccines include APC 8015, AVICINE, bladder cancer vaccine, cancer vaccine (Biomira), gastrin 17 immunogen, Maruyama vaccine, melanoma lysate vaccine, melanoma oncolysate vaccine (New York Medical College), melanoma vaccine (New York University), melanoma vaccine (Sloan Kettering Institute), TICE® BCG (*Bacillus* Calmette-Guerin), and viral melanoma cell lysates vaccine (Royal Newcastle Hospital).

Non-limiting examples of monoclonal antibodies include abagovomab, adecatumumab, aflibercept, alemtuzumab, blinatumomab, brentuximab vedotin, CA 125 MAb (Biomira), cancer MAb (Japan Pharmaceutical Development), daclizumab, daratumumab, denosumab, edrecolomab, gemtuzumab zogamicin, HER-2 and Fc MAb (Medarex), ibritumomab tiuxetan, idiotypic 105AD7 MAb (CRC Technology), idiotypic CEA MAb (Trilex), ipilimumab, lintuzumab, LYM-1-iodine 131 MAb (Techni clone), mitumomab, moxetumomab, ofatumumab, polymorphic epithelial mucin-yttrium 90 MAb (Antisoma), ranibizumab, rituximab, and trastuzumab.

Non-limiting examples of immune checkpoint inhibitors include anti-PD-1 agents or antibodies such as cemiplimab, nivolumab, and pembrolizumab; anti-PD-L1 agents or antibodies such as atezolizumab, avelumab, and durvalumab; anti-CTLA-4 agents or antibodies such as ipilumumab; anti-LAG1 agents; and anti-OX40 agents.

Non-limiting examples of colony-stimulating factors include darbepoetin alfa, epoetin alfa, epoetin beta, filgrastim, granulocyte macrophage colony stimulating factor, lenograstim, leridistim, mirimostim, molgramostim, nartograstim, pegfilgrastim, and sargramostim.

Non-limiting examples of additional immunotherapeutic agents include BiTEs, CAR-T cells, GITR agonists, imiquimod, immunomodulatory imides (IMiDs), mismatched double stranded RNA (Ampligen), resiquimod, SRL 172, and thymalfasin.

In one embodiment, the additional anti-cancer agent(s) is a targeted therapy agent (i.e., targeted therapy). Targeted therapy agents include, for example, monoclonal antibodies and small molecule drugs. Non-limiting examples of targeted therapy agents include signal transduction inhibitors, growth factor inhibitors, tyrosine kinase inhibitors, EGFR inhibitors, histone deacetylase (HDAC) inhibitors, proteasome inhibitors, cell-cycle inhibitors, angiogenesis inhibitors, matrix-metalloproteinase (MMP) inhibitors, hepatocyte growth factor inhibitors, TOR inhibitors, KDR inhibitors, VEGF inhibitors, fibroblast growth factors (FGF) inhibitors, MEK inhibitors, ERK inhibitors, PI3K inhibitors, AKT inhibitors, MCL-1 inhibitors, BCL-2 inhibitors, SHP2 inhibitors, HER-2 inhibitors, BRAF-inhibitors, gene expression modulators, autophagy inhibitors, apoptosis inducers, antiproliferative agents, and glycolysis inhibitors.

Non-limiting examples of signal transduction inhibitors include tyrosine kinase inhibitors, multiple-kinase inhibitors, anlotinib, avapritinib, axitinib, dasatinib, dovitinib, imatinib, lenvatinib, lonidamine, nilotinib, nintedanib, pazopanib, pegvisomant, ponatinib, vandetanib, and EGFR inhibitory agents.

Non-limiting examples of EGFR inhibitory agents include small molecule antagonists of EGFR such as afatinib, brigatinib, erlotinib, gefitinib, lapatinib, and osimertinib; and antibody-based EGFR inhibitors, including any anti-EGFR antibody or antibody fragment that can partially or completely block EGFR activation by its natural ligand. Antibody-based EGFR inhibitory agents may include, for example, those described in Modjtahedi, H., et al., 1993, Br. J. Cancer 67:247-253; Teramoto, T., et al., 1996, Cancer 77:639-645; Goldstein et al, 1995, Clin. Cancer Res. 1: 1311-1318; Huang, S. M., et al., 1999, Cancer Res. 15:59(8): 1935-40; and Yang, X., et al., 1999, Cancer Res. 59: 1236-1243; monoclonal antibody Mab E7.6.3 (Yang, 1999 supra); Mab C225 (ATCC Accession No. HB-8508), or an antibody or antibody fragment having the binding specificity thereof; specific antisense nucleotide or siRNA; afatinib, cetuximab; matuzumab; necitumumab; nimotuzumab; panitumumab; and zalutumumab.

Non-limiting examples of histone deacetylase (HDAC) inhibitors include belinostat, panobinostat, romidepsin, and vorinostat.

Non-limiting examples of proteasome inhibitors include bortezomib, carfilzomib, ixazomib, marizomib (salinosporamide a), and oprozomib.

Non-limiting examples of cell-cycle inhibitors, including CDK inhibitors, include abemaciclib, alvocidib, palbociclib, and ribociclib.

In one embodiment, the additional anti-cancer agent(s) is an anti-angiogenic agent (or angiogenesis inhibitor) including, but not limited to, matrix-metalloproteinase (MMP) inhibitors; VEGF inhibitors; EGFR inhibitors; TOR inhibitors such as everolimus and temsirolimus; PDGFR kinase inhibitory agents such as crenolanib; HIF-1$\alpha$ inhibitors such as PX 478; HIF-2a inhibitors such as belzutifan and the HIF-2$\alpha$ inhibitors described in WO 2015/035223; fibroblast growth factor (FGF) or FGFR inhibitory agents such as B-FGF and RG 13577; hepatocyte growth factor inhibitors; KDR inhibitors; anti-Ang1 and anti-Ang2 agents; anti-Tie2 kinase inhibitory agents; Tek antagonists (US 2003/0162712; U.S. Pat. No. 6,413,932); anti-TWEAK agents (U.S. Pat. No. 6,727,225); ADAM distintegrin domain to antagonize the binding of integrin to its ligands (US 2002/0042368); anti-eph receptor and/or anti-ephrin antibodies or antigen binding regions (U.S. Pat. Nos. 5,981,245; 5,728,813; 5,969,110; 6,596,852; 6,232,447; and 6,057,124); and anti-PDGF-BB antagonists as well as antibodies or antigen binding regions specifically binding to PDGF-BB ligands.

Non-limiting examples of matrix-metalloproteinase (MMP) inhibitors include MMP-2 (matrix-metalloproteinase 2) inhibitors, MMP-9 (matrix-metalloproteinase 9) inhibitors, prinomastat, RO 32-3555, and RS 13-0830. Examples of useful matrix metalloproteinase inhibitors are described, for example, in WO 96/33172, WO 96/27583, EP 1004578, WO 98/07697, WO 98/03516, WO 98/34918, WO 98/34915, WO 98/33768, WO 98/30566, EP 0606046, EP 0931788, WO 90/05719, WO 99/52910, WO 99/52889, WO 99/29667, WO 1999/007675, EP 1786785, EP 1181017, US 2009/0012085, U.S. Pat. Nos. 5,863,949, 5,861,510, and EP 0780386. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13).

Non-limiting examples of VEGF and VEGFR inhibitory agents include bevacizumab, cediranib, CEP 7055, CP 547632, KRN 633, orantinib, pazopanib, pegaptanib, pegaptanib octasodium, semaxanib, sorafenib, sunitinib, VEGF antagonist (Borean, Denmark), and VEGF-TRAP™.

The additional anti-cancer agent(s) may also be another anti-angiogenic agent including, but not limited to, 2-methoxyestradiol, AE 941, alemtuzumab, alpha-D148 Mab (Amgen, US), alphastatin, anecortave acetate, angiocidin, angiogenesis inhibitors, (SUGEN, US), angiostatin, anti-Vn Mab (Crucell, Netherlands), atiprimod, axitinib, AZD 9935, BAY RES 2690 (Bayer, Germany, BC 1 (Genoa Institute of Cancer Research, Italy), beloranib, benefin (Lane Labs, US), cabozantinib, CDP 791 (Celltech Group, UK), chondroitinase AC, cilengitide, combretastatin A4 prodrug, CP 564959 (OSI, US), CV247, CYC 381 (Harvard University, US), E 7820, EHT 0101, endostatin, enzastaurin hydrochloride, ER-68203-00 (IVAX, US), fibrinogen-E fragment, Flk-1 (ImClone Systems, US), forms of FLT 1 (VEGFR 1), FR-111142, GCS-100, GW 2286 (GlaxoSmithKline, UK), IL-8, ilomastat, IM-862, irsogladine, KM-2550 (Kyowa Hakko, Japan), lenalidomide, lenvatinib, MAb alpha5beta3 integrin, second generation (Applied Molecular Evolution, USA and Medlmmune, US), MAb VEGF (Xenova, UK), marimastat, maspin (Sosei, Japan), metastatin, motuporamine C, M-PGA, ombrabulin, OXI4503, PI 88, platelet factor 4, PPI 2458, ramucirumab, rBPI 21 and BPI-derived antiangiogenic (XOMA, US), regorafenib, SC-236, SD-7784 (Pfizer, US), SDX 103 (University of California at San Diego, US), SG 292 (Telios, US), SU-0879 (Pfizer, US), TAN-1120, TBC-1635, tesevatinib, tetrathiomolybdate, thalidomide, thrombospondin 1 inhibitor, Tie-2 ligands (Regeneron, US), tissue factor pathway inhibitors (EntreMed, US), tumor necrosis factor-alpha inhibitors, tumstatin, TZ 93, urokinase plasminogen activator inhibitors, vadimezan, vandetanib, vasostatin, vatalanib, VE-cadherin-2 antagonists, xanthorrhizol, XL 784 (Exelixis, US), ziv-aflibercept, and ZD 6126.

In embodiments, the additional anti-cancer agent(s) is an additional active agent that disrupts or inhibits RAS-RAF-ERK or PI3K-AKT-TOR signaling pathways or is a PD-1 and/or PD-L1 antagonist. In embodiments, the additional anti-cancer agent(s) is a RAF inhibitor, EGFR inhibitor, MEK inhibitor, ERK inhibitor, PI3K inhibitor, AKT inhibitor, TOR inhibitor, MCL-1 inhibitor, BCL-2 inhibitor, SHP2 inhibitor, proteasome inhibitor, or immune therapy, including monoclonal antibodies, immunomodulatory imides (IMiDs), anti-PD-1, anti-PDL-1, anti-CTLA4, anti-LAG1, and anti-OX40 agents, GITR agonists, CAR-T cells, and BiTEs.

Non-limiting examples of RAF inhibitors include dabrafenib, encorafenib, regorafenib, sorafenib, and vemurafenib.

Non-limiting examples of MEK inhibitors include binimetinib, CI-1040, cobimetinib, PD318088, PD325901, PD334581, PD98059, refametinib, selumetinib, and trametinib.

Non-limiting examples of ERK inhibitors include LY3214996, LTT462, MK-8353, SCH772984, ravoxertinib, ulixertinib, and an ERKi as described in WO 2017/068412.

Non-limiting examples of PI3K inhibitors include 17-hydroxywortmannin analogs (e.g., WO 06/044453); AEZS-136; alpelisib; AS-252424; buparlisib; CAL263; copanlisib; CUDC-907; dactolisib (WO 06/122806); demethoxyviridin; duvelisib; GNE-477; GSK1059615; IC87114; idelalisib; INK1117; LY294002; Palomid 529; paxalisib; perifosine; PI-103; PI-103 hydrochloride; pictilisib (e.g., WO 09/036,082; WO 09/055,730); PIK 90; PWT33597; SF1126; sonolisib; TGI 00-115; TGX-221; XL147; XL-765; wortmannin; and ZSTK474.

Non-limiting examples of AKT inhibitors include Akt-1-1 (inhibits Aktl) (Barnett et al. (2005) *Biochem. J.,* 385 (Pt. 2), 399-408); Akt-1-1,2 (Barnett et al. (2005) *Biochem. J.* 385 (Pt. 2), 399-408); API-59CJ-Ome (e.g., Jin et al. (2004) Br. J. Cancer 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and Li (2004) *J Nutr.* 134(12 Suppl), 3493S-3498S); perifosine, Dasmahapatra et al. (2004) *Clin. Cancer Res.* 10(15), 5242-

52, 2004); phosphatidylinositol ether lipid analogues (e.g., Gills and Dennis (2004) *Expert. Opin. Investig. Drugs* 13, 787-97); triciribine (Yang et al. (2004) Cancer Res. 64, 4394-9); imidazooxazone compounds including trans-3-amino-1-methyl-3-[4-(3-phenyl-5H-imidazo[1,2-c]pyrido [3,4-e][1,3]oxazin-2-yl)phenyl]-cyclobutanol hydrochloride (WO 2012/137870); afuresertib; capivasertib; MK2206; patasertib; and those disclosed in WO 2011/082270 and WO 2012/177844.

Non-limiting examples of TOR inhibitors include deforolimus; ATP-competitive TORC1/TORC2 inhibitors, including PI-103, PP242, PP30, and Torin 1; TOR inhibitors in FKBP12 enhancer, rapamycins and derivatives thereof, including temsirolimus, everolimus, WO 9409010; rapalogs, e.g. as disclosed in WO 98/02441 and WO 01/14387, e.g. AP23573, AP23464, or AP23841; 40-(2-hydroxyethyl) rapamycin, 40-[3-hydroxy(hydroxymethyl)methylpropanoate]-rapamycin; 40-epi-(tetrazolyl)-rapamycin (also called ABT578); 32-deoxorapamycin; 16-pentynyloxy-32(S)-dihydrorapanycin, and other derivatives disclosed in WO 05/005434; derivatives disclosed in U.S. Pat. No. 5,258,389, WO 94/090101, WO 92/05179, U.S. Pat. Nos. 5,118,677, 5,118,678, 5,100,883, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; and phosphorus-containing rapamycin derivatives (e.g., WO 05/016252).

Non-limiting examples of MCL-1 inhibitors include AMG-176, MIK665, and S63845.

Non-limiting examples of SHP2 inhibitors include SHP2 inhibitors described in WO 2019/167000 and WO 2020/022323.

Additional non-limiting examples of anti-cancer agents that are suitable for use include 2-ethylhydrazide, 2,2',2"-trichlorotriethylamine, ABVD, aceglatone, acemannan, aldophosphamide glycoside, alpharadin, amifostine, aminolevulinic acid, anagrelide, ANCER, ancestim, anti-CD22 immunotoxins, antitumorigenic herbs, apaziquone, arglabin, arsenic trioxide, azathioprine, BAM 002 (Novelos), bcl-2 (Genta), bestrabucil, biricodar, bisantrene, bromocriptine, brostallicin, bryostatin, buthionine sulfoximine, calyculin, cell-cycle nonspecific antineoplastic agents, celmoleukin, clodronate, clotrimazole, cytarabine ocfosfate, DA 3030 (Dong-A), defofamine, denileukin diftitox, dexrazoxane, diaziquone, dichloroacetic acid, dilazep, discodermolide, docosanol, doxercalciferol, edelfosine, eflornithine, EL532 (Elan), elfomithine, elsamitrucin, eniluracil, etanidazole, exisulind, ferruginol, folic acid replenisher such as frolinic acid, gacytosine, gallium nitrate, gimeracil/oteracil/tegafur combination (S-1), glycopine, histamine dihydrochloride, HIT diclofenac, HLA-B7 gene therapy (Vical), human fetal alpha fetoprotein, ibandronate, ibandronic acid, ICE chemotherapy regimen, imexon, iobenguane, IT-101 (CRLX101), laniquidar, LC 9018 (Yakult), leflunomide, lentinan, levamisole+fluorouracil, lovastatin, lucanthone, masoprocol, melarsoprol, metoclopramide, miltefosine, miproxifene, mitoguazone, mitozolomide, mopidamol, motexafin gadolinium, MX6 (Galderma), naloxone+pentazocine, nitracrine, nolatrexed, NSC 631570 octreotide (Ukrain), olaparib, P-30 protein, PAC-1, palifermin, pamidronate, pamidronic acid, pentosan polysulfate sodium, phenamet, picibanil, pixantrone, platinum, podophyllinic acid, porfimer sodium, PSK (Polysaccharide-K), rabbit antithymocyte polyclonal antibody, rasburiembodiment, retinoic acid, rhenium Re 186 etidronate, romurtide, samarium (153 Sm) lexidronam, sizofiran, sodium phenylacetate, sparfosic acid, spirogermanium, strontium-89 chloride, suramin, swainsonine, talaporfin, tariquidar, tazarotene, tegafur-uracil, temoporfin, tenuazonic acid, tetrachlorodecaoxide, thrombopoietin, tin ethyl etiopurpurin, tirapazamine, TLC ELL-12, tositumomab-iodine 131, trifluridine and tipiracil combination, troponin I (Harvard University, US), urethan, valspodar, verteporfin, zoledronic acid, and zosuquidar.

The present disclosure further provides a method for using the compounds of Formula (I) or pharmaceutical compositions provided herein, in combination with radiation therapy to treat cancer. Techniques for administering radiation therapy are known in the art, and these techniques can be used in the combination therapy described herein. The administration of the compound of Formula (I) in this combination therapy can be determined as described herein.

Radiation therapy can be administered through one of several methods, or a combination of methods, including, without limitation, external-beam therapy, internal radiation therapy, implant radiation, stereotactic radiosurgery, systemic radiation therapy, radiotherapy and permanent or temporary interstitial brachy therapy. The term "brachytherapy," as used herein, refers to radiation therapy delivered by a spatially confined radioactive material inserted into the body at or near a tumor or other proliferative tissue disease site. The term is intended, without limitation, to include exposure to radioactive isotopes (e.g., At-211, 1-131, 1-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as 1-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of 1-125 or 1-131, or a radioactive fluid can be produced using a slurry of a suitable fluid containing small particles of solid radionuclides, such as Au-198, Y-90. Moreover, the radionuclide (s) can be embodied in a gel or radioactive microspheres.

The present disclosure also provides methods for combination therapies in which the additional active agent is known to modulate other pathways, or other components of the same pathway, or even overlapping sets of target enzymes which are used in combination with a compound of Formula (I), or a pharmaceutically acceptable salt thereof. In one embodiment, such therapy includes, but is not limited to, the combination of one or more compounds of Formula (I) with chemotherapeutic agents, immunotherapeutic agents, hormonal therapy agents, therapeutic antibodies, targeted therapy agents, and radiation treatment, to provide a synergistic or additive therapeutic effect.

The compounds of the disclosure can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound of Formula (I) and any of the agents described above can be formulated together in the same dosage form and administered simultaneously. Alternatively, a compound of Formula (I) and any of the agents described above can be simultaneously administered, wherein both the agents are present in separate formulations. In another alternative, a compound of Formula (I) can be administered just followed by and any of the agents described above, or vice versa. In some embodiments of the separate administration protocol, a compound of Formula (I) and any of the agents described above are administered a few minutes apart, or a few hours apart, or a few days apart.

As one aspect of the present disclosure contemplates the treatment of the disease/conditions with a combination of pharmaceutically active compounds that may be administered separately, the disclosure further relates to combining separate pharmaceutical compositions in kit form. The kit comprises two separate pharmaceutical compositions: a compound of Formula (I), and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

The present disclosure also provides for the compound of Formula (I), or the pharmaceutically acceptable salt thereof, for use in therapy, or use of the compound of Formula (I), or the pharmaceutically acceptable salt thereof, in therapy. The present disclosure also provides for the compound of Formula (I), or the pharmaceutically acceptable salt thereof, for use in treating cancer, or use of a compound of Formula (I), or the pharmaceutically acceptable salt thereof, for treating cancer. The present disclosure also provides for the compound of Formula (I), or the pharmaceutically acceptable salt thereof, for the preparation of a medicament for the treatment of cancer, or use of the compound of Formula (I), or the pharmaceutically acceptable salt thereof, for the preparation of a medicament for the treatment of cancer. The present disclosure also provides for the compound of Formula (I), or the pharmaceutically acceptable salt thereof, and an additional anti-cancer agent, for use in the treatment of cancer, or use of the compound of Formula (I), or the pharmaceutically acceptable salt thereof, and the additional anti-cancer agent for treating cancer. The disclosure also provides the compound of Formula (I), or the pharmaceutically acceptable salt thereof, and an additional anti-cancer agent, for the preparation of a medicament for the treatment of cancer, or use of the compound of Formula (I), or the pharmaceutically acceptable salt thereof, and the additional anti-cancer agent, for the preparation of a medicament for the treatment of cancer. The present disclosure also provides for a pharmaceutical composition comprising the compound of Formula (I), or the pharmaceutically acceptable salt thereof, for use in the treatment of cancer, or use of the pharmaceutical composition comprising the compound of Formula (I), or the pharmaceutically acceptable salt thereof, for treating cancer. The present disclosure also provides for a pharmaceutical composition comprising the compound of Formula (I), or the pharmaceutically acceptable salt thereof, and an additional anti-cancer agent, for use in the treatment of cancer, or use of the pharmaceutical composition comprising the compound of Formula (I), or the pharmaceutically acceptable salt thereof, and the additional anti-cancer agent, for treating cancer.

Methods of Preparing the Compounds of the Disclosure

Several methods for preparing the compounds of this disclosure are described in the following Examples. Starting materials and intermediates are purchased, made from known procedures, or as otherwise illustrated.

Throughout the synthetic schemes and examples, abbreviations and acronyms may be used with the following meanings unless otherwise indicated:

anhydr.=Anhydrous; aq.=aqueous; atm=atmosphere; BnOH=benzyl alcohol; Bodipy-GDP=mixture of ((2R,3S,4R,5R)-5-(2-amino-6-oxo-1,6-dihydro-9H-purin-9-yl)-3-(((2-(3-(5,5-difluoro-7,9-dimethyl-5H-414,514-dipyrrolo[1,2-c:2',1'-f][1,3,2]diazaborinin-3-yl)propanamido)ethyl)carbamoyl)oxy)-4-hydroxytetrahydrofuran-2-yl)methyl hydrogen diphosphate and ((2R,3R,4R,5R)-5-(2-amino-6-oxo-1,6-dihydro-9H-purin-9-yl)-4-(((2-(3-(5,5-difluoro-7,9-dimethyl-5H-414,514-dipyrrolo[1,2-c:2',1'-f][1,3,2]diazaborinin-3-yl)propanamido)ethyl)carbamoyl)oxy)-3-hydroxytetrahydrofuran-2-yl)methyl hydrogen diphosphate (Invitrogen™, catalog number G22360); BOP=benzotriazol-1-yloxytris(dimethylamino)phosphonium hexafluorophosphate; br s=broad singlet; Bu=butyl; t-Bu=tert-butyl; cataCxium® C=trans-Di(p-acetato)bis[o-(di-o-tolylphosphino)benzyl]dipalladium (II), C=$CDCl_3$=deuterated chloroform; Cbz=carboxybenzyl; CDI=1,1'-carbonyldiimidazole, CELITE=diatomaceous earth; $CF_3$=trifluoromethyl; cGMP=cyclic guanosine monophosphate; $CH_3NO_2$=nitromethane; conc.=concentrated; DBU=1,8-diazabicyclo[5.4.0]undec-7-ene; DCM=dichloromethane; DETA-NO=Diethylenetriamine/nitric oxide adduct; DHP=3,4-dihydropyran; DIAD=Diisopropyl azodicarboxylate; DIEA/DIPEA=N,N-Diisopropylethylamine; DME=dimethoxyethane, DMEA=N,N-Dimethylethanamine, DMF=N,N-dimethylformamide; DMP=Dess-Martin periodinane; DMS=dimethylsulfide; DMSO=dimethylsulfoxide; DPPF or dppf=1,1'-bis(diphenylphosphino)ferrocene; DTT=dithiothreitol; EDTA=ethylenediaminetetraacetic acid; equiv, eq.=equivalent(s); Et=ethyl; $Et_3N$=triethylamine; EtOAc=ethyl acetate; EtOH=ethanol; Grubbs Catalyst=(1,3-Bis(2,4,6-trimethylphenyl)-2-imidazolidinylidene)dichloro(phenylmethylene)(tricyclohexylphosphine)ruthenium; GTP=guanosine triphosphate; h=hour; HATU=1-[bis(dimethylamino)methylene]-1H-1,2,3-triazolo[4,5-b]pyridinium 3-oxid hexafluorophosphate; HEPES=4-(2-hydroxyethyl)-1-piperazineethanesulfonic acid; HMDS=hexamethydisilazane; HPLC=High pressure liquid chromatography; Int.=intermediate; iPr=isopropyl; IP=inflection points; i-PrOH=Isopropanol; KHMDS=Potassium bis(trimethylsilyl)amide; LCMS, LC/MS=liquid chromatography-mass spectrometry; min, min.=minute; LDA=lithium diisopropylamide; M=Molar; m-CPBA=3-chloroperbenzoic acid; Me=methyl; MeCN, ACN=acetonitrile; MeOH=methanol; mp, m.p.=melting point; mpk=milligrams per kilogram; MsCl=Methanesulfonyl chloride; MOM=methoxymethyl; MPLC=medium pressure liquid chromatography; N=Normal; NaOMe=sodium methoxide; NMR=nuclear magnetic resonance; N.D.=not determined; PDA=photodiode array; Pet. ether=petroleum ether; Pd—C=palladium on carbon; $Pd_2(dba)_3$=tris(dibenzylideneacetone)dipalladium (0); Ph=phenyl; Pr=propyl; psi=pounds per square inch gauge; $POCl_3$=phosphorus(V) oxide chloride; PPTS=pyridinium p-toluenesulfonate; PTLC, prep TLC=preparative thin layer chromatography; pTsOH, PTSA=p-toluenesulfonic acid; PyBroP=bromo-tris-pyrrolidino-phosphonium hexafluorophosphate; rac=racemic; RT=retention time; RP-HPLC=reverse phase HPLC; rt=room temperature; sat.=saturated; SFC=supercritical fluid chromatography; SOS=Son of Sevenless; Sphos Pd G3=(2-Dicyclohexylphosphino-2',6'-dimethoxybiphenyl) [2-(2'-amino-1,1'-biphenyl)] palladium(II) methanesulfonate; T3P=propanephosphonic acid anhydride; TBAF=tetra-n-butylammonium fluoride; TBSCl=tert-butyldimethylsilyl chloride; $Tf_2O$=triflic anhydride; TFA=trifluoroacetic acid; TLC=thin layer chromatography; THF=tetrahydrofuran; THP=tetrahydropyran; TMS=trimethylsilyl; TWEEN=polyoxyethylene (20) sorbitan monolaurate; VCD=vibrational circular dichroism; v, v/v=volume, volume to volume; w, w/w=weight, weight to weight, XPhos-Pd-G3=(2-dicyclohexylphosphino-2',4',6'-triisopropyl-1,1'-biphenyl) [2-(2'-amino-1,1'-biphenyl)]palladium(II) methanesulfonate; μm=micrometer.

EXAMPLES

The compounds described herein can be prepared according to the procedures of the following schemes and examples, using appropriate materials and are further exemplified by the following specific examples. The compounds illustrated in the examples are not, however, to be construed as forming the only genus that is considered as the disclosure. The examples further illustrate details for the preparation of the compounds of the present disclosure. Those skilled in the art will readily understand that known variations of the conditions and processes of the following preparative procedures can be used to prepare these compounds. These examples are provided for the purpose of further illustration only and are not intended to be limitations on the disclosure. Any intermediates described below may be referred to herein by their number preceded by "Int-."

Concentration refers to the removal of the volatile components at reduced pressure (e.g., by rotary evaporation) unless otherwise noted. All temperatures are in degrees Celsius unless otherwise noted. Mass spectra (MS) were measured by electrospray ion-mass spectroscopy (ESI) in positive ion detection mode and m/z refers to the $[M+H]^+$ ion unless otherwise noted. $^1H$ NMR spectra were recorded at 400-500 MHz at ambient temperature unless otherwise noted. Protons reported as 0.5 H are due to rotameric signals. RP-HPLC refers to reverse-phase HPLC on C18-functionalized preparative or semi-preparative columns with gradient elution using acetonitrile and water modified with trifluoroacetic acid or ammonium hydroxide as eluents and fractions were lyophilized or concentrated by rotary evaporation unless otherwise noted. Purification by column chromatography on silica gel was accomplished using a flash chromatography system (e.g., ISCO® or Biotage®) and commercial pre-packed silica gel columns with elution using the stated solvent systems. Compounds described herein were synthesized as the racemates unless otherwise noted in the experimental procedures and compound tables. Certain products/intermediates in the examples include indication of "Peak 1" and/or "Peak 2", which refer to the order of elution of the indicated product/intermediate from the chromatography column (e.g., an SFC column) used to isolate the compound under the specified conditions. Thus, for example, Peak 1 refers to the first eluting compound, e.g., first eluting stereoisomer under the specified conditions.

SFC Columns used in the chiral resolution of stereoisomers are summarized in the following Table:

| SFC Column | Abbreviation |
|---|---|
| Chiral Technologies, OD-H (21 mm × 250 mm, 5 um) | Column A |
| Chiral Technologies, IB-N (21 mm × 250 mm, 5 um) | Column B |
| YMC, SJ (21 mm × 250 mm, 5 um) | Column C |
| Waters, XSelect C18 (30 mm × 150 mm, 5 um) | Column D |
| Daicel Chiracel OD-H (30 mm × 250 mm, 5 um) | Column E |
| Chiral Technologies, OJ-H (21 mm × 250 mm, 5 um) | Column F |
| ES Industries, CCAF4 (21 mm × 250 mm, 5 um) | Column G |
| Phenomenex, LUX-4 (21 mm × 250 mm, 5 um) | Column H |
| Phenomenex, LUX-3 (21 mm × 250 mm, 5 um) | Column I |
| Regis, (S, S) Whelk-O1 (30 mm × 250 mm, 5 um) | Column J |
| Phenomenex, Cellulose-2 (30 mm × 250 mm, 10 um) | Column K |
| Phenomenex, Cellulose-2 (30 mm × 250 mm, 5 um) | Column L |
| Regis, (R, R) Whelk-O1 (21 mm × 250 mm, 5 um) | Column M |

Preparation of Int A1: 1-methylene-1,2,3,4-tetrahydronaphthalene

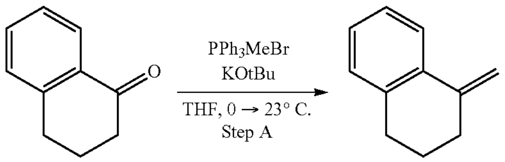

Methyltriphenylphosphonium bromide (4.89 g, 13.7 mmol) was dissolved in THF (30.4 mL) and potassium tert-butoxide (2.23 g, 19.8 mmol) was added. The reaction mixture was stirred for 30 minutes at room temperature. The reaction mixture was then cooled to 0° C. and α-tetralone (1.84 ml, 13.7 mmol) was added dropwise as a solution in THF (2 mL). The reaction mixture was slowly warmed to room temperature and allowed to stir overnight. The reaction mixture was diluted with 50 mL hexanes and filtered. 50 mL water was added to the filtrate and the layers were separated. The organic layer was dried with $MgSO_4$ and concentrated. The residual crude material was taken up in hexanes again, sonicated, and filtered once more. The filtrate was concentrated to ~15 mL and this material was loaded onto an 80 g silica gel column, eluting with 100% hexane to yield 1-methylene-1,2,3,4-tetrahydronaphthalene (Int A1). MS (ESI): $[M+H]^+$ m/z: 145.

Alkene starting materials within the table were prepared using procedures similar to that described for Int A1, using the corresponding commercially available ketone.

| Ex. | Structure | Characterization Data |
|---|---|---|
| Int A2 | 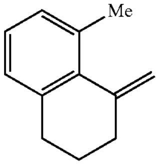 | MS (ESI): $[M + H]^+$ m/z: 179 |
| Int A3 | 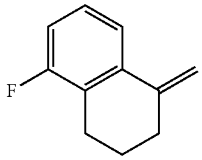 | MS (ESI): $[M + H]^+$ m/z: 163 |
| Int A4 | 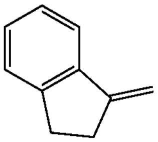 | $^1$H NMR (CHLOROFORM-d) δ: 7.46-7.51 (m, 1H), 7.44 (d, J = 7.3 Hz, 2H), 7.30-7.35 (m, 2H), 5.43 (t, J = 2.4 Hz, 1H), 5.02 (t, J = 2.0 Hz, 1H), 2.92-3.01 (m, 2H), 2.79 (ddt, J = 6.8, 4.5, 2.4 Hz, 2H) |
| Int A5 | 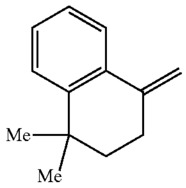 | MS (ESI): $[M + H]^+$ m/z: 173 |
| Int A6 | 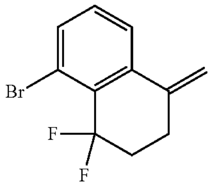 | MS (ESI): $[M + H]^+$ m/z: 259, 261 |
| Int A7 | 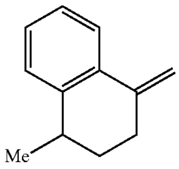 | MS (ESI): $[M + H]^+$ m/z: 159 |
| Int A8 | 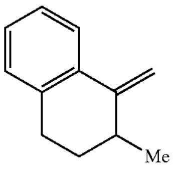 | MS (ESI): $[M + H]^+$ m/z: 159 |
| Int A9 | 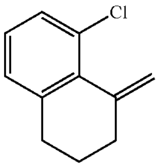 | MS (ESI): $[M + H]^+$ m/z: 179 |
| Int A10 | 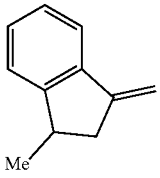 | $^1$H NMR (500 MHz, CHLOROFORM-d) δ = 7.50-7.45 (m, 1H), 7.25-7.19 (m, 3H), 5.44 (s, 1H), 5.02 (s, 1H), 3.30-3.27 (m, 1H), 3.05-3.00 (m, 1H), 2.39-3.35 (m, 1H), 1.43 (s, 3H). |

-continued

| Ex. | Structure | Characterization Data |
|---|---|---|
| Int A11 | 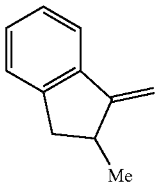 | $^1H$ NMR (500 MHz, METHANOL-$d_4$) δ = 7.39-7.36 (m, 1H), 7.14-7.05 (m, 3H), 5.38 (d, J = 2.6 Hz, 1H), 4.87 (d, J = 2.1 Hz, 1H), 3.08 (dd, J = 8.4, 16.2 Hz, 1H), 2.94-2.85 (m, 1H), 2.44 (dd, J = 5.2, 16.2 Hz, 1H), 1.14 (d, J = 7.0 Hz, 3H). |
| Int A12 | 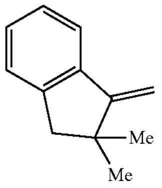 | $^1H$ NMR (400 MHz, CHLOROFORM-d) δ = 7.50-7.45 (m, 1H), 7.26-7.18 (m, 3H), 5.44 (s, 1H), 4.92 (s, 1H), 2.83 (s, 2H), 1.22 (s, 6H). |
| Int A13 | 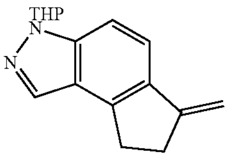 | $^1H$ NMR (400 MHz, CHLOROFORM-d) δ = 7.97 (s, 1H), 7.53-7.48 (m, 1H), 7.46-7.40 (m, 1H), 5.70 (dd, J = 2.7, 9.3 Hz, 1H), 5.35 (t, J = 2.3 Hz, 1H), 4.99-4.95 (m, 1H), 4.07-3.97 (m, 1H), 3.79-3.69 (m, 1H), 3.24-3.13 (m, 2H), 2.96-2.87 (m, 2H), 2.63-2.48 (m, 1H), 2.21-2.10 (m, 1H), 2.05 (br dd, J = 3.9, 13.9 Hz, 1H), 1.82-1.62 (m, 3H). |
| Int A14 | 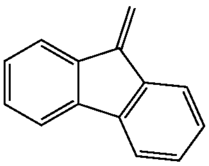 | $^1H$ NMR (500 MHz, CHLOROFORM-d) δ = 7.75 (d, J = 7.5 Hz, 2H), 7.71 (d, J = 7.5 Hz, 2H), 7.39 (dt, J = 0.8, 7.4 Hz, 2H), 7.36-7.29 (m, 2H), 6.09 (s, 2H) |
| Int A15 | 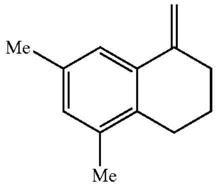 | MS (ESI): $[M + H]^+$ m/z: 173 |

Preparation of Int B1: 1-(benzyloxy)-8-methylene-5,6,7,8-tetrahydroisoquinoline

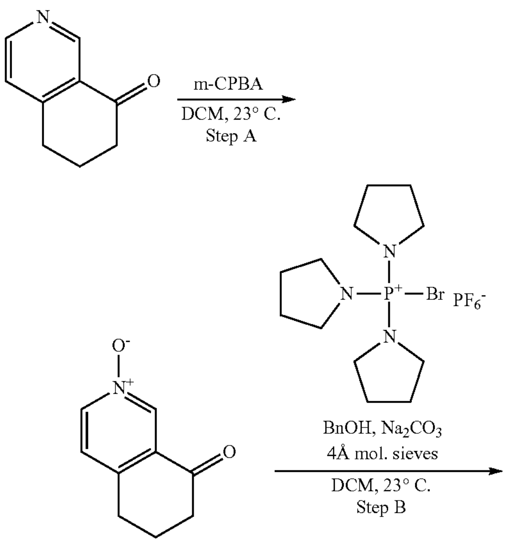

-continued

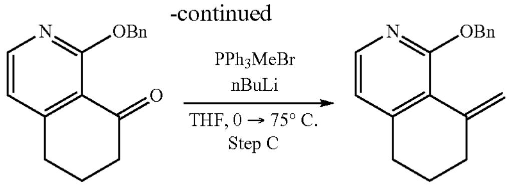

Int-B1

Step A: 8-oxo-5,6,7,8-tetrahydroisoquinoline 2-oxide m-CPBA (4.57 g, 20.4 mmol) was added to a solution of 6,7-dihydroisoquinolin-8(5H)-one (2.50 g, 17.0 mmol) in DCM (170 mL). The reaction was stirred vigorously at room temperature for 1 h. The reaction was concentrated under reduced pressure and purified by silica gel chromatography (gradient elution: 0-20% MeOH/DCM) to provide to provide 8-oxo-5,6,7,8-tetrahydroisoquinoline 2-oxide. MS (ESI): $[M+H]^+$ m/z: 164.

Step B: 1-(benzyloxy)-6,7-dihydroisoquinolin-8(5H)-one

Benzyl alcohol (1.03 mL, 9.9 mmol) and PyBroP (2.15 g, 4.61 mmol) were sequentially added to a suspension of 8-oxo-5,6,7,8-tetrahydroisoquinoline 2-oxide (537 mg, 3.29 mmol), sodium carbonate (698 mg, 6.58 mmol), and 4 Å molecular sieves (236 mg/mmol) in DCM (13.2 mL). The reaction was stirred vigorously at room temperature overnight. The reaction was filtered through celite, diluted with water (25 mL) and extracted with DCM (2×10 mL). The combined organic layers were dried over anhydrous $MgSO_4$, filtered, and concentrated under reduced pressure. The crude residue was then purified by silica gel chromatography (gradient elution: 0-50% EtOAc/Hexanes) to provide 1-(benzyloxy)-6,7-dihydroisoquinolin-8(5H)-one. MS (ESI): $[M+H]^+$ m/z: 254.

Step C: 1-(benzyloxy)-8-methylene-5,6,7,8-tetrahydroisoquinoline (Int B1)

n-Butyllithium (4.13 mL, 6.61 mmol) was added to a suspension of methyltriphenylphosphonium bromide (1.77 g, 4.96 mmol) in THF (8.81 mL) dropwise at 0° C. The reaction was stirred vigorously at 0° C. for 30 minutes. A solution of 1-(benzyloxy)-6,7-dihydroisoquinolin-8(5H)-one (837 mg, 3.30 mmol) in THF (2.20 mL) was added dropwise at 0° C. The reaction stirred at room temperature overnight. The reaction was then heated to 75° C. for 5 hours. The reaction was cooled to room temperature, diluted with sat. aq. $NH_4Cl$ (25 mL) and extracted with EtOAc (3×25 mL). The combined organic layers were dried over anhydrous $MgSO_4$, filtered, and concentrated under reduced pressure. The crude residue was purified by silica gel chromatography (gradient elution: 0-5% EtOAc/Hexanes) to provide 1-(benzyloxy)-8-methylene-5,6,7,8-tetrahydroisoquinoline (Int B1). MS (ESI): $[M+H]^+$ m/z: 254.

Preparation of Int C1: 2-methylene-2,3-dihydro-1H-indene

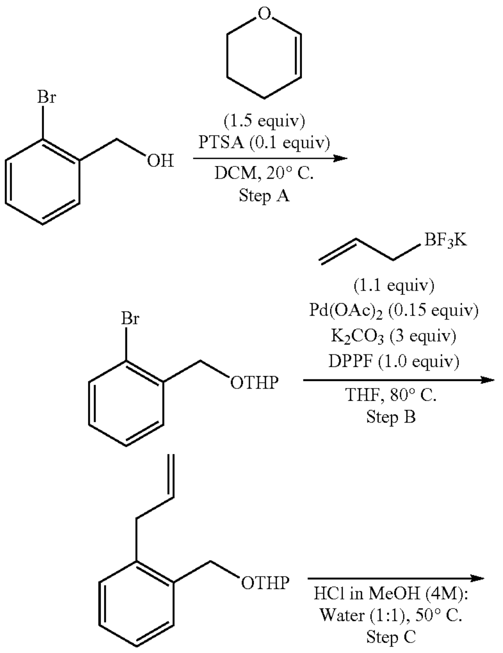

-continued

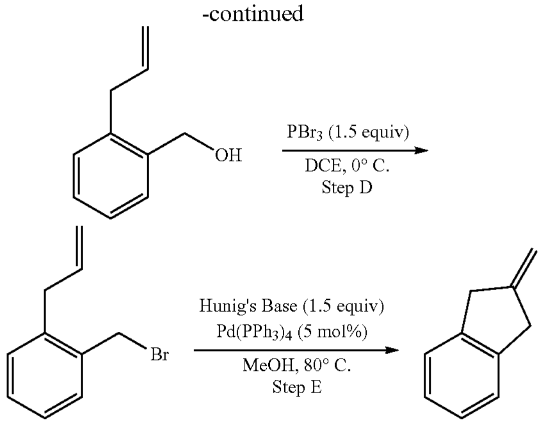

Int C1

Step A: 2-((2-bromobenzyl)oxy)tetrahydro-2H-pyran

A mixture of (2-bromophenyl)methanol (700 mg, 3.74 mmol), dihydropyran (0.513 ml, 5.61 mmol) and PTSA (64.4 mg, 0.374 mmol) in DCM (15 ml) was stirred at 20° C. for 5 h. The solvent was removed under reduced pressure and the residue was dissolved in water (20 mL) and EtOAc (20 mL). The organic layer was separated and the aqueous was extracted with EtOAc (3×20 mL). The combined organic layers were washed with brine (50 mL), dried over anhydrous $Na_2SO_4$, filtered and concentrated under reduced pressure. The residue was purified by flash silica gel chromatography using an eluent of 2% ethyl acetate/pet. ether gradient to give 2-((2-bromobenzyl)oxy)tetrahydro-2H-pyran.

$^1H$ NMR (500 MHz, CHLOROFORM-d) δ 7.51-7.56 (m, 2H), 7.32 (dt, J=1.05, 7.45 Hz, 1H), 7.14 (dt, J=1.05, 7.45 Hz, 1H), 4.83 (d, J=13.28 Hz, 1H), 4.78 (t, J=3.51 Hz, 1H), 4.58 (d, J=13.28 Hz, 1H), 3.93 (ddd, J=3.05, 8.74, 11.41 Hz, 1H), 3.54-3.60 (m, 1H), 1.86-1.94 (m, 1H), 1.68-1.82 (m, 2H), 1.57-1.68 (m, 3H).

Step B: 2-((2-allylbenzyl)oxy)tetrahydro-2H-pyran

A microwave vial was charged with potassium allyltrifluoroborate (60.0 mg, 0.406 mmol), 2-((2-bromobenzyl)oxy)tetrahydro-2H-pyran (100 mg, 0.369 mmol), potassium carbonate (153 mg, 1.11 mmol), DPPF (204 mg, 0.369 mmol) and THF (4 ml) at 20° C. The mixture was bubbled with a stream of $N_2$ for 5 min. The tube was sealed and heated to 80° C. for 1 h. The reaction mixture is cooled to room temperature, filtered through a CELITE pad, and washed with 20 mL of EtOAc. The mixture was filtered and the filtrate was concentrated. The residue was purified by Prep-TLC (silica gel, ethyl acetate/pet. ether=1/20, v/v) to give 2-((2-allylbenzyl)oxy)tetrahydro-2H-pyran. $^1H$ NMR (400 MHz, CHLOROFORM-d) δ 7.31-7.36 (m, 1H), 7.10-7.18 (m, 3H), 5.85-5.97 (m, 1H), 4.91-5.01 (m, 2H), 4.74 (d, J=12.23 Hz, 1H), 4.63 (t, J=3.42 Hz, 1H), 4.44 (d, J=11.96 Hz, 1H), 3.81-3.89 (m, 1H), 3.45-3.52 (m, 1H), 3.37-3.42 (m, 2H), 1.49-1.86 (m, 6H)

Step C: (2-allylphenyl)methanol

A mixture of 2-((2-allylbenzyl)oxy)tetrahydro-2H-pyran (1.7 g, 7.32 mmol) in HCl in MeOH (4 M) (10 ml) and water (10.00 ml) was stirred at 50° C. for 17 h. The solvent was removed under reduced pressure and the residue was dissolved in water (20 mL) and EtOAc (20 mL). The organic layer was separated and the aqueous was re-extracted with EtOAc (3×20 mL). The combined organic layers were washed with brine (50 mL), dried over anhydrous $Na_2SO_4$, filtered and concentrated under reduced pressure. The residue was purified by flash silica gel chromatography using an eluent of 8% ethyl acetate/pet. ether gradient to give (2-allylphenyl)methanol. $^1H$ NMR (400 MHz, CHLOROFORM-d) δ 7.30-7.56 (m, 3H), 7.15-7.17 (m, 1H), 5.99 (tdd, J=6.24, 10.24, 16.80 Hz, 1H), 5.06 (dd, J=1.60, 10.24 Hz, 1H), 4.99 (dd, J=1.72, 16.80 Hz, 1H), 4.74 (s, 1H), 4.70 (s, 2H), 3.47 (d, J=6.12 Hz, 2H).

Step D: 1-allyl-2-(bromomethyl)benzene $PBr_3$ (4.77 ml, 50.6 mmol) was slowly added to a 0° C. solution of (2-allylphenyl)methanol (5 g, 33.7 mmol) in DCE (60 ml). After addition, the mixture was stirred at 0° C. for 1 h to give a colorless mixture. The reaction mixture was quenched with ice water (200 mL) and extracted with DCM (3×100 mL). The combined organic phases were washed with brine (500 mL), dried over anhydrous $Na_2SO_4$, filtered and concentrated under reduced pressure. The residue was chromatographed on silica gel (pet. ether/EtOAc=100:0 to 98:2) to give compound 1-allyl-2-(bromomethyl)benzene. $^1H$ NMR (500 MHz, CHLOROFORM-d) δ 7.33-7.36 (m, 1H), 7.28-7.32 (m, 1H), 7.18-7.24 (m, 2H), 6.03 (dd, J=10.15, 17.00 Hz, 1H), 5.11 (dd, J=1.60, 10.15 Hz, 1H), 5.05 (dd, J=1.60, 17.00 Hz, 1H), 4.55 (s, 2H), 3.55 (d, J=6.25 Hz, 2H).

Step E: 2-methylene-2,3-dihydro-1H-indene (Int C1)

A microwave vial was charged with 1-allyl-2-(bromomethyl)benzene (100 mg, 0.474 mmol), Hunig's base (0.099 ml, 0.568 mmol), $Pd(Ph_3P)_4$ (27.4 mg, 0.024 mmol) and MeCN (5 ml) at 20° C. The mixture was bubbled with a stream of $N_2$ for 1 min. The tube was sealed and heated to 80° C. for 0.5 h. The mixture was cooled to room temperature, filtered and the filtrate was concentrated under reduced pressure to give the crude product. The crude was purified by Prep-TLC (silica gel, pet. ether) to give 2-methylene-2,3-dihydro-1H-indene (Int C1). $^1H$ NMR (400 MHz, CHLOROFORM-d) δ 7.20-7.24 (m, 2H), 7.15-7.19 (m, 2H), 5.10 (t, J=2.54 Hz, 2H), 3.71 (t, J=2.16 Hz, 4H)

Example 1a/b: 2-((2S)-1-acryloyl-4-(8-methyl-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile

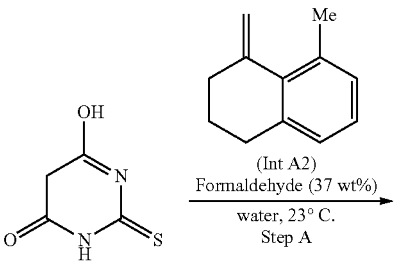

-continued

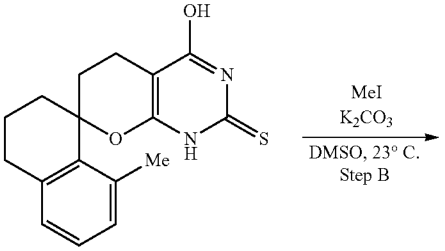

Int 1a

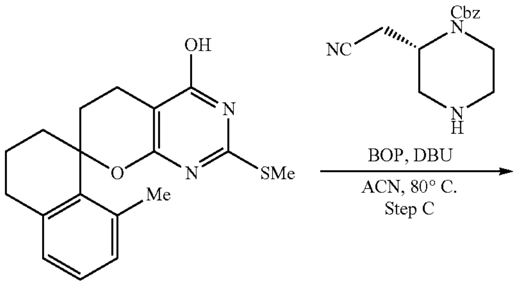

Int 1b

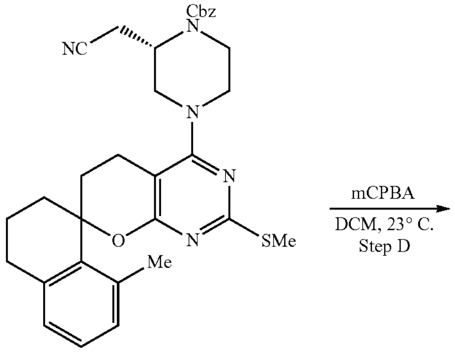

Int 1c

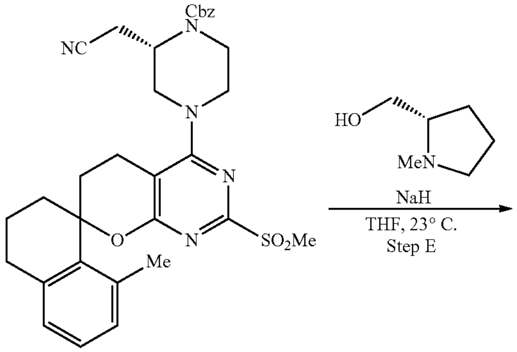

Int 1d

-continued

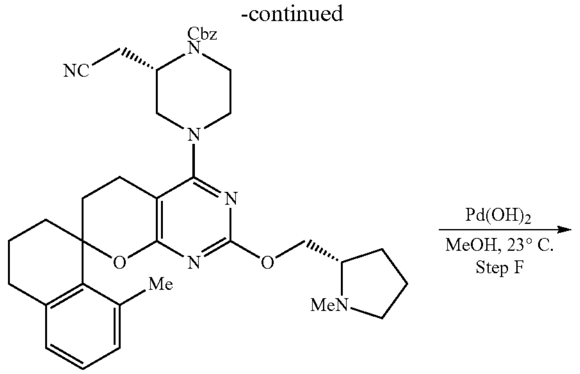

Int 1e

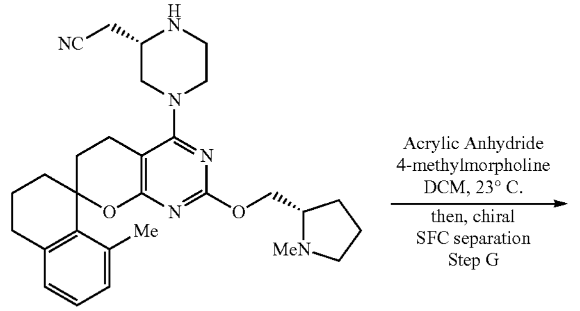

Int 1f

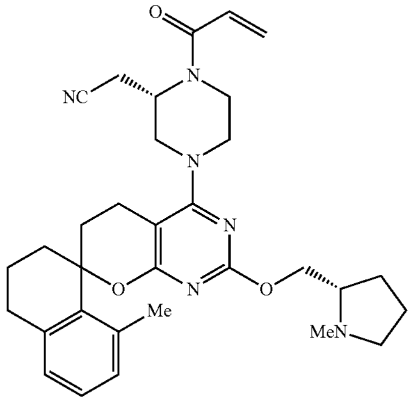

Ex. 1a
Ex. 1b

Step A: 4'-hydroxy-8-methyl-3,4,5',6'-tetrahydro-2H-spiro[naphthalene-1,7'-pyrano[2,3-d]pyrimidine]-2'(1'H)-thione (Int 1a)

To a mixture of 8-methyl-1-methylene-1,2,3,4-tetrahydronaphthalene (Int A2, 572 mg, 3.61 mmol), 2-thioxodihydropyrimidine-4,6(1H,5H)-dione (782 mg, 5.42 mmol) and formaldehyde (37% in $H_2O$) (0.538 mL, 7.23 mmol) was added water (15 mL). The reaction mixture was stirred at room temperature for 4 h. The suspension was lyophilized overnight to yield 4'-hydroxy-8-methyl-3,4,5',6'-tetrahydro-2H-spiro[naphthalene-1,7'-pyrano[2,3-d]pyrimidine]-2'(1'H)-thione (Int 1a). MS (ESI): $[M+H]^+$ m/z: 315.

Step B: 8-methyl-2'-(methylthio)-3,4,5',6'-tetrahydro-2H-spiro[naphthalene-1,7'-pyrano[2,3-d]pyrimidin]-4'-ol (Int 1b)

To a solution of 4'-hydroxy-8-methyl-3,4,5',6'-tetrahydro-2H-spiro[naphthalene-1,7'-pyrano[2,3-d]pyrimidine]-2'(1'H)-thione (Int 1a) (1.1 g, 3.50 mmol) in acetonitrile (14 mL) was added $K_2CO_3$ (0.725 g, 5.25 mmol). The reaction was stirred at room temperature for 1 h and iodomethane (0.219 mL, 3.50 mmol) was added. The reaction mixture was then stirred at room temperature over the weekend. The reaction mixture was filtered and the solid collected was dried under vacuum to yield 8-methyl-2'-(methylthio)-3,4,5',6'-tetrahydro-2H-spiro[naphthalene-1,7'-pyrano[2,3-d]pyrimidin]-4'-ol (Int 1b). MS (ESI): $[M+H]^+$ m/z: 329.

Step C: benzyl (2S)-2-(cyanomethyl)-4-(8-methyl-2'-(methylthio)-3,4,5',6'-tetrahydro-2H-spiro[naphthalene-1,7'-pyrano[2,3-d]pyrimidin]-4'-yl)piperazine-1-carboxylate (Int 1c)

To a solution of 8-methyl-2'-(methylthio)-3,4,5',6'-tetrahydro-2H-spiro[naphthalene-1,7'-pyrano[2,3-d]pyrimidin]-4'-ol (Int 1b) (400 mg, 1.218 mmol) in acetonitrile (5500 μl) was added benzyl 2-(cyanomethyl)piperazine-1-carboxylate (632 mg, 2.436 mmol), BOP (700 mg, 1.583 mmol) followed by DBU (556 μl, 3.65 mmol). The resulting mixture was heated at 80° C. overnight. The reaction mixture was quenched with water (5 mL) and extracted with EtOAc (3×5 mL). The combined organic layers were concentrated and purified using 24 g silica gel column with 30% of EtOAc in hexanes to yield benzyl (2S)-2-(cyanomethyl)-4-(8-methyl-2'-(methylthio)-3,4,5',6'-tetrahydro-2H-spiro[naphthalene-1,7'-pyrano[2,3-d]pyrimidin]-4'-yl)piperazine-1-carboxylate (Int 1c). MS (ESI): $[M+H]^+$ m/z: 570.

Step D: benzyl (2S)-2-(cyanomethyl)-4-(8-methyl-2'-(methylsulfonyl)-3,4,5',6'-tetrahydro-2H-spiro[naphthalene-1,7'-pyrano[2,3-d]pyrimidin]-4'-yl) piperazine-1-carboxylate (Int 1d)

A mixture of benzyl (2S)-2-(cyanomethyl)-4-(8-methyl-2'-(methylthio)-3,4,5',6'-tetrahydro-2H-spiro[naphthalene-1,7'-pyrano[2,3-d]pyrimidin]-4'-yl)piperazine-1-carboxylate (Int 1c) (150 mg, 0.263 mmol) and 3-chlorobenzoperoxoic acid (136 mg, 0.790 mmol) in DCM (1400 μl) was stirred at room temperature for 3 h. The reaction mixture was diluted with DCM, filtered and the filtrate was washed with saturated, aqueous $NaHCO_3$ solution. The combined organic layers were concentrated to yield benzyl (2S)-2-(cyanomethyl)-4-(8-methyl-2'-(methylsulfonyl)-3,4,5',6'-tetrahydro-2H-spiro[naphthalene-1,7'-pyrano[2,3-d]pyrimidin]-4'-yl)piperazine-1-carboxylate (Int 1d). MS (ESI): $[M+H]^+$ m/z: 602.

Step E: benzyl (2S)-2-(cyanomethyl)-4-(8-methyl-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazine-1-carboxylate (Int 1e)

To a mixture of NaH (32.9 mg, 0.823 mmol), (S)-(1-methylpyrrolidin-2-yl)methanol (98 μL, 0.823 mmol, purchased from Sigma Aldrich) and benzyl (2S)-2-(cyanomethyl)-4-(8-methyl-2'-(methylsulfonyl)-3,4,5',6'-tetrahydro-2H-spiro[naphthalene-1,7'-pyrano[2,3-d]pyrimidin]-4'-yl) piperazine-1-carboxylate (Int 1d) (165 mg, 0.274 mmol) was added THF (1400 μL) under nitrogen. The reaction mixture was stirred at room temperature for 1 h. The reaction was then diluted with methanol and concentrated. The crude material was purified by 24 g silica gel column with 30% of methanol in DCM to yield benzyl (2S)-2-(cyanomethyl)-4-(8-methyl-2'-(((S)-1-methylpyrrolidin-2-yl)methoxy)-3,4,5', 6'-tetrahydro-2H-spiro[naphthalene-1,7'-pyrano[2,3-d]pyrimidin]-4'-yl)piperazine-1-carboxylate (Int 1e). MS (ESI): $[M+H]^+$ m/z: 637.

Step F: 2-((2S)-4-(8-methyl-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile (Int 1f)

An 8 mL vial was charged with $Pd(OH)_2$ (22 mg, 0.031 mmol) and benzyl (2S)-2-(cyanomethyl)-4-(8-methyl-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazine-1-carboxylate (Int 1e) (80 mg, 0.126 mmol) in MeOH (1000 μl) was added under nitrogen. The reaction mixture was degassified with vacuum and back filled with nitrogen thrice and stirred under hydrogen balloon at room temperature for 4 h. The reaction mixture was filtered over CELITE and the filtrate was concentrated to yield 2-((2S)-4-(8-methyl-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile (Int if). MS (ESI): $[M+H]^+$ m/z: 503.

Step G: 2-((2S)-1-acryloyl-4-(8-methyl-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile (Ex. 1a/b)

To a solution of 2-((2S)-4-(8-methyl-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile (Int 1f) (58 mg, 0.115 mmol) in DCM (850 μl) was added 4-methylmorpholine (38.1 μl, 0.346 mmol)) and acrylic anhydride (15.96 μl, 0.138 mmol) under nitrogen. The reaction mixture was stirred at room temperature for 30 minutes. The reaction mixture was then diluted with DCM, washed with brine solution and concentrated. The crude material was purified by 24 g silica gel column with 20% of methanol in DCM to yield racemic product. The racemic material was resolved by SFC (Column A; $CH_3CN$/MeOH and 30% MeOH (with 0.1% $NH_4OH$)) to provide 2-((2S)-1-acryloyl-4-(8-methyl-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile; Peak 1 (Ex. 1a) MS (ESI): $[M+H]^+$ m/z: 557; $^1H$ NMR (499 MHz, DMSO-d6) δ 7.11 (t, J=7.5 Hz, 1H), 6.99 (d, J=7.6 Hz, 2H), 6.87 (d, J=40.5 Hz, 1H), 6.19 (d, J=16.5 Hz, 1H), 5.78 (d, J=10.4 Hz, 1H), 4.95 (s, 1H), 4.76 (s, 1H), 4.27 (d, J=6.1 Hz, 1H), 4.12-3.92 (m, 2H), 3.86 (s, 1H), 3.61 (s, 1H), 3.22 (br. s, 2H), 3.08-2.71 (m, 6H), 2.65-2.56 (m, 2H), 2.41 (s, 3H), 2.31 (s, 4H), 2.09 (dq, J=26.7, 9.3 Hz, 2H), 2.02-1.91 (m, 1H), 1.82 (s, 3H), 1.70 (s, 2H), 1.66-1.55 (m, 1H). And 2-((2S)-1-acryloyl-4-(8-methyl-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile Peak 2 (Ex. 1b) MS (ESI): $[M+H]^+$ m/z: 557; $^1H$ NMR (499 MHz, DMSO-d6) δ 7.12 (t, J=7.5 Hz, 1H), 7.00 (d, J=7.6 Hz, 2H), 6.87 (s, 1H), 6.19 (dd, J=16.7, 1.8 Hz, 1H), 5.79 (d, J=12.2 Hz, 1H), 4.99 (s, 1H), 4.70 (s, 1H), 4.45 (s, 1H), 4.29-4.14 (m, 2H), 4.07 (s, 1H), 3.98 (d, J=13.5 Hz, 1H), 3.80 (s, 1H), 3.16-2.62 (m, 9H), 2.50-2.35 (m, 4H), 2.30 (s, 4H), 2.09 (tt, J=14.5, 8.2 Hz, 2H), 2.01-1.87 (m, 1H), 1.91-1.53 (m, 6H).

Using procedures similar to those described in Example 1, Examples 2-12 in the table below were prepared from the specified alkene precursors. For the preparation of Examples 5a and 5b, the substituted pyrrolidine reagent used to form the group —Y—Z was purchased from AstaTech. For the preparation of Examples 12a and 12b, the substituted cyclopropyl reagent used to form the group —Y—Z was purchased from Enamine.

| Ex. | Alkene Precursor | Structure Fraction Collected | Compound Name | $[M+H]^+$ Found | SFC Conditions |
|---|---|---|---|---|---|
| Ex 2a | Int A1 | 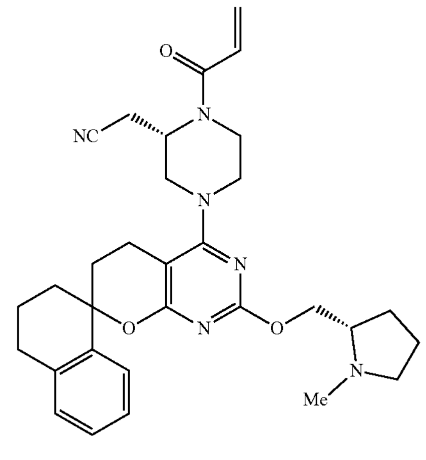 [SMILES: C=CC(=O)N1CCN(c2nc(OC[C@@H]3CCCN3C)nc3c2CCC2(CCCc4ccccc42)O3)C[C@@H]1CC#N] Peak 1 | 2-((2S)-1-acryloyl-4-(2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile | 543.3 | Column A; Condition: $CH_3CN$/MeOH and 35% Methanol (0.1% $NH_4OH$) |

-continued

| Ex. | Alkene Precursor | Structure Fraction Collected | Compound Name | [M + H]+ Found | SFC Conditions |
|---|---|---|---|---|---|
| 2b | Int A1 | 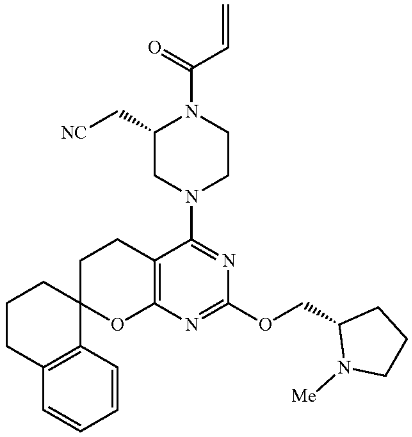 [SMILES: C=CC(=O)N1CCN(c2nc(OC[C@@H]3CCCN3C)nc3c2CCC2(CCCc4ccccc42)O3)C[C@@H]1CC#N] Peak 2 | 2-((2S)-1-acryloyl-4-(2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile | 543.3 | |
| 3a | Int A3 | 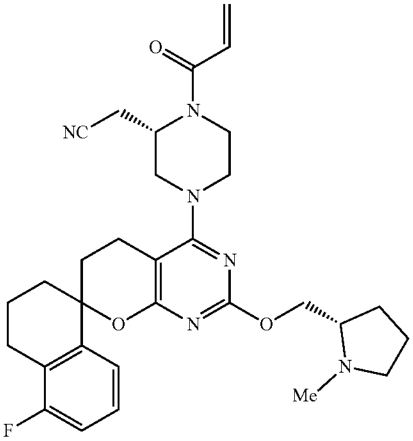 [SMILES: C=CC(=O)N1CCN(c2nc(OC[C@@H]3CCCN3C)nc3c2CCC2(CCCc4c(F)cccc42)O3)C[C@@H]1CC#N] Peak 1 | 2-((2S)-1-acryloyl-4-(5-fluoro-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile | 561.2 | Column A; Condition: Methanol and 40% Methanol (0.1% $NH_4OH$) |
| 3b | Int A3 | 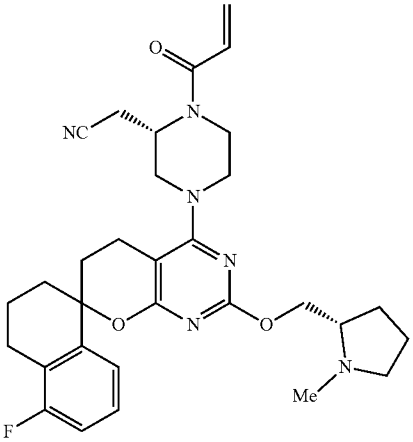 [SMILES: C=CC(=O)N1CCN(c2nc(OC[C@@H]3CCCN3C)nc3c2CCC2(CCCc4c(F)cccc42)O3)C[C@@H]1CC#N] Peak 2 | 2-((2S)-1-acryloyl-4-(5-fluoro-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile | 561.2 | |

-continued

| Ex. | Alkene Precursor | Structure Fraction Collected | Compound Name | $[M + H]^+$ Found | SFC Conditions |
|---|---|---|---|---|---|
| 4a | Int A4 | 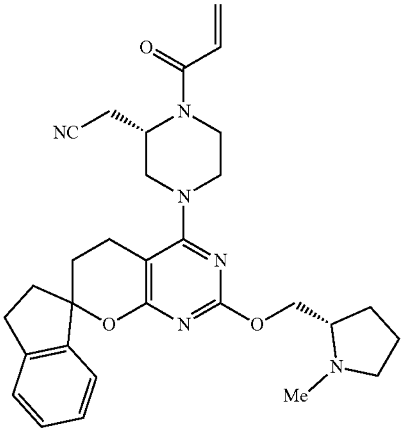 [SMILES: C=CC(=O)N1CCN(c2nc(OC[C@@H]3CCCN3C)nc3c2CCC2(CCc4ccccc42)O3)C[C@@H]1CC#N] Peak 1 | 2-((2S)-1-acryloyl-4-(2'-(((S)-1-methylpyrrolidin-2-yl)methoxy)-2,3,5',6'-tetrahydrospiro[indene-1,7'-pyrano[2,3-d]pyrimidin]-4'-yl)piperazin-2-yl)acetonitrile | 529.2 | Column A; Condition: Methanol and 40% Methanol (0.1% $NH_4OH$) |
| 4b | Int A4 | 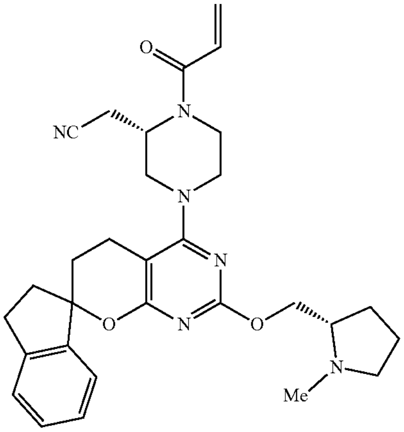 [SMILES: C=CC(=O)N1CCN(c2nc(OC[C@@H]3CCCN3C)nc3c2CCC2(CCc4ccccc42)O3)C[C@@H]1CC#N] Peak 2 | 2-((2S)-1-acryloyl-4-(2'-(((S)-1-methylpyrrolidin-2-yl)methoxy)-2,3,5',6'-tetrahydrospiro[indene-1,7'-pyrano[2,3-d]pyrimidin]-4'-yl)piperazin-2-yl)acetonitrile | 529.2 | |
| 5a | Int A1 | 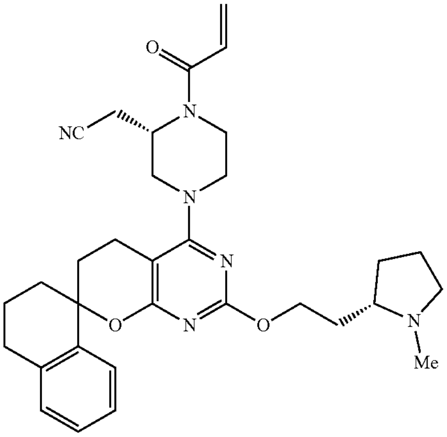 [SMILES: C=CC(=O)N1CCN(c2nc(OCC[C@@H]3CCCN3C)nc3c2CCC2(CCCc4ccccc42)O3)C[C@@H]1CC#N] Peak 1 | 2-((2S)-1-acryloyl-4-(2'-(2-((S)-1-methylpyrrolidin-2-yl)ethoxy)-3,4,5',6'-tetrahydro-2H-spiro[naphthalene-1,7'-pyrano[2,3-d]pyrimidin]-4'-yl)piperazin-2-yl)acetonitrile | 557.3 | Column A; Condition: Methanol and 40% Methanol (0.1% $NH_4OH$) |

-continued

| Ex. | Alkene Precursor | Structure Fraction Collected | Compound Name | $[M + H]^+$ Found | SFC Conditions |
|---|---|---|---|---|---|
| 5b | Int A1 | 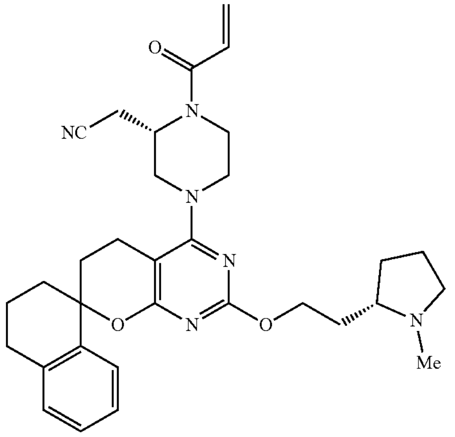 [SMILES: C=CC(=O)N1CCN(c2nc(OCC[C@@H]3CCCN3C)nc3c2CCC2(CCCc4ccccc42)O3)C[C@@H]1CC#N] Peak 2 | 2-((2S)-1-acryloyl-4-(2'-(2-((S)-1-methylpyrrolidin-2-yl)ethoxy)-3,4,5',6'-tetrahydro-2H-spiro[naphthalene-1,7'-pyrano[2,3-d]pyrimidin]-4'-yl)piperazin-2-yl)acetonitrile | 557.3 | |
| 6a | Int A5 | 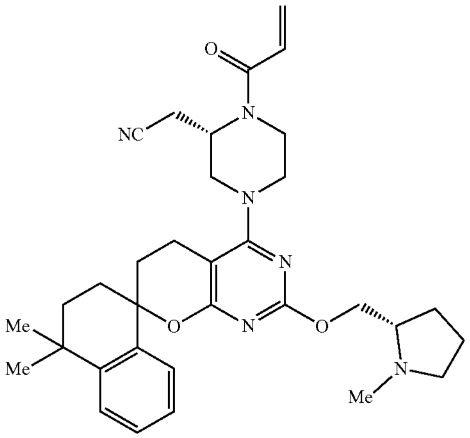 [SMILES: C=CC(=O)N1CCN(c2nc(OC[C@@H]3CCCN3C)nc3c2CCC2(CCC(C)(C)c4ccccc42)O3)C[C@@H]1CC#N] Peak 1 | 2-((2S)-1-acryloyl-4-(4,4-dimethyl-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile | 571.4 | Column A; Condition: Methanol and 30% Methanol (0.1% $NH_4OH$) |
| 6b | Int A5 | 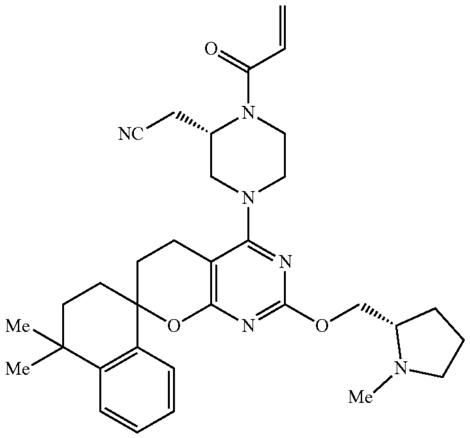 [SMILES: C=CC(=O)N1CCN(c2nc(OC[C@@H]3CCCN3C)nc3c2CCC2(CCC(C)(C)c4ccccc42)O3)C[C@@H]1CC#N] Peak 2 | 2-((2S)-1-acryloyl-4-(4,4-dimethyl-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile | 571.4 | |

-continued

| Ex. | Alkene Precursor | Structure Fraction Collected | Compound Name | [M + H]+ Found | SFC Conditions |
|---|---|---|---|---|---|
| 7a | Int A6 | 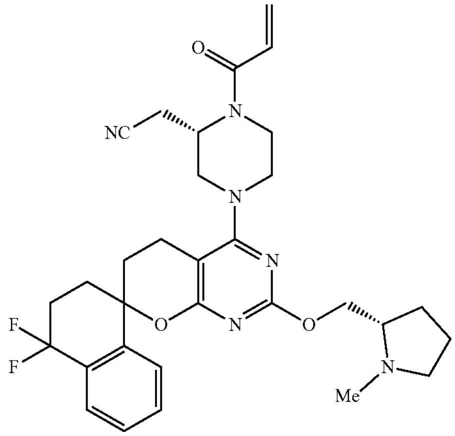 [SMILES: C=CC(=O)N1CCN(c2nc(OC[C@@H]3CCCN3C)nc3c2CCC2(CCC(F)(F)c4ccccc42)O3)C[C@@H]1CC#N] Peak 1 | 2-((2S)-1-acryloyl-4-(4,4-difluoro-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile | | Column A; Condition: Methanol and 25% Methanol (0.1% $NH_4OH$) |
| 7b | Int A6 | 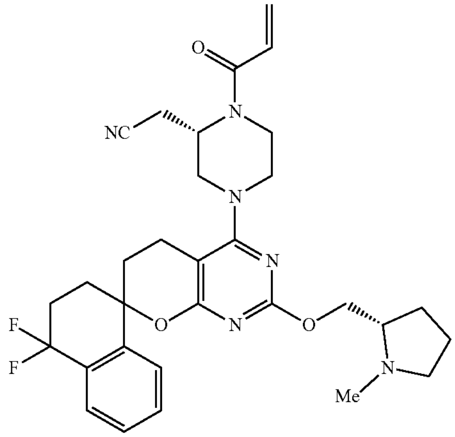 [SMILES: C=CC(=O)N1CCN(c2nc(OC[C@@H]3CCCN3C)nc3c2CCC2(CCC(F)(F)c4ccccc42)O3)C[C@@H]1CC#N] Peak 2 | 2-((2S)-1-acryloyl-4-(4,4-difluoro-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile | | |
| 8 | Int B1 | 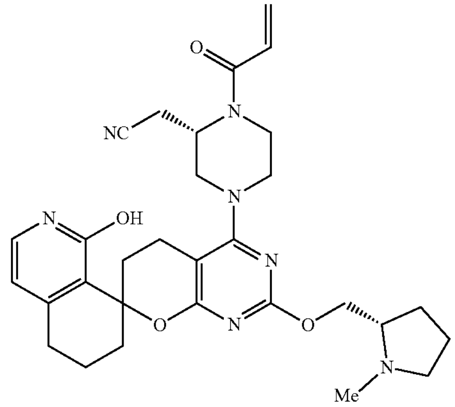 [SMILES: C=CC(=O)N1CCN(c2nc(OC[C@@H]3CCCN3C)nc3c2CCC2(CCCc4ccnc(O)c42)O3)C[C@@H]1CC#N] | 2-((2S)-1-acryloyl-4-(1-hydroxy-2'-(((S)-1-methylpyrrolidin-2-yl)methoxy)-5',6,6',7-tetrahydro-5H-spiro[isoquinoline-8,7'-pyrano[2,3-d]pyrimidin]-4'-yl)piperazin-2-yl)acetonitrile | 560 | N/A Racemate isolated |

-continued

| Ex. | Alkene Precursor | Structure Fraction Collected | Compound Name | $[M + H]^+$ Found | SFC Conditions |
|---|---|---|---|---|---|
| 9a | Int A7 | 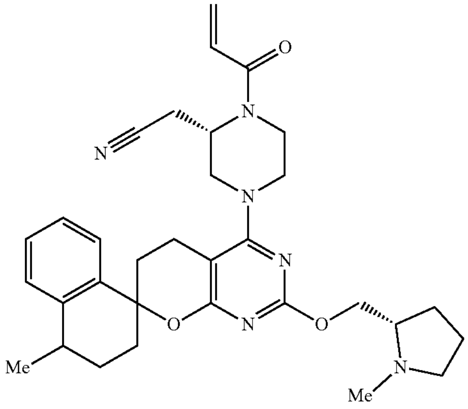 [SMILES: C=CC(=O)N1CCN(c2nc(OC[C@@H]3CCCN3C)nc3c2CCC2(CCC(C)c4ccccc42)O3)C[C@@H]1CC#N] Peak 1 | 2-((2S)-1-acryloyl-4-(4-methyl-2'-(((S)-1-methyl-pyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile | 557 | Column A; Condition: Methanol and 25% Methanol (0.1% $NH_4OH$) |
| 9b | Int A7 | 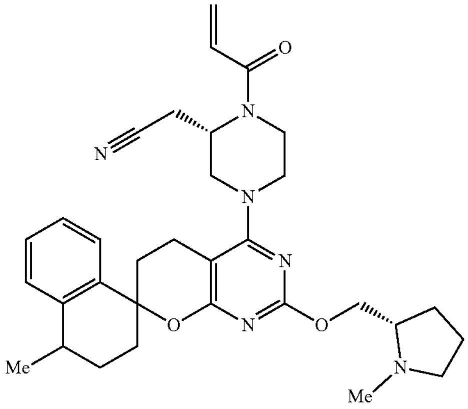 [SMILES: C=CC(=O)N1CCN(c2nc(OC[C@@H]3CCCN3C)nc3c2CCC2(CCC(C)c4ccccc42)O3)C[C@@H]1CC#N] Peak 2 | 2-((2S)-1-acryloyl-4-(4-methyl-2'-(((S)-1-methyl-pyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile | 557 | |
| 9c | Int A7 | 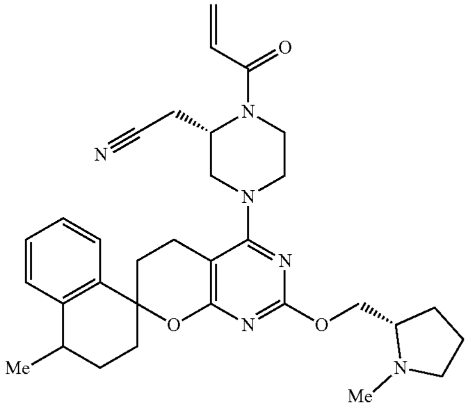 [SMILES: C=CC(=O)N1CCN(c2nc(OC[C@@H]3CCCN3C)nc3c2CCC2(CCC(C)c4ccccc42)O3)C[C@@H]1CC#N] Peak 3, then peak 1 | 2-((2S)-1-acryloyl-4-(4-methyl-2'-(((S)-1-methyl-pyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile | 557 | First Separation: Column A; Condition: Methanol and 25% Methanol (0.1% $NH_4OH$) |

-continued

| Ex. | Alkene Precursor | Structure Fraction Collected | Compound Name | [M + H]+ Found | SFC Conditions |
|---|---|---|---|---|---|
| 9d | Int A7 | 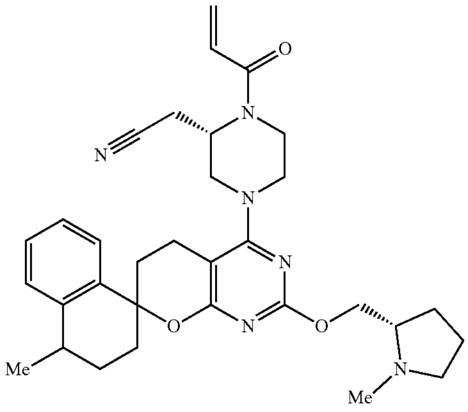 [SMILES: C=CC(=O)N1CCN(c2nc(OC[C@@H]3CCCN3C)nc3c2CCC2(CCC(C)c4ccccc42)O3)C[C@@H]1CC#N] Peak 3 then peak 2 | 2-((2S)-1-acryloyl-4-(4-methyl-2'-(((S)-1-methyl-pyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile | 557 | Second Separation: Column B; Condition: Methanol and 40% Methanol (0.1% $NH_4OH$) |
| 10a | Int A8 | 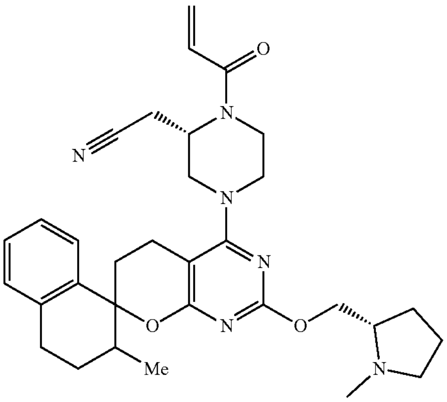 [SMILES: C=CC(=O)N1CCN(c2nc(OC[C@@H]3CCCN3C)nc3c2CCC2(O3)c3ccccc3CCC2C)C[C@@H]1CC#N] Peak 1, then peak 2 | 2-((2S)-1-acryloyl-4-(2-methyl-2'-(((S)-1-methylpyrrolidin-2-yl)methoxy)-3,4,5',6'-tetrahydro-2H-spiro [naphthalene-1,7'-pyrano[2,3-d] pyrimidin]-4'-yl)piperazin-2-yl)acetonitrile | 557 | Separation 1: Column A; Condition: Methanol and 30% Methanol (0.1% $NH_4OH$); Separation 2: Column M; Condition: Methanol and 45% Methanol (0.1% $NH_4OH$); |
| 10b | Int A8 | 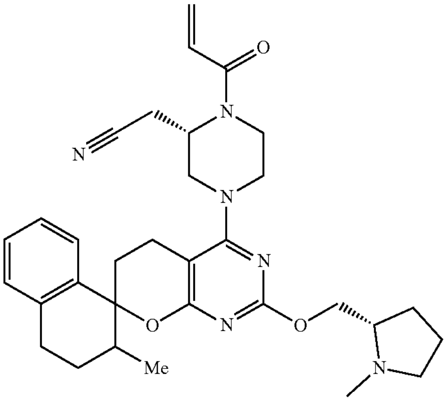 [SMILES: C=CC(=O)N1CCN(c2nc(OC[C@@H]3CCCN3C)nc3c2CCC2(O3)c3ccccc3CCC2C)C[C@@H]1CC#N] Peak 2 | 2-((2S)-1-acryloyl-4-(2-methyl-2'-(((S)-1-methylpyrrolidin-2-yl)methoxy)-3,4,5',6'-tetrahydro-2H-spiro [naphthalene-1,7'-pyrano[2,3-d] pyrimidin]-4'-yl)piperazin-2-yl)acetonitrile | 557 | Column A; Condition: Methanol and 30% Methanol (0.1% $NH_4OH$) |

-continued

| Ex. | Alkene Precursor | Structure Fraction Collected | Compound Name | [M + H]+ Found | SFC Conditions |
|---|---|---|---|---|---|
| 11a | Int A15 | 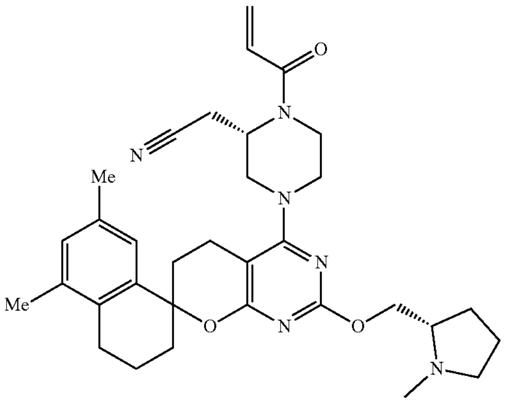 [SMILES: C=CC(=O)N1CCN(c2nc(OC[C@@H]3CCCN3C)nc3c2CCC2(CCCc4c(C)cc(C)cc42)O3)C[C@@H]1CC#N] Peak 1 | 2-((2S)-1-acryloyl-4-(5,7-dimethyl-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile | 571 | Column A; Condition: Methanol and 35% Methanol (0.1% $NH_4OH$) |
| 11b | Int A15 | 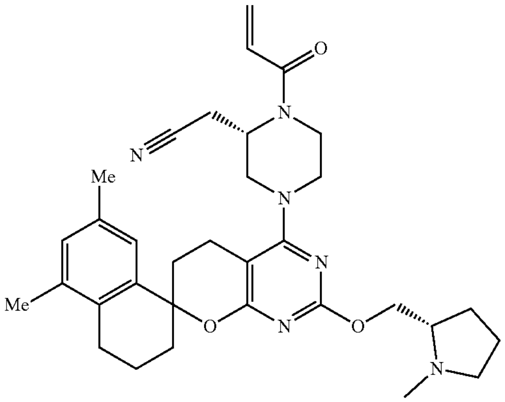 [SMILES: C=CC(=O)N1CCN(c2nc(OC[C@@H]3CCCN3C)nc3c2CCC2(CCCc4c(C)cc(C)cc42)O3)C[C@@H]1CC#N] Peak 2 | 2-((2S)-1-acryloyl-4-(5,7-dimethyl-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile | 571 | |
| 12a | Int A1 | 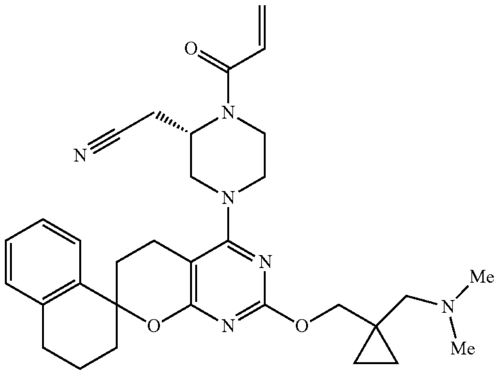 [SMILES: C=CC(=O)N1CCN(c2nc(OCC3(CN(C)C)CC3)nc3c2CCC2(CCCc4ccccc42)O3)C[C@@H]1CC#N] Peak 1 | 2-((2S)-1-acryloyl-4-(2'-((1-((dimethylamino) methyl) cyclopropyl) methoxy)-3,4,5',6'-tetrahydro-2H-spiro [naphthalene-1,7'-pyrano[2,3-d]pyrimidin]-4'-yl)piperazin-2-yl)acetonitrile | 557 | Column A; Condition: Methanol and 30% Methanol/ $CH_3CN$ (0.1% $NH_4OH$) |

-continued

| Ex. | Alkene Precursor | Structure Fraction Collected | Compound Name | [M + H]+ Found | SFC Conditions |
|---|---|---|---|---|---|
| 12b | Int A1 | 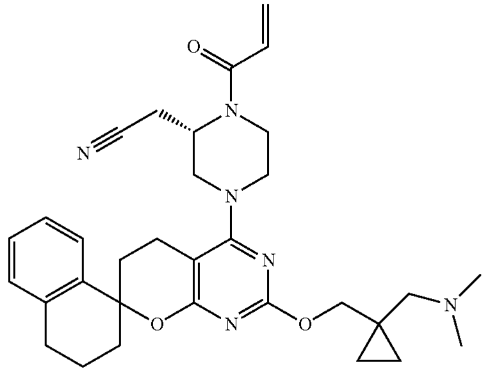 [SMILES: C=CC(=O)N1CCN(c2nc(OCC3(CN(C)C)CC3)nc3c2CCC2(CCCc4ccccc42)O3)C[C@@H]1CC#N] Peak 2 | 2-((2S)-1-acryloyl-4-(2'-((1-((dimethylamino)methyl)cyclopropyl)methoxy)-3,4,5',6'-tetrahydro-2H-spiro[naphthalene-1,7'-pyrano[2,3-d]pyrimidin]-4'-yl)piperazin-2-yl)acetonitrile | 557 | |

Example 13a: 1-((3S)-3-methyl-4-(2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-1-yl)prop-2-en-1-one

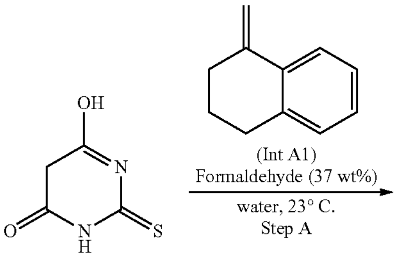

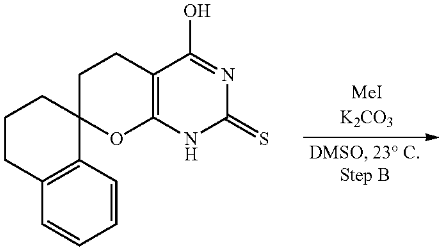

Int 13a

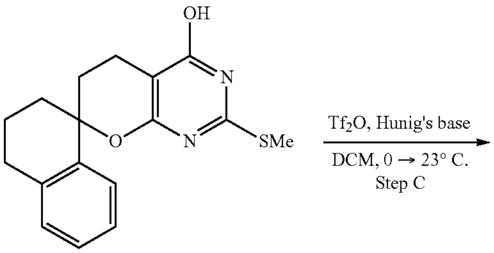

Int 13b

-continued

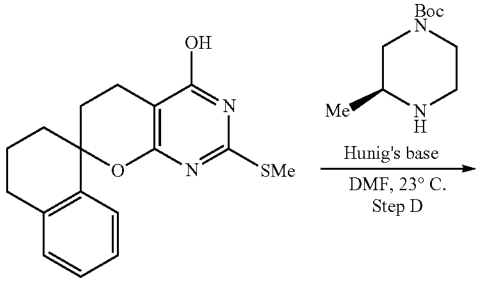

Int 13c

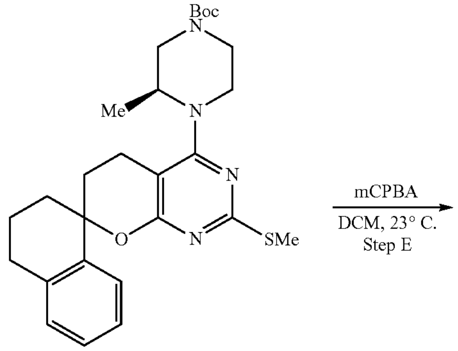

Int 13d

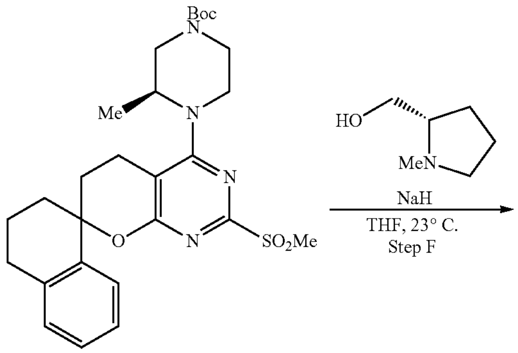

Int 13e

-continued

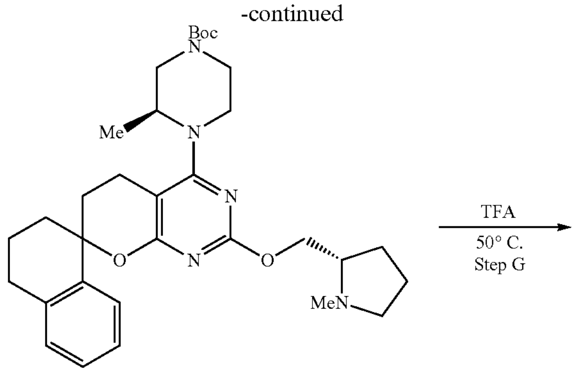

Int 13f

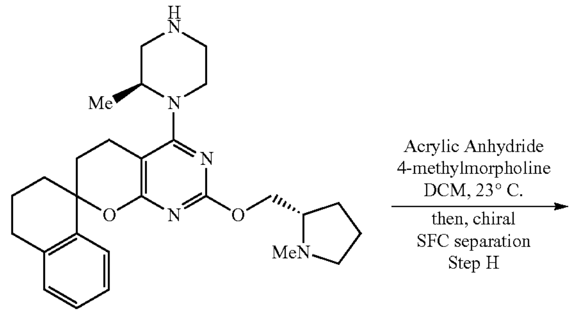

Int 13g

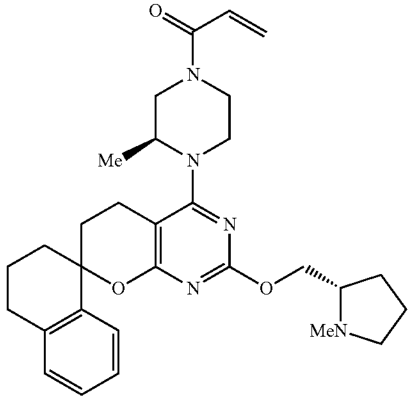

Ex. 13a

Step A: 4'-hydroxy-3,4,5',6'-tetrahydro-2H-spiro [naphthalene-1,7'-pyrano[2,3-d]pyrimidine]-2'($1^1$H)-thione (Int 13a)

To a mixture of 1-methylene-1,2,3,4-tetrahydronaphthalene (Int A1, 1.0 g, 6.9 mmol), 2-thioxodihydropyrimidine-4,6(1H,5H)-dione (1.50 g, 10.4 mmol) and formaldehyde (37% w/w in water) (1.03 mL, 13.9 mmol) was added water (5.5 mL). The reaction mixture was stirred at room temperature overnight. The suspension was lyophilized overnight to yield 4'-hydroxy-3,4,5',6'-tetrahydro-2H-spiro [naphthalene-1,7'-pyrano[2,3-d]pyrimidine]-2'(1'H)-thione (Int 13a). MS (ESI): $[M+H]^+$ m/z: 301.

Step B: 2'-(methylthio)-3,4,5',6'-tetrahydro-2H-spiro [naphthalene-1,7'-pyrano[2,3-d]pyrimidin]-4'-ol (Int 13b)

To a solution of 4'-hydroxy-3,4,5',6'-tetrahydro-2H-spiro [naphthalene-1,7'-pyrano[2,3-d]pyrimidine]-2'(1'H)-thione (Int 13a) (1.00 g, 3.33 mmol) in DMSO (5 mL) was added $K_2CO_3$ (690 mg, 4.99 mmol). The reaction mixture was stirred at room temperature for 1 h. Iodomethane (0.271 mL, 4.33 mmol) was added and the reaction was stirred until complete product formation was observed. The crude mixture was concentrated and dried under lyophilization to yield 2'-(methylthio)-3,4,5',6'-tetrahydro-2H-spiro[naphthalene-1,7'-pyrano[2,3-d]pyrimidin]-4'-ol (Int 13b). MS (ESI): $[M+H]^+$ m/z: 315.

Step C: 2'-(methylthio)-3,4,5',6'-tetrahydro-2H-spiro [naphthalene-1,7'-pyrano[2,3-d]pyrimidin]-4'-yl trifluoromethanesulfonate (Int 13c)

To a 0° C. cooled solution of 2'-(methylthio)-3,4,5',6'-tetrahydro-2H-spiro[naphthalene-1,7'-pyrano[2,3-d]pyrimidin]-4'-ol (Int 13b) (250 mg, 0.80 mmol) in DCM (7.5 mL) was added Hunig's Base (0.56 mL, 3.2 mmol), followed by trifluoromethanesulfonic anhydride (0.50 mL, 2.39 mmol). The reaction mixture was stirred at room temperature for 5 h. The reaction mixture was then diluted with 5 mL of DCM, washed with saturated aqueous $NaHCO_3$ solution, followed by brine and then concentrated. The crude material was purified by silica gel column (24 g) using 20% EtOAc in hexane to yield 2'-(methylthio)-3,4,5',6'-tetrahydro-2H-spiro [naphthalene-1,7'-pyrano[2,3-d]pyrimidin]-4'-yl trifluoromethanesulfonate (Int 13c). MS (ESI): $[M+H]^+$ m/z: 447.

Step D: tert-butyl (3S)-3-methyl-4-(2'-(methylthio)-3,4,5',6'-tetrahydro-2H-spiro[naphthalene-1,7'-pyrano[2,3-d]pyrimidin]-4'-yl)piperazine-1-carboxylate (Int 13d)

To solution of 2'-(methylthio)-3,4,5',6'-tetrahydro-2H-spiro[naphthalene-1,7'-pyrano[2,3-d]pyrimidin]-4'-yl trifluoromethanesulfonate (Int 13c) (172 mg, 0.385 mmol) in DMF (3 mL) were added tert-butyl (S)-3-methylpiperazine-1-carboxylate (116 mg, 0.578 mmol) followed by Hunig's Base (0.135 mL, 0.771 mmol). The reaction mixture was stirred at room temperature for 4 h and then heated to 50° C. The reaction mixture was then quenched with water and extracted with EtOAc. The combined organic layers were concentrated and purified by silica gel column (24 g), eluting from 5-20% EtOAc in hexane to yield tert-butyl (3S)-3-methyl-4-(2'-(methylthio)-3,4,5',6'-tetrahydro-2H-spiro [naphthalene-1,7'-pyrano[2,3-d]pyrimidin]-4'-yl)piperazine-1-carboxylate (Int 13d). MS (ESI): $[M+H]^+$ m/z: 497.

Step E: tert-butyl (3S)-3-methyl-4-(2'-(methylsulfonyl)-3,4,5',6'-tetrahydro-2H-spiro[naphthalene-1,7'-pyrano[2,3-d]pyrimidin]-4'-yl)piperazine-1-carboxylate (Int 13e)

To a solution of tert-butyl (3S)-3-methyl-4-(2'-(methylthio)-3,4,5',6'-tetrahydro-2H-spiro[naphthalene-1,7'-pyrano [2,3-d]pyrimidin]-4'-yl)piperazine-1-carboxylate (Int 13d) (100 mg, 0.20 mmol) in DCM (2 mL) was added mCPBA (104 mg, 0.604 mmol). The reaction mixture was stirred at room temperature for 3 h. The reaction mixture was then filtered and the filtrate was washed with saturated aqueous $NaHCO_3$ and concentrated to yield tert-butyl (3S)-3-methyl-4-(2'-(methylsulfonyl)-3,4,5',6'-tetrahydro-2H-spiro[naphthalene-1,7'-pyrano[2,3-d]pyrimidin]-4'-yl)piperazine-1-carboxylate (Int 13e). MS (ESI): $[M+H]^+$ m/z: 529.

Step F: tert-butyl (3S)-3-methyl-4-(2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazine-1-carboxylate (Int 13f)

NaH (21.79 mg, 0.545 mmol), tert-butyl (3S)-3-methyl-4-(2'-(methylsulfonyl)-3,4,5',6'-tetrahydro-2H-spiro[naphthalene-1,7'-pyrano[2,3-d]pyrimidin]-4'-yl)piperazine-1-carboxylate (Int 13e) (96 mg, 0.182 mmol), and (S)-(1-methylpyrrolidin-2-yl)methanol (64.8 μL, 0.545 mmol) were combined under nitrogen. To this was added THF (1.75 mL). The reaction mixture was stirred at room temperature for 55 min and then diluted with methanol and concentrated. The product was purified on a 24 g silica gel column eluting with 40% EtOAc in hexane to yield tert-butyl (3S)-3-methyl-4-(2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazine-1-carboxylate (Int 13f). MS (ESI): $[M+H]^+$ m/z: 564.

Step G: 4'-((S)-2-methylpiperazin-1-yl)-2'-(((S)-1-methylpyrrolidin-2-yl)methoxy)-3,4,5',6'-tetrahydro-2H-spiro[naphthalene-1,7'-pyrano[2,3-d]pyrimidine] (Int 13g)

A mixture of tert-butyl (3S)-3-methyl-4-(2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazine-1-carboxylate (Int 13f) (71 mg, 0.126 mmol) and TFA (146 μl, 1.889 mmol) was heated at 50° C. for 3 h. The crude mixture was concentrated and re-dissolved in 5 mL DCM and neutralized with saturated, aqueous $NaHCO_3$. The organic layer was separated and concentrated to yield 4'-((S)-2-methylpiperazin-1-yl)-2'-(((S)-1-methylpyrrolidin-2-yl)methoxy)-3,4,5',6'-tetrahydro-2H-spiro[naphthalene-1,7'-pyrano[2,3-d]pyrimidine](Int 13g). MS (ESI): $[M+H]^+$ m/z: 464.

Step H: 1-((3S)-3-methyl-4-(2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-1-yl)prop-2-en-1-one (Ex. 13a)

To a mixture of 4'-((S)-2-methylpiperazin-1-yl)-2'-(((S)-1-methylpyrrolidin-2-yl)methoxy)-3,4,5',6'-tetrahydro-2H-spiro[naphthalene-1,7'-pyrano[2,3-d]pyrimidine](Int 13g) (60 mg, 0.129 mmol) in DCM (1200 μl) were added 4-methylmorpholine (43 μl, 0.39 mmol) followed by acrylic anhydride (18 μl, 0.16 mmol). The reaction mixture was stirred at room temperature for 1 h. 5 mL DCM was then added to the crude mixture, followed by saturated, aqueous $NaHCO_3$. The organic layer was separated and concentrated. The crude mixture was purified on a 12 g silica gel column with 10% of methanol in DCM. The racemic material was collected, concentrated, and resolved by SFC (Column C; $CH_3CN$ and 25% MeOH (with 0.1% $NH_4OH$)) to provide 1-((3S)-3-methyl-4-(2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-1-yl)prop-2-en-1-one; Peak 1 (Ex. 13a) MS (ESI): $[M+H]^+$ m/z: 518; $^1H$ NMR (499 MHz, DMSO-d6) δ 7.44-7.34 (m, 1H), 7.23 (td, J=7.0, 1.5 Hz, 2H), 7.19-7.12 (m, 1H), 6.84 (ddd, J=34.8, 16.5, 10.7 Hz, 1H), 6.22-6.10 (m, 1H), 5.72 (dd, J=10.4, 2.3 Hz, 1H), 4.46-4.09 (m, 3H), 4.09-3.80 (m, 3H), 3.50-3.25 (m, 3H), 3.23-2.98 (m, 1H), 2.98-2.71 (m, 5H), 2.38 (d, J=13.8 Hz, 1H), 2.32 (s, 3H), 2.16 (q, J=8.8 Hz, 1H), 2.07 (d, J=10.2 Hz, 1H), 2.04-1.88 (m, 2H), 1.88-1.77 (m, 2H), 1.66 (tq, J=8.3, 4.7, 3.9 Hz, 2H), 1.55 (dq, J=13.5, 6.6 Hz, 1H), 1.25 (t, J=6.8 Hz, 3H).

Example 14a was prepared using procedures similar to those described in Example 13a. In Step D, tert-butyl (R)-2-methylpiperazine-1-carboxylate was reacted with Int 13c.

| Ex. | Structure | Compound Name | $[M + H]^+$ Found | Purification Conditions |
|---|---|---|---|---|
| 14a | 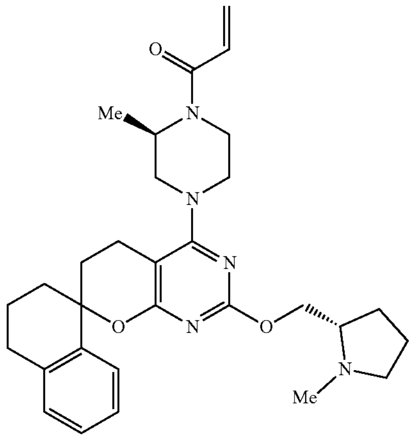 [SMILES: C=CC(=O)N1CCN(c2nc(OC[C@@H]3CCCN3C)nc3c2CCC2(CCCc4ccccc42)O3)C[C@H]1C] Peak 1 | 1-((2R)-2-methyl-4-(2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-1-yl)prop-2-en-1-one | 518 | Column D; Condition: water (0.1% TFA)-MeCN |

Example 15a/b: 2-((2S)-1-acryloyl-4-(2'-(((S)-1-ethylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile

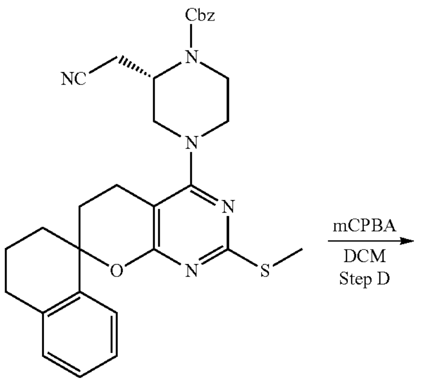

Int 18c

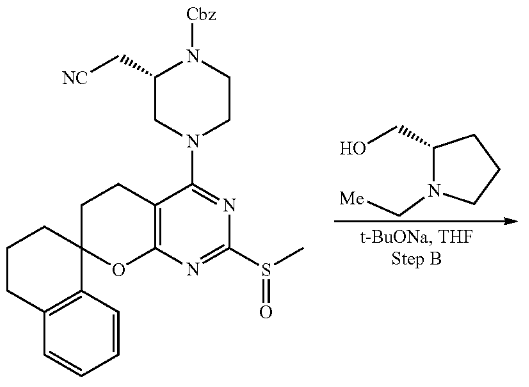

Int 15a

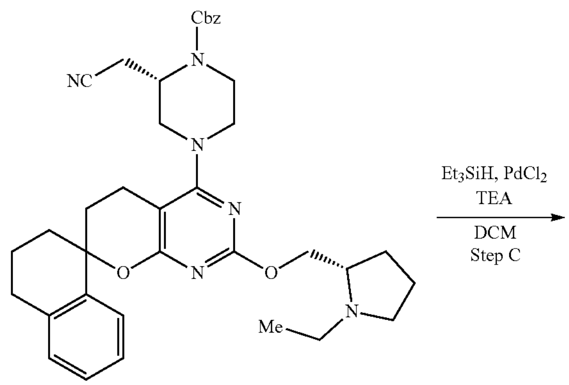

Int 15b

-continued

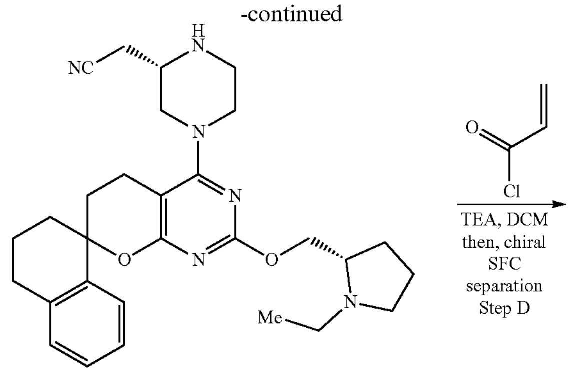

Int 15c

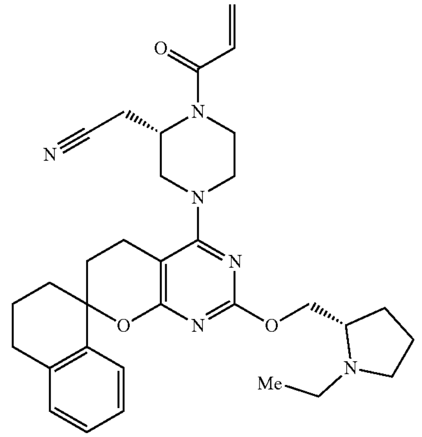

Ex 15a
Ex 15b

Step A: benzyl (2S)-2-(cyanomethyl)-4-(2'-(methylsulfinyl)-3,4,5',6'-tetrahydro-2H-spiro[naphthalene-1,7'-pyrano[2,3-d]pyrimidin]-4'-yl)piperazine-1-carboxylate (Int 15a)

A mixture of (2S)-benzyl 2-(cyanomethyl)-4-(2'-(methylthio)-3,4,5',6'-tetrahydro-2H-spiro[naphthalene-1,7'-pyrano[2,3-d]pyrimidin]-4'-yl)piperazine-1-carboxylate (Int 18c, 600 mg, 1.1 mmol) and m-CPBA (303 mg, 1.40 mmol) in DCM (10 mL) was stirred at 25° C. for 3 h to give a light yellow mixture. The mixture was concentrated in vacuum, and the residue was purified by preparative TLC (silica gel, ethyl acetate) to yield benzyl (2S)-2-(cyanomethyl)-4-(2'-(methylsulfinyl)-3,4,5',6'-tetrahydro-2H-spiro[naphthalene-1,7'-pyrano[2,3-d]pyrimidin]-4'-yl)piperazine-1-carboxylate (Int 15a). MS (ESI): $[M+H]^+$ m/z: 572.

Step B: benzyl (2S)-2-(cyanomethyl)-4-(2'-(((S)-1-ethylpyrrolidin-2-yl)methoxy)-3,4,5',6'-tetrahydro-2H-spiro[naphthalene-1,7'-pyrano[2,3-d]pyrimidin]-4'-yl)piperazine-1-carboxylate (Int 15b)

To a solution of (S)-(1-ethylpyrrolidin-2-yl)methanol (208 mg, 1.609 mmol) in THF (3.0 mL) was added sodium 2-methylpropan-2-olate (0.402 mL, 0.805 mmol) (2 M in THF) at 0° C. under $N_2$ atmosphere. Then benzyl (2S)-2-(cyanomethyl)-4-(2'-(methylsulfinyl)-3,4,5',6'-tetrahydro-2H-spiro[naphthalene-1,7'-pyrano[2,3-d]pyrimidin]-4'-yl)piperazine-1-carboxylate (Int 15a) (230 mg, 0.402 mmol) in THF (3.00 mL) was added. The mixture was stirred at 0° C.

for 0.5 h. The reaction mixture was quenched with water (10 mL) and extracted with EtOAc (10 mL×3). The combined organic phases were washed with brine (30 mL), dried over anhydrous $Na_2SO_4$, filtered and concentrated under reduced pressure to yield crude benzyl (2S)-2-(cyanomethyl)-4-(2'-(((S)-1-ethylpyrrolidin-2-yl)methoxy)-3,4,5',6'-tetrahydro-2H-spiro[naphthalene-1,7'-pyrano[2,3-d]pyrimidin]-4'-yl) piperazine-1-carboxylate (Int 15b), which was used directly without further purification. MS (ESI): $[M+H]^+$ m/z: 637.

Step C: 2-((2S)-4-(2'-(((S)-1-ethylpyrrolidin-2-yl) methoxy)-3,4,5',6'-tetrahydro-2H-spiro[naphthalene-1,7'-pyrano[2,3-d]pyrimidin]-4'-yl)piperazin-2-yl) acetonitrile (Int 15c)

To a stirred mixture of benzyl (2S)-2-(cyanomethyl)-4-(2'-(((S)-1-ethylpyrrolidin-2-yl)methoxy)-3,4,5',6'-tetrahydro-2H-spiro[naphthalene-1,7'-pyrano[2,3-d]pyrimidin]-4'-yl)piperazine-1-carboxylate (Int 15b) (20 mg, 0.031 mmol) in DCM (5 mL) was added palladium(II) chloride (0.557 mg, 3.14 μmol), $Et_3N$ (0.026 mL, 0.188 mmol) and triethylsilane (0.130 mL, 0.817 mmol), and then the mixture was stirred at 25° C. for 1 h. The mixture was quenched with MeOH (2 mL), filtered and the filtrate was concentrated in vacuo. The residue was purified by preparative HPLC (Column: YMC-Actus Triart C18 100 mm×30 mm×5 um; Condition: water (0.1% TFA)-ACN Begin B 25; End B 55 Gradient Time (min): 11; 100% B Hold Time (min): 1.1; FlowRate (mL/min) 40) to afford 2-((2S)-4-(2'-(((S)-1-ethylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile (Int 15c). MS (ESI): $[M+H]^+$ m/z: 503.

Step D: 2-((2S)-1-acryloyl-4-(2'-(((S)-1-ethylpyrrolidin-2-yl)methoxy)-3,4,5',6'-tetrahydro-2H-spiro[naphthalene-1,7'-pyrano[2,3-d]pyrimidin]-4'-yl) piperazin-2-yl)acetonitrile (Ex 15a/15b)

To a stirred mixture of 2-((2S)-4-(2'-(((S)-1-ethylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile (Int 15c) (180 mg, 0.358 mmol) in DCM (5 mL) was added TEA (0.15 mL, 1.07 mmol) and acryloyl chloride (49 mg, 0.54 mmol) at 0° C. After addition, the mixture was stirred at 0° C. for 15 min. The mixture was quenched with MeOH (2 mL), filtered and the filtrate was concentrated in vacuo. The residue was purified by Prep-HPLC (Column: Agela DuraShell C18 150 mm×25 mm, 5 um; Condition: water (0.04% $NH_3H_2O$+10 mM $NH_4HCO_3$)-ACN Begin B, 42 End B 72; Gradient Time (min): 10; 100% B Hold Time (min): 2; FlowRate (mL/min) 25). The racemic mixture was separated by preparative SFC (Column E; Condition: 0.1% $NH_3H_2O$ EtOH to give 2-((2S)-1-acryloyl-4-(2'-(((S)-1-ethylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile; Peak 1 (Ex 15a). MS (ESI): $[M+H]^+$ m/z: 557. $^1$H NMR (500 MHz, METHANOL-$d_4$) δ 7.48-7.41 (m, 1H), 7.27-7.19 (m, 2H), 7.19-7.14 (m, 1H), 6.95-6.78 (m, 1H), 6.31 (br d, J=17.0 Hz, 1H), 5.85 (br d, J=9.5 Hz, 1H), 4.45-4.25 (m, 2H), 4.20-3.63 (m, 3H), 3.54-3.35 (m, 2H), 3.32-3.01 (m, 5H), 2.99-2.78 (m, 5H), 2.67 (br d, J=15.5 Hz, 1H), 2.61-2.27 (m, 2H), 2.25-2.04 (m, 5H), 2.02-1.81 (m, 4H), 1.77 (br s, 1H), 1.20 (br t, J=7.0 Hz, 3H). And 2-((2S)-1-acryloyl-4-(2'-(((S)-1-ethylpyrrolidin-2-yl) methoxy)-3,4,5',6'-tetrahydro-2H-spiro[naphthalene-1,7'-pyrano[2,3-d]pyrimidin]-4'-yl)piperazin-2-yl)acetonitrile; Peak 2 (Ex. 15b). MS (ESI): $[M+H]^+$ m/z: 557. $^1$H NMR (500 MHz, METHANOL-$d_4$) δ 7.42 (br d, J=8.5 Hz, 1H), 7.23 (br t, J=5.5 Hz, 2H), 7.17 (br d, J=8.0 Hz, 1H), 6.95-6.78 (m, 1H), 6.31 (br d, J=16.5 Hz, 1H), 5.86 (br d, J=10.2 Hz, 1H), 4.37 (br d, J=5.2 Hz, 2H), 4.29-3.93 (m, 3H), 3.49 (br d, J=19.7 Hz, 2H), 3.31-3.04 (m, 6H), 2.98-2.76 (m, 4H), 2.70-2.46 (m, 3H), 2.24-2.12 (m, 5H), 2.04-1.90 (m, 4H), 1.81 (br d, J=6.9 Hz, 1H), 1.21 (br t, J=7.2 Hz, 3H).

Using procedures similar to Example 15, Examples 16a and 16b were prepared. The difluorosubstituted —Y—Z precursor was purchased from CombiBlocks.

| Ex. | Structure | Compound Name | $[M + H]^+$ Found | Purification Conditions |
|---|---|---|---|---|
| 16a | 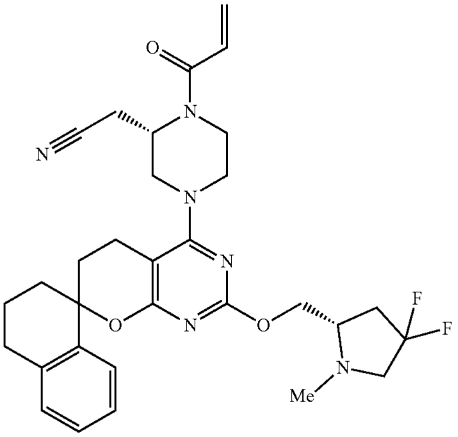 [SMILES: C=CC(=O)N1CCN(c2nc(OC[C@@H]3CC(F)(F)CN3C)nc3c2CCC2(CCCc4ccccc42)O3)C[C@@H]1CC#N] Peak 1 | 2-((2S)-1-acryloyl-4-(2'-(((S)-4,4-difluoro-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile | 579 | Column D; Condition: water (0.05% $NH_4OH$ 10 mM $NH_4HCO_3$)—$CH_3CN$ |

-continued

| Ex. | Structure | Compound Name | [M + H]+ Found | Purification Conditions |
|---|---|---|---|---|
| 16b | 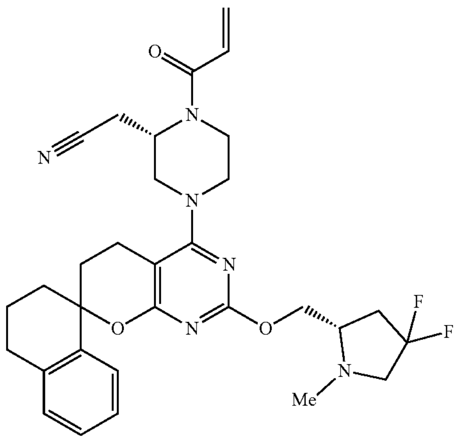 [SMILES: C=CC(=O)N1CCN(c2nc(OC[C@@H]3CC(F)(F)CN3C)nc3c2CCC2(CCCc4ccccc42)O3)C[C@@H]1CC#N] Peak 2 | 2-((2S)-1-acryloyl-4-(2'-(((S)-4,4-difluoro-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile | 579 | |

Example 17a: 2-((2S)-1-(2-fluoroacryloyl)-4-(2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile

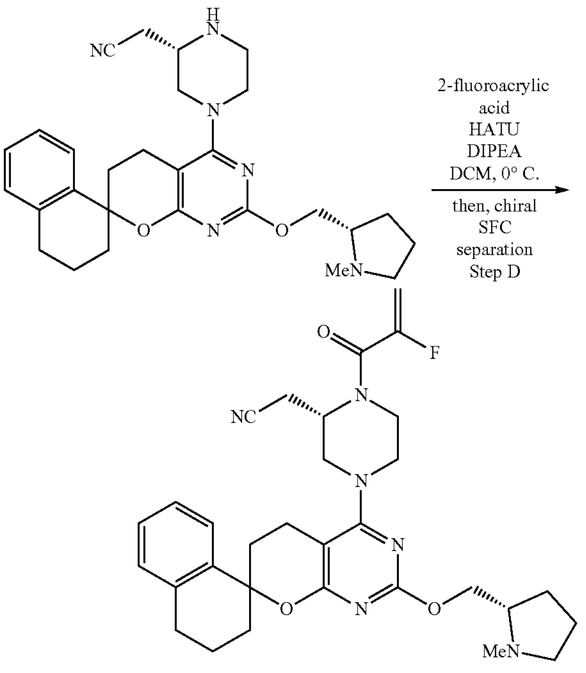

Ex 17a

To a solution of 2-((2S)-4-(2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile (114 mg, 0.233 mmol)) in DCM (850 μl) was added 2-fluoroacrylic acid (63.0 mg, 0.700 mmol)), DIPEA (244 μl, 1.400 mmol) and HATU (266 mg, 0.700 mmol) under nitrogen. The reaction mixture was stirred at 0° C. for 30 min and then diluted with DCM, washed with brine and concentrated. The crude residue was purified by 24 g silica gel column with 20% of methanol in DCM. The racemic material was collected, concentrated, and resolved by SFC (Column E; MeOH and 30% MeOH (with 0.1% $NH_4OH$)) to provide 2-((2S)-1-(2-fluoroacryloyl)-4-(2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-2-yl)acetonitrile; Peak 1 (Ex. 17a) MS (ESI): $[M+H]^+$ m/z: 561.3; $^1H$ NMR (499 MHz, DMSO-d6) δ 10.10 (s, 1H), 7.42-7.37 (m, 1H), 7.30-7.21 (m, 2H), 7.17 (d, J=6.9 Hz, 1H), 5.40 (dd, J=18.0, 4.1 Hz, 1H), 5.29 (d, J=50.7 Hz, 1H), 4.86 (s, 1H), 4.40 (s, 2H), 3.95 (dd, J=53.6, 13.3 Hz, 3H), 3.47 (s, 3H), 3.27 (d, J=11.2 Hz, 7H), 3.11 (s, 2H), 3.03-2.69 (m, 9H), 2.64 (d, J=12.2 Hz, 2H), 2.26-1.60 (m, 11H).

Example 18b: 4'-((S)-4-acryloyl-3-(cyanomethyl)piperazin-1-yl)-3,4,5',6'-tetrahydro-2H-spiro[naphthalene-1,7'-pyrano[2,3-d]pyrimidine]-2'-carboxamide

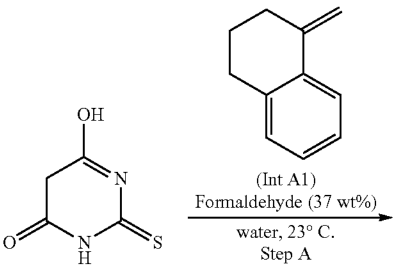

-continued
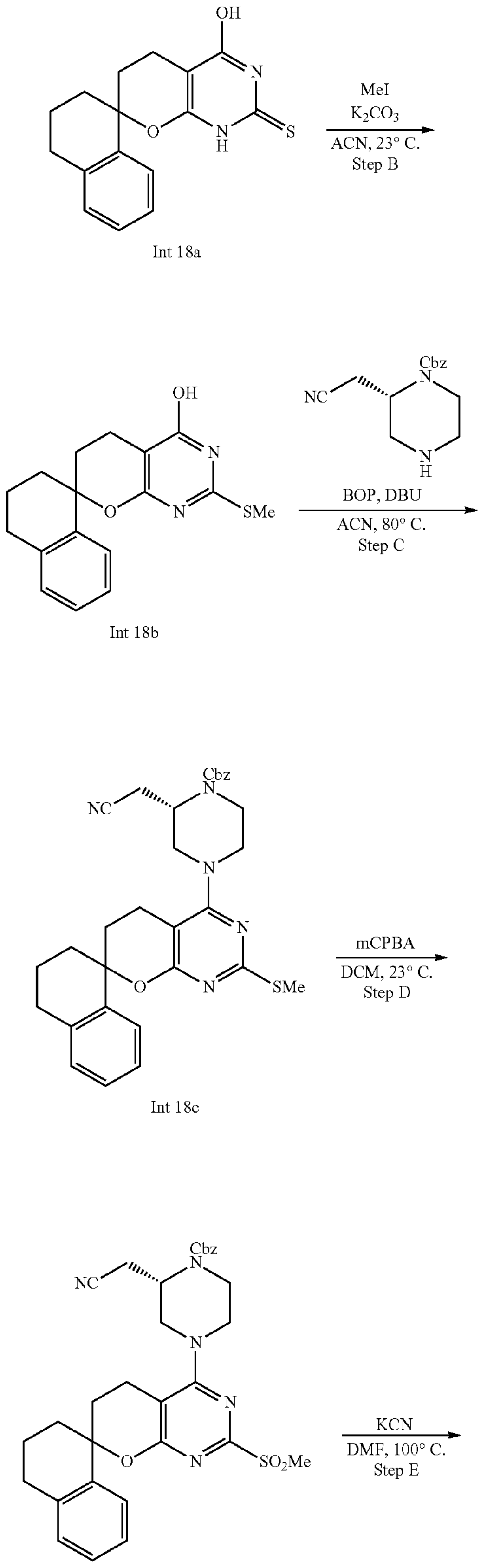
Int 18a
Int 18b
Int 18c
Int 18d
-continued
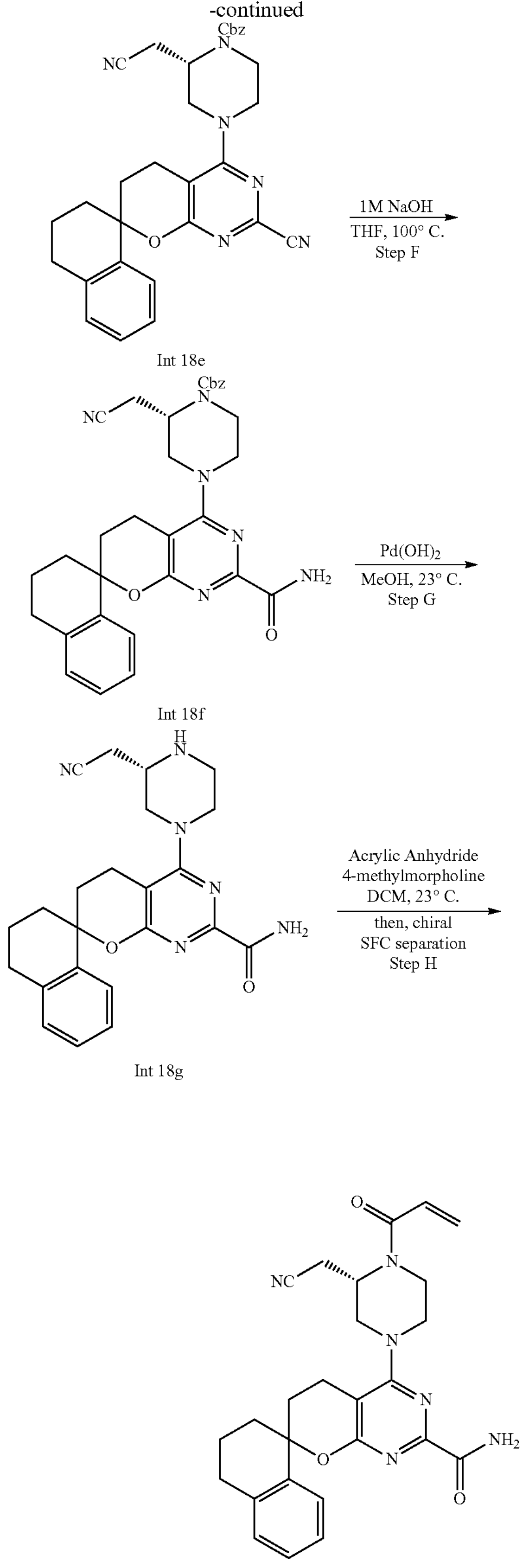
Int 18e
Int 18f
Int 18g
Ex. 18a
Ex. 18b Step A: 2'-thioxo-2',3,3',4,5',6'-hexahydro-2H-spiro[naphthalene-1,7'-pyrano[2,3-d]pyrimidin]-4'(1'H)-one (Int 18a)

To a mixture of 1-methylene-1,2,3,4-tetrahydronaphthalene (Int A1, 3.00 g, 20.8 mmol), 2-thioxodihydropyrimidine-4,6(1H,5H)-dione (4498 mg, 31.2 mmol) and formaldehyde (37% in $H_2O$) (3.10 mL, 41.6 mmol) was added water (16.5 mL). The reaction mixture was stirred at room temperature for 4 h. The suspension was lyophilized overnight to yield 2'-thioxo-2',3,3',4,5',6'-hexahydro-2H-spiro[naphthalene-1,7'-pyrano[2,3-d]pyrimidin]-4'(1'H)-one (Int 18a). MS (ESI): $[M+H]^+$ m/z: 301.

Step B: 2'-(methylthio)-3,4,5',6'-tetrahydro-2H-spiro[naphthalene-1,7'-pyrano[2,3-d]pyrimidin]-4'(3'H)-one (Int 18b)

To a solution of 2'-thioxo-2',3,3',4,5',6'-hexahydro-2H-spiro[naphthalene-1,7'-pyrano[2,3-d]pyrimidin]-4'(1'H)-one (Int 18a) (2.50 g, 8.32 mmol) in acetonitrile (45 mL) was added $K_2CO_3$ (1.73 g, 12.5 mmol). The reaction was stirred at room temperature for 1 h and iodomethane (0.677 mL, 10.8 mmol) was added. The reaction mixture was then stirred at room temperature over the weekend. The reaction mixture was filtered and the solid collected was dried under vacuum to yield 2'-(methylthio)-3,4,5',6'-tetrahydro-2H-spiro[naphthalene-1,7'-pyrano[2,3-d]pyrimidin]-4'(3'H)-one (Int 18b). MS (ESI): $[M+H]^+$ m/z: 315.

Step C: benzyl (2S)-2-(cyanomethyl)-4-(2'-(methylthio)-3,4,5',6'-tetrahydro-2H-spiro[naphthalene-1,7'-pyrano[2,3-d]pyrimidin]-4'-yl)piperazine-1-carboxylate (Int 18c)

To a solution of 2'-(methylthio)-3,4,5',6'-tetrahydro-2H-spiro[naphthalene-1,7'-pyrano[2,3-d]pyrimidin]-4'(3'H)-one (Int 18b) (1.50 g, 4.77 mmol) in acetonitrile (22 mL) was added benzyl (S)-2-(cyanomethyl)piperazine-1-carboxylate (2.47 g, 9.54 mmol), BOP (2.74 g, 6.20 mmol) followed by DBU (2.18 mL, 14.3 mmol). The resulting mixture was heated at 80° C. overnight. The reaction mixture was quenched with water (5 mL) and extracted with EtOAc (3×5 mL). The combined organic layers were concentrated and purified using 24 g silica gel column with 30% of EtOAc in hexanes to yield benzyl (2S)-2-(cyanomethyl)-4-(2'-(methylthio)-3,4,5',6'-tetrahydro-2H-spiro[naphthalene-1,7'-pyrano[2,3-d]pyrimidin]-4'-yl)piperazine-1-carboxylate (Int 18c). MS (ESI): $[M+H]^+$ m/z: 556.

Step D: benzyl (2S)-2-(cyanomethyl)-4-(2'-(methylsulfonyl)-3,4,5',6'-tetrahydro-2H-spiro[naphthalene-1,7'-pyrano[2,3-d]pyrimidin]-4'-yl)piperazine-1-carboxylate (Int 18d)

A mixture of benzyl (2S)-2-(cyanomethyl)-4-(2'-(methylthio)-3,4,5',6'-tetrahydro-2H-spiro[naphthalene-1,7'-pyrano[2,3-d]pyrimidin]-4'-yl)piperazine-1-carboxylate (Int 18c) (1.25 g, 2.25 mmol) and 3-chlorobenzoperoxoic acid (1.17 g, 6.75 mmol) in DCM (20 mL) was stirred at room temperature for 3 h. The reaction mixture was diluted with DCM, filtered and the filtrate was washed with saturated, aqueous $NaHCO_3$ solution. The combined organic layers were concentrated to yield benzyl (2S)-2-(cyanomethyl)-4-(2'-(methylsulfonyl)-3,4,5',6'-tetrahydro-2H-spiro[naphthalene-1,7'-pyrano[2,3-d]pyrimidin]-4'-yl)piperazine-1-carboxylate (Int 18d). MS (ESI): $[M+H]^+$ m/z: 588.

Step E: benzyl (2S)-4-(2'-cyano-3,4,5',6'-tetrahydro-2H-spiro[naphthalene-1,7'-pyrano[2,3-d]pyrimidin]-4'-yl)-2-(cyanomethyl)piperazine-1-carboxylate (Int 18e)

To a mixture of benzyl (2S)-2-(cyanomethyl)-4-(2'-(methylsulfonyl)-3,4,5',6'-tetrahydro-2H-spiro[naphthalene-1,7'-pyrano[2,3-d]pyrimidin]-4'-yl)piperazine-1-carboxylate (Int 18d) (1.20 g, 2.04 mmol) in DMF (18 mL) was added KCN (266 mg, 4.08 mmol) and heated at 100° C. for overnight. The reaction mixture was cooled to room temperature, quenched with 5 mL of water, and extracted with EtOAc (3×10 mL). The combined organic layers were washed with brine solution and concentrated. The crude material was purified by 12 g silica gel column with 45% of EtOAc in Hexanes to yield benzyl (2S)-4-(2'-cyano-3,4,5',6'-tetrahydro-2H-spiro[naphthalene-1,7'-pyrano[2,3-d]pyrimidin]-4'-yl)-2-(cyanomethyl)piperazine-1-carboxylate (Int 18e). MS (ESI): $[M+H]^+$ m/z: 535.

Step F: benzyl (2S)-4-(2'-carbamoyl-3,4,5',6'-tetrahydro-2H-spiro[naphthalene-1,7'-pyrano[2,3-d]pyrimidin]-4'-yl)-2-(cyanomethyl)piperazine-1-carboxylate (Int 18f)

A microwave vial was charged with benzyl (2S)-4-(2'-cyano-3,4,5',6'-tetrahydro-2H-spiro[naphthalene-1,7'-pyrano[2,3-d]pyrimidin]-4'-yl)-2-(cyanomethyl)piperazine-1-carboxylate (Int 18e) (700 mg, 1.31 mmol) in THF (13 mL) and added 1M NaOH (13.1 mL, 13.1 mmol). It was then heated at 100° C. for 4 h. The reaction mixture was acidified with 1 N HCl and extracted with ethyl acetate. The combined organic layers were washed with saturated brine solution and concentrated to yield benzyl (2S)-4-(2'-carbamoyl-3,4,5',6'-tetrahydro-2H-spiro[naphthalene-1,7'-pyrano[2,3-d]pyrimidin]-4'-yl)-2-(cyanomethyl)piperazine-1-carboxylate (Int 18f). MS (ESI): $[M+H]^+$ m/z: 553.

Step G: 4'-((S)-3-(cyanomethyl)piperazin-1-yl)-3,4,5',6'-tetrahydro-2H-spiro[naphthalene-1,7'-pyrano[2,3-d]pyrimidine]-2'-carboxamide (Int 18g)

A vial was charged with Pd/C ((57.8 mg, 0.054 mmol) and benzyl (2S)-4-(2'-carbamoyl-3,4,5',6'-tetrahydro-2H-spiro[naphthalene-1,7'-pyrano[2,3-d]pyrimidin]-4'-yl)-2-(cyanomethyl)piperazine-1-carboxylate (Int 18f) (150 mg, 0.271 mmol) in MeOH (3000 μl) was added under nitrogen. The reaction mixture was degassed with vacuum and back filled with nitrogen three times and stirred under hydrogen balloon at room temperature for 4 h. The reaction mixture was filtered over Celite and the filtrate was concentrated to yield 4'-((S)-3-(cyanomethyl)piperazin-1-yl)-3,4,5',6'-tetrahydro-2H-spiro[naphthalene-1,7'-pyrano[2,3-d]pyrimidine]-2'-carboxamide (Int 18g). MS (ESI): $[M+H]^+$ m/z: 419.

Step H: 4'-((S)-4-acryloyl-3-(cyanomethyl)piperazin-1-yl)-3,4,5',6'-tetrahydro-2H-spiro[naphthalene-1,7'-pyrano[2,3-d]pyrimidine]-2'-carboxamide (Ex. 18b)

To a solution of 4'-((S)-3-(cyanomethyl)piperazin-1-yl)-3,4,5',6'-tetrahydro-2H-spiro[naphthalene-1,7'-pyrano[2,3-d]pyrimidine]-2'-carboxamide (Int 18g) (104 mg, 0.249 mmol) in DCM (2250 μl) was added 4-methylmorpholine (82 μl, 0.746 mmol) and acrylic anhydride (31.5 μl, 0.273 mmol) under nitrogen. The reaction mixture was stirred at room temperature for 30 minutes. The reaction mixture was then diluted with DCM, washed with brine solution and concentrated. The crude material was purified on a 24 g silica gel column eluting with 20% of methanol in DCM to yield racemic product. The racemic material was resolved by SFC (Column F; MeOH and 25% MeOH (with 0.1% $NH_4OH$)) to provide 4'-((S)-4-acryloyl-3-(cyanomethyl)piperazin-1-yl)-3,4,5',6'-tetrahydro-2H-spiro[naphthalene-1,7'-pyrano[2,3-d]pyrimidine]-2'-carboxamide; Peak 2 (Ex. 18b) MS (ESI): $[M+H]^+$ m/z: 473.3; $^1$H NMR (499 MHz, DMSO-$d_6$) δ 7.91 (s, 1H), 7.56 (s, 1H), 7.44 (d, J=7.2 Hz, 1H), 7.30-7.20 (m, 2H), 7.18 (d, J=7.3 Hz, 1H), 7.00-6.78 (m, 1H), 6.24-6.14 (m, 1H), 5.78 (d, J=10.8 Hz, 1H), 4.97 (s, 1H), 4.00 (dd, J=34.5, 12.7 Hz, 3H), 3.67 (s, 1H), 3.06-2.62 (m, 7H), 2.22-1.91 (m, 4H), 1.88-1.74 (m, 2H).

Example 19a: 4'-(4-acryloylpiperazin-1-yl)-N—((R)-1-(dimethylamino)propan-2-yl)-8-methyl-3,4,5',6'-tetrahydro-2H-spiro[naphthalene-1,7'-pyrano[2,3-d]pyrimidine]-2'-carboxamide

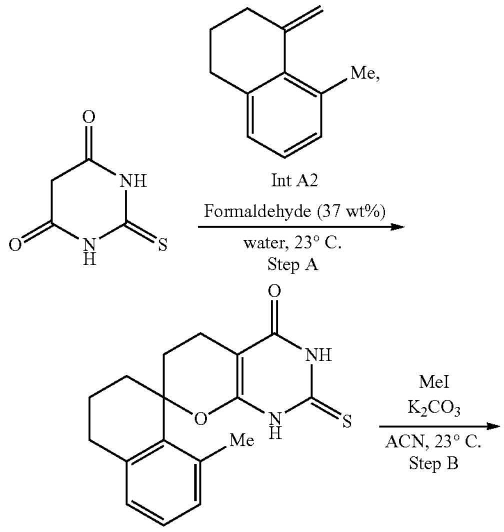

Int 19a

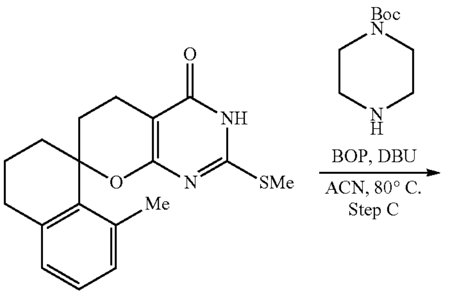

Int 19b

-continued

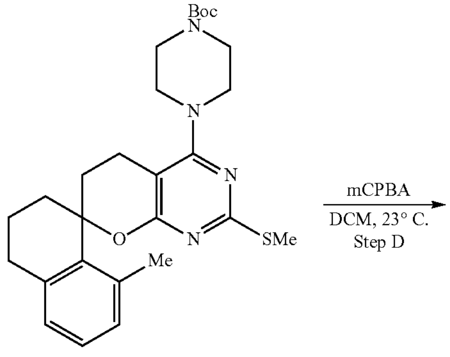

Int 19c

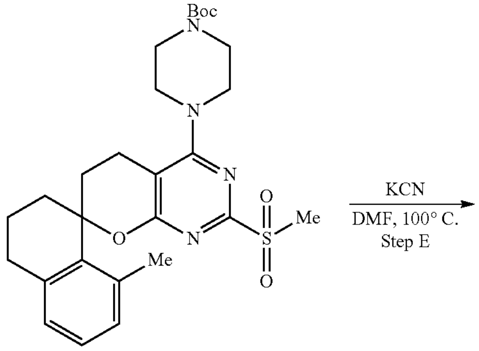

Int 19d

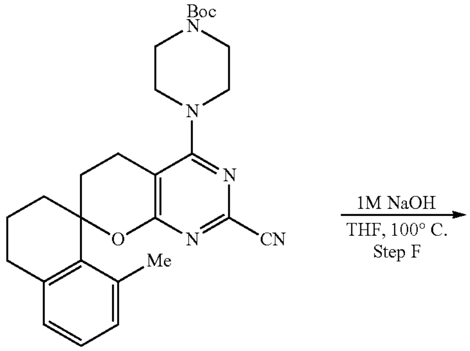

Int 19e

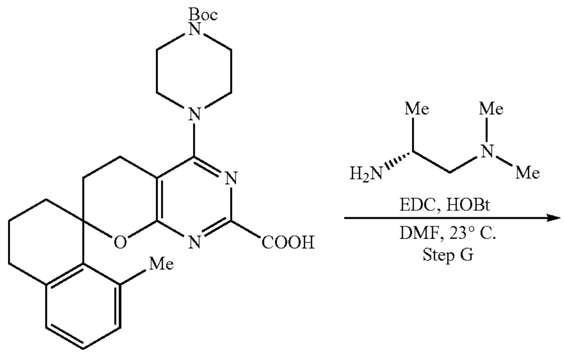

Int 19f

-continued

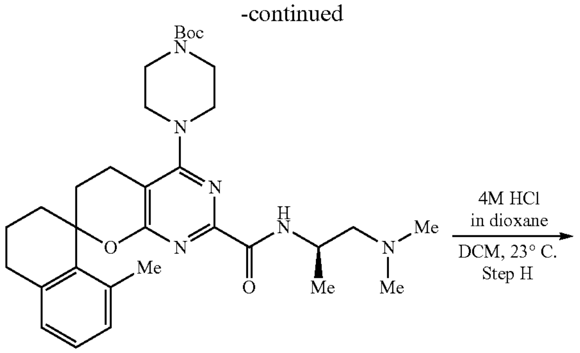

Int 19g

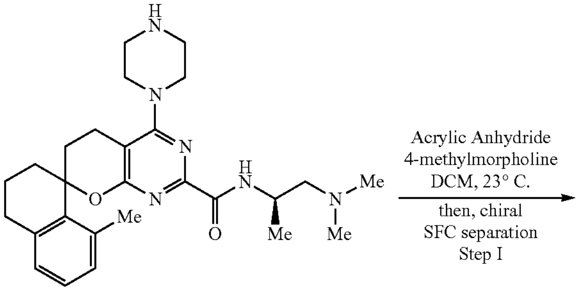

Int 19h

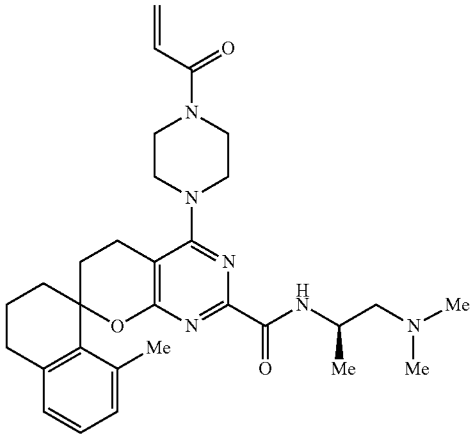

Ex 19a

Step A: 8-methyl-2'-thioxo-2',3,3',4,5',6'-hexahydro-2H-spiro[naphthalene-1,7'-pyrano[2,3-d]pyrimidin]-4'(1'H)-one (Int 19a)

To a mixture of 8-methyl-1-methylene-1,2,3,4-tetrahydronaphthalene (Int A2, 613 mg, 3.87 mmol), 2-thioxodihydropyrimidine-4,6(1H,5H)-dione (838 mg, 5.81 mmol) and formaldehyde (37% in $H_2O$) (0.577 mL, 7.75 mmol) was added water (5.5 mL). The reaction mixture was stirred at room temperature overnight. The white cloudy suspension was lyophilized overnight to yield 8-methyl-2'-thioxo-2',3,3',4,5',6'-hexahydro-2H-spiro[naphthalene-1,7'-pyrano[2,3-d]pyrimidin]-4'(1'H)-one (Int 19a). MS (ESI): $[M+H]^+$ m/z: 315.

Step B: 8-methyl-2'-(methylthio)-3,4,5',6'-tetrahydro-2H-spiro[naphthalene-1,7'-pyrano[2,3-d]pyrimidin]-4'(3'H)-one (Int 19b)

To a solution of 8-methyl-2'-thioxo-2',3,3',4,5',6'-hexahydro-2H-spiro[naphthalene-1,7'-pyrano[2,3-d]pyrimidin]-4'(1'H)-one (Int 19a) (1000 mg, 3.18 mmol) in acetonitrile (18 mL) was added $K_2CO_3$ (659 mg, 4.77 mmol). The reaction was stirred at room temperature for 1 h and iodomethane (0.259 mL, 4.13 mmol) was added. The reaction mixture was then stirred at room temperature overnight. The reaction mixture was concentrated and lyophilized overnight to yield 8-methyl-2'-(methylthio)-3,4,5',6'-tetrahydro-2H-spiro[naphthalene-1,7'-pyrano[2,3-d]pyrimidin]-4'(3'H)-one (Int 19b). MS (ESI): $[M+H]^+$ m/z: 329.

Step C: tert-butyl 4-(8-methyl-2'-(methylthio)-3,4,5',6'-tetrahydro-2H-spiro[naphthalene-1,7'-pyrano[2,3-d]pyrimidin]-4'-yl)piperazine-1-carboxylate (Int 19c)

To a solution of 8-methyl-2'-(methylthio)-3,4,5',6'-tetrahydro-2H-spiro[naphthalene-1,7'-pyrano[2,3-d]pyrimidin]-4'(3'H)-one (Int 19b) (500 mg, 1.522 mmol) in acetonitrile (7 mL) were added benzyl (S)-2-(cyanomethyl)piperazine-1-carboxylate (567 mg, 3.04 mmol), BOP (875 mg, 1.98 mmol) followed by DBU (695 mL, 4.57 mmol). The resulting mixture was heated at 80° C. overnight. The reaction mixture was quenched with water (5 mL) and extracted with EtOAc (3×5 mL). The combined organic layers were concentrated and purified using 24 g silica gel column with 30% of EtOAc in hexanes to yield tert-butyl 4-(8-methyl-2'-(methylthio)-3,4,5',6'-tetrahydro-2H-spiro[naphthalene-1,7'-pyrano[2,3-d]pyrimidin]-4'-yl)piperazine-1-carboxylate (Int 19c). MS (ESI): $[M+H]^+$ m/z: 497.

Step D: tert-butyl 4-(8-methyl-2'-(methylsulfonyl)-3,4,5',6'-tetrahydro-2H-spiro[naphthalene-1,7'-pyrano[2,3-d]pyrimidin]-4'-yl)piperazine-1-carboxylate (Int 19d)

A mixture of tert-butyl 4-(8-methyl-2'-(methylthio)-3,4,5',6'-tetrahydro-2H-spiro[naphthalene-1,7'-pyrano[2,3-d]pyrimidin]-4'-yl)piperazine-1-carboxylate (Int 19c) (281 mg, 0.566 mmol) and 3-chlorobenzoperoxoic acid (293 mg, 1.697 mmol) in DCM (2.8 mL) was stirred at room temperature for 3 h. The reaction mixture was diluted with DCM, filtered and the filtrate was washed with saturated, aqueous $NaHCO_3$ solution. The combined organic layers were concentrated to yield tert-butyl 4-(8-methyl-2'-(methylsulfonyl)-3,4,5',6'-tetrahydro-2H-spiro[naphthalene-1,7'-pyrano[2,3-d]pyrimidin]-4'-yl)piperazine-1-carboxylate (Int 19d). MS (ESI): $[M+H]^+$ m/z: 529.

Step E: tert-butyl 4-(2'-cyano-8-methyl-3,4,5',6'-tetrahydro-2H-spiro[naphthalene-1,7'-pyrano[2,3-d]pyrimidin]-4'-yl)piperazine-1-carboxylate (Int 19e)

To a mixture of tert-butyl 4-(8-methyl-2'-(methylsulfonyl)-3,4,5',6'-tetrahydro-2H-spiro[naphthalene-1,7'-pyrano[2,3-d]pyrimidin]-4'-yl)piperazine-1-carboxylate (Int 19d) (268 mg, 0.507 mmol) in DMF (9 mL) was added KCN (66 mg, 1.014 mmol) and heated at 100° C. overnight. The reaction mixture was quenched with 5 mL of water and extracted with EtOAc (3×10 mL). The combined organic layers were washed with brine solution and concentrated. The crude material was purified on 12 g silica gel column eluting with 45% of EtOAc in hexane to provide tert-butyl 4-(2'-cyano-8-methyl-3,4,5',6'-tetrahydro-2H-spiro[naphthalene-1,7'-pyrano[2,3-d]pyrimidin]-4'-yl)piperazine-1-carboxylate (Int 19e). MS (ESI): $[M+H]^+$ m/z: 476.

Step F: 4'-(4-(tert-butoxycarbonyl)piperazin-1-yl)-8-methyl-3,4,5',6'-tetrahydro-2H-spiro[naphthalene-1,7'-pyrano[2,3-d]pyrimidine]-2'-carboxylic acid (Int 19f)

A 20 mL microwave vial was charged with tert-butyl 4-(2'-cyano-8-methyl-3,4,5',6'-tetrahydro-2H-spiro[naphthalene-1,7'-pyrano[2,3-d]pyrimidin]-4'-yl)piperazine-1-carboxylate (Int 19e) (7151 mg, 0.317 mmol) in THF (13 mL) and 1M NaOH (3.17 mL, 3.17 mmol). It was then heated at 100° C. for 4 h. The reaction mixture was acidified with 1N HCl and extracted with ethyl acetate. The combined organic layers were washed with saturated brine solution and concentrated to afford 4'-(4-(tert-butoxycarbonyl)piperazin-1-yl)-8-methyl-3,4,5',6'-tetrahydro-2H-spiro[naphthalene-1,7'-pyrano[2,3-d]pyrimidine]-2'-carboxylic acid (Int 19f). MS (ESI): $[M+H]^+$ m/z: 495.

Step G: tert-butyl 4-(2'-((1-(dimethylamino)propan-2-yl)carbamoyl)-8-methyl-3,4,5',6'-tetrahydro-2H-spiro[naphthalene-1,7'-pyrano[2,3-d]pyrimidin]-4'-yl)piperazine-1-carboxylate (Int 19g)

To a solution of 4'-(4-(tert-butoxycarbonyl)piperazin-1-yl)-8-methyl-3,4,5',6'-tetrahydro-2H-spiro[naphthalene-1,7'-pyrano[2,3-d]pyrimidine]-2'-carboxylic acid (Int 19f) (95 mg, 0.192 mmol) in DMF (1800 μl) was added (R)—$N^1$,$N^1$-dimethylpropane-1,2-diamine (23.55 mg, 0.230 mmol) followed by HOBt (44.1 mg, 0.288 mmol) and EDC (55.2 mg, 0.288 mmol). The reaction mixture was stirred at rt for 3 h. The reaction mixture was quenched with water and extracted with EtOAc. The combined organic layers were washed with brine solution and concentrated. The crude material was purified on a 12 g silica gel column eluting with 50% of EtOAc in hexane to provide tert-butyl 4-(2'-((1-(dimethylamino)propan-2-yl)carbamoyl)-8-methyl-3,4,5',6'-tetrahydro-2H-spiro[naphthalene-1,7'-pyrano[2,3-d]pyrimidin]-4'-yl)piperazine-1-carboxylate (Int 19g). MS (ESI): $[M+H]^+$ m/z: 579.

Step H: N-(1-(dimethylamino)propan-2-yl)-8-methyl-4'-(piperazin-1-yl)-3,4,5',6'-tetrahydro-2H-spiro[naphthalene-1,7'-pyrano[2,3-d]pyrimidine]-2'-carboxamide (Int 19h)

To a solution of tert-butyl 4-(2'-((1-(dimethylamino)propan-2-yl)carbamoyl)-8-methyl-3,4,5',6'-tetrahydro-2H-spiro[naphthalene-1,7'-pyrano[2,3-d]pyrimidin]-4'-yl)piperazine-1-carboxylate (Int 19g) (86 mg, 0.149 mmol) in DCM (1000 μl) was added 4M HCl in dioxane (186 μl, 0.743 mmol). The reaction mixture was stirred at rt for 1 h. The mixture was diluted with 3 mL of DCM and concentrated to yield N-(1-(dimethylamino)propan-2-yl)-8-methyl-4'-(piperazin-1-yl)-3,4,5',6'-tetrahydro-2H-spiro[naphthalene-1,7'-pyrano[2,3-d]pyrimidine]-2'-carboxamide (Int 19h). MS (ESI): $[M+H]^+$ m/z: 479.

Step I: 4'-(4-acryloylpiperazin-1-yl)-N—((R)-1-(dimethylamino)propan-2-yl)-8-methyl-3,4,5',6'-tetrahydro-2H-spiro[naphthalene-1,7'-pyrano[2,3-d]pyrimidine]-2'-carboxamide (Ex. 19a)

To a solution of N-(1-(dimethylamino)propan-2-yl)-8-methyl-4'-(piperazin-1-yl)-3,4,5',6'-tetrahydro-2H-spiro[naphthalene-1,7'-pyrano[2,3-d]pyrimidine]-2'-carboxamide (71 mg, 0.148 mmol) (Int 19h) (104 mg, 0.249 mmol) in DCM (1450 μl) were added 4-methylmorpholine (326 μl, 2.97 mmol) and acrylic anhydride (20.52 μl, 0.178 mmol) under nitrogen. The reaction mixture was stirred at room temperature for 1 h. The reaction mixture was then diluted with DCM, washed with brine solution and concentrated. The crude material was purified on a 12 g silica gel column eluting with 30% of methanol in DCM to yield racemic product. The racemic material was resolved by SFC (Column G; acetonitrile and 25% MeOH (with 0.1% $NH_4OH$)) to provide 4'-(4-acryloylpiperazin-1-yl)-N—((R)-1-(dimethylamino)propan-2-yl)-8-methyl-3,4,5',6'-tetrahydro-2H-spiro[naphthalene-1,7'-pyrano[2,3-d]pyrimidine]-2'-carboxamide (12.3 mg, 0.023 mmol); Peak 1 (Ex. 19a) MS (ESI): $[M+H]^+$ m/z: 533.3; $^1H$ NMR (499 MHz, DMSO-$d_6$) δ 8.33 (s, 1H), 7.13 (t, J=7.5 Hz, 1H), 7.01 (d, J=7.5 Hz, 2H), 6.86 (dd, J=16.7, 10.5 Hz, 1H), 6.16 (dd, J=16.7, 2.3 Hz, 1H), 5.74 (dd, J=10.4, 2.3 Hz, 1H), 4.13 (s, 1H), 3.92-3.66 (m, 2H), 3.64 (m, J=8.7 Hz, 4H), 3.47-3.37 (m, 2H), 3.04-2.74 (m, 4H), 2.55 (m, J=16.9 Hz, 2H), 2.31 (s, J=13.1 Hz, 6H), 2.17-2.07 (m, 2H), 1.94-1.75 (m, 3H), 1.16 (d, J=6.6 Hz, 3H).

Example 20a/b: 2-((2S)-1-acryloyl-4-(2'-(3-(dimethylamino)azetidin-1-yl)-3,4,5',6'-tetrahydro-2H-spiro[naphthalene-1,7'-pyrano[2,3-d]pyrimidin]-4'-yl)piperazin-2-yl)acetonitrile

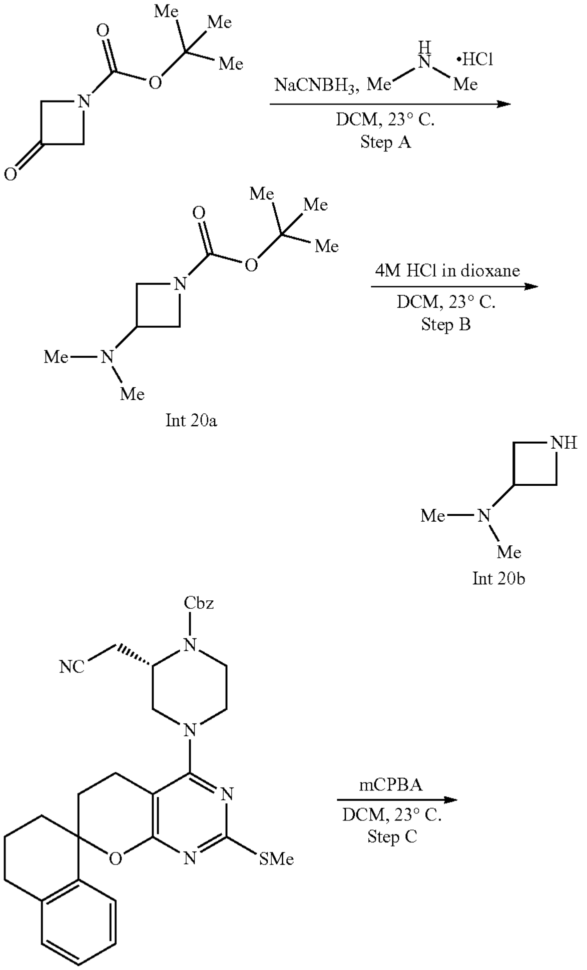

Int 20a

Int 20b

-continued

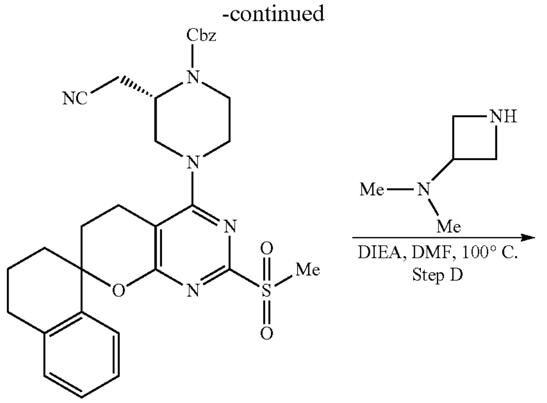

Int 20c

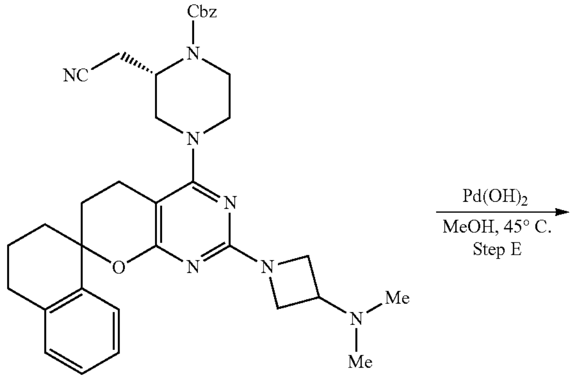

Int 20d

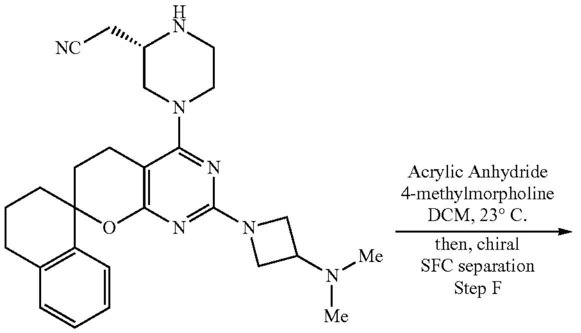

Int 20e

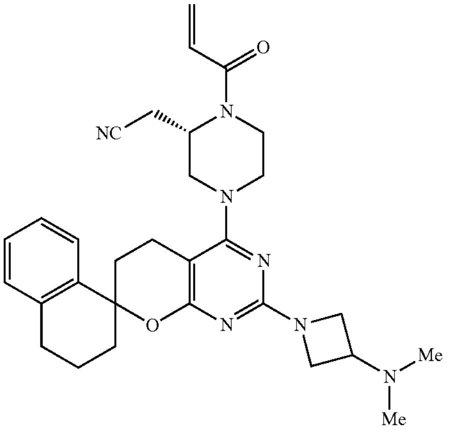

Ex 20a
Ex 20b

Step A: tert-butyl 3-(dimethylamino)azetidine-1-carboxylate (Int 20a)

To a solution of tert-butyl 3-oxoazetidine-1-carboxylate (3.29 g, 19.22 mmol) in DCM (50 mL) was added dimethylamine hydrochloride (2.351 g, 28.8 mmol). This mixture was stirred at rt for 2 h and the sodium cyanoborohydride (1.812 g, 28.8 mmol) was added. The reaction mixture was stirred at room temperature overnight. The reaction mixture was quenched with water and extracted with DCM thrice. The combined organic layers were washed with saturated brine solution and concentrated to get tert-butyl 3-(dimethylamino)azetidine-1-carboxylate (Int 20a). MS (ESI): $[M+H]^+$ m/z: 201.

Step B: N,N-dimethylazetidin-3-amine (Int 20b)

To a mixture of tert-butyl 3-(dimethylamino)azetidine-1-carboxylate (Int 20a) (4.12 g, 0.00 mmol) in DCM (10 mL) was added 4 M HCl in dioxane (51.4 mL, 206 mmol). The reaction mixture was stirred at rt for 1 h. The crude mixture was concentrated and lyophilized to provide N,N-dimethylazetidin-3-amine (Int 20b). MS (ESI): $[M+H]^+$ m/z: 101.

Step C: benzyl (2S)-2-(cyanomethyl)-4-(2'-(methylsulfonyl)-3,4,5',6'-tetrahydro-2H-spiro[naphthalene-1,7'-pyrano[2,3-d]pyrimidin]-4'-yl)piperazine-1-carboxylate (Int 20c)

A mixture of benzyl (2S)-2-(cyanomethyl)-4-(2'-(methylthio)-3,4,5',6'-tetrahydro-2H-spiro[naphthalene-1,7'-pyrano[2,3-d]pyrimidin]-4'-yl)piperazine-1-carboxylate (1500 mg, 2.70 mmol) and 3-chlorobenzoperoxoic acid (1397 mg, 8.10 mmol) in DCM (20 mL) was stirred at room temperature for 3 h. The reaction mixture was diluted with DCM, filtered and the filtrate was washed with saturated, aqueous $NaHCO_3$ solution. The combined organic layers were concentrated to yield benzyl (2S)-2-(cyanomethyl)-4-(2'-(methylsulfonyl)-3,4,5',6'-tetrahydro-2H-spiro[naphthalene-1,7'-pyrano[2,3-d]pyrimidin]-4'-yl)piperazine-1-carboxylate (Int 20c). MS (ESI): $[M+H]^+$ m/z: 588.

Step D: benzyl (2S)-2-(cyanomethyl)-4-(2'-(3-(dimethylamino)azetidin-1-yl)-3,4,5',6'-tetrahydro-2H-spiro[naphthalene-1,7'-pyrano[2,3-d]pyrimidin-]-4'-yl)piperazine-1-carboxylate (Int 20d)

To a mixture of benzyl (2S)-2-(cyanomethyl)-4-(2'-(methylsulfonyl)-3,4,5',6'-tetrahydro-2H-spiro[naphthalene-1,7'-pyrano[2,3-d]pyrimidin]-4'-yl)piperazine-1-carboxylate (250 mg, 0.425 mmol) (Int 20c) in DMF (2 mL) was added N, N-dimethylazetidin-3-amine (Int 20b) (0.370 mL, 2.127 mmol). The reaction mixture was heated at 100° C. overnight. The reaction mixture was quenched with water and extracted with EtOAc thrice, the combined organic layers were washed with water, brine solution and concentrated. The crude mixture was purified on a 24 g silica gel column with 5-20% of methanol in dichloromethane to afford benzyl (2S)-2-(cyanomethyl)-4-(2'-(3-(dimethylamino)azetidin-1-yl)-3,4,5',6'-tetrahydro-2H-spiro[naphthalene-1,7'-pyrano[2,3-d]pyrimidin]-4'-yl)piperazine-1-carboxylate (Int 20d). MS (ESI): $[M+H]^+$ m/z: 608.

Step E: 2-((2S)-4-(2'-(3-(dimethylamino)azetidin-1-yl)-3,4,5',6'-tetrahydro-2H-spiro[naphthalene-1,7'-pyrano[2,3-d]pyrimidin]-4'-yl)piperazin-2-yl)acetonitrile (Int 20e)

A 20 mL vial was charged with Pd—C(25.8 mg, 0.092 mmol) and benzyl (2S)-2-(cyanomethyl)-4-(2'-(3-(dimethylamino)azetidin-1-yl)-3,4,5',6'-tetrahydro-2H-spiro[naphthalene-1,7'-pyrano[2,3-d]pyrimidin]-4'-yl)piperazine-1-carboxylate (Int 20d) (186 mg, 0.306 mmol) in MeOH (3000 µl) under nitrogen. The reaction mixture was degassified with vacuum and back filled with nitrogen thrice and stirred under a hydrogen balloon at room temperature for 4 h. The reaction mixture was filtered over CELITE and the filtrate was concentrated to yield 2-((2S)-4-(2'-(3-(dimethylamino)azetidin-1-yl)-3,4,5',6'-tetrahydro-2H-spiro[naphthalene-1,7'-pyrano[2,3-d]pyrimidin]-4'-yl)piperazin-2-yl)acetonitrile (Int 20e). MS (ESI): $[M+H]^+$ m/z: 474.

Step F: 2-((2S)-1-acryloyl-4-(2'-(3-(dimethylamino)azetidin-1-yl)-3,4,5',6'-tetrahydro-2H-spiro[naphthalene-1,7'-pyrano[2,3-d]pyrimidin]-4'-yl)piperazin-2-yl)acetonitrile (Ex. 20a/b)

To a solution of 2-((2S)-4-(2'-(3-(dimethylamino)azetidin-1-yl)-3,4,5',6'-tetrahydro-2H-spiro[naphthalene-1,7'-pyrano[2,3-d]pyrimidin]-4'-yl)piperazin-2-yl)acetonitrile (112 mg, 0.236 mmol) (Int 22e) in DCM (2500 µl) were added 4-methylmorpholine (78 µl, 0.709 mmol) and acrylic anhydride (35.4 µl, 0.307 mmol) under nitrogen. The reaction mixture was stirred at room temperature for 1 h. The reaction mixture was then diluted with DCM, washed with brine solution and concentrated. The crude material was purified on a 24 g silica gel column eluting with 20% of methanol in DCM to yield racemic product. The racemic material was resolved by SFC (Column A; MeOH and 25% MeOH (with 0.1% $NH_4OH$)) to provide 2-((2S)-1-acryloyl-4-(2'-(3-(dimethylamino)azetidin-1-yl)-3,4,5',6'-tetrahydro-2H-spiro[naphthalene-1,7'-pyrano[2,3-d]pyrimidin]-4'-yl)piperazin-2-yl)acetonitrile (3.5 mg, 0.0066 mmol); Peak 1 (Ex. 20a) MS (ESI): $[M+H]^+$ m/z: 528.2; $^1H$ NMR (499 MHz, DMSO-$d_6$) δ 7.42-7.36 (m, 1H), 7.29-7.19 (m, 2H), 7.19-7.12 (m, 1H), 6.85 (d, J=29.1 Hz, 1H), 6.22-6.12 (m, 1H), 5.77 (dd, J=10.3, 2.1 Hz, 1H), 4.04-3.95 (m, 1H), 3.95-3.83 (m, 3H), 3.83-3.63 (m, 3H), 3.22-2.97 (m, 3H), 2.96-2.62 (m, 7H), 2.44-2.22 (m, 1H), 2.08 (s, J=4.2 Hz, 6H), 2.03 (m, J=5.9 Hz, 2H), 2.00-1.90 (m, 2H), 1.89-1.76 (m, 2H); and 2-((2S)-1-acryloyl-4-(2'-(3-(dimethylamino)azetidin-1-yl)-3,4,5',6'-tetrahydro-2H-spiro[naphthalene-1,7'-pyrano[2,3-d]pyrimidin]-4'-yl)piperazin-2-yl)acetonitrile (7.0 mg, 0.013 mmol); Peak 2 (Ex. 20b) MS (ESI): $[M+H]^+$ m/z: 528.2; $^1H$ NMR (499 MHz, DMSO-$d_6$) δ 7.36 (d, J=7.4 Hz, 1H), 7.22 (m, J=7.1, 1.6 Hz, 2H), 7.18-7.13 (m, 1H), 6.85 (s, 1H), 6.18 (d, J=16.9 Hz, 1H), 5.77 (d, J=11.0 Hz, 1H), 4.04 (m, J=12.8 Hz, 1H), 3.96-3.85 (m, 3H), 3.80-3.60 (m, 3H), 3.05 (m, J=11.7, 6.3 Hz, 3H), 3.01-2.62 (m, 7H), 2.42 (s, 1H), 2.08 (s, 6H), 1.97 (m, J=19.1, 9.7, 4.6 Hz, 4H), 1.88-1.73 (m, 2H).

Example 21a: 1-(4-(2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-1-yl)prop-2-en-1-one

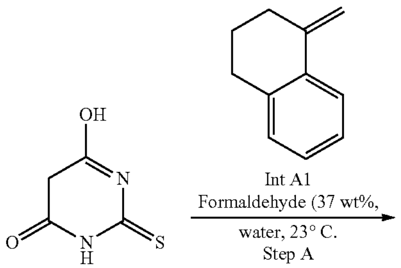

-continued

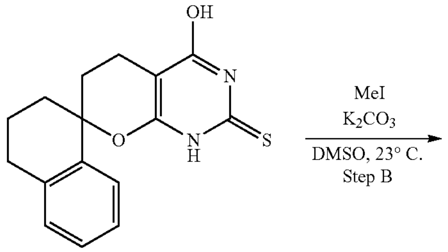

Int 21a

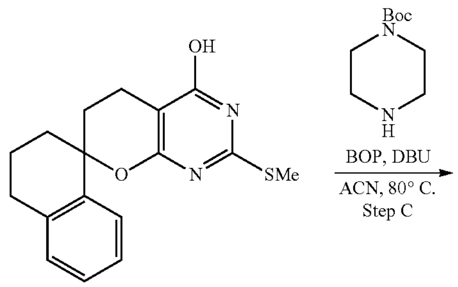

Int 21b

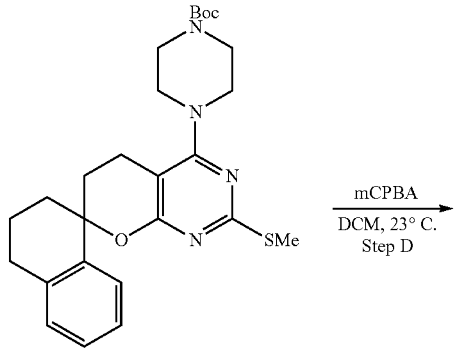

Int 21c

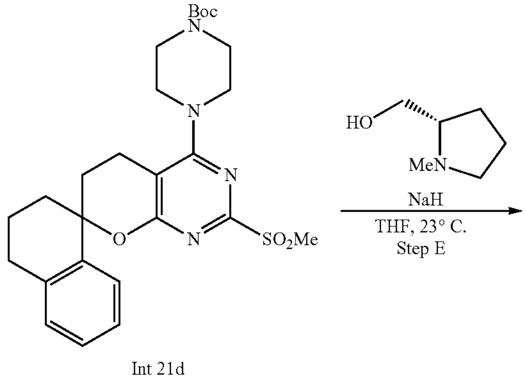

Int 21d

-continued

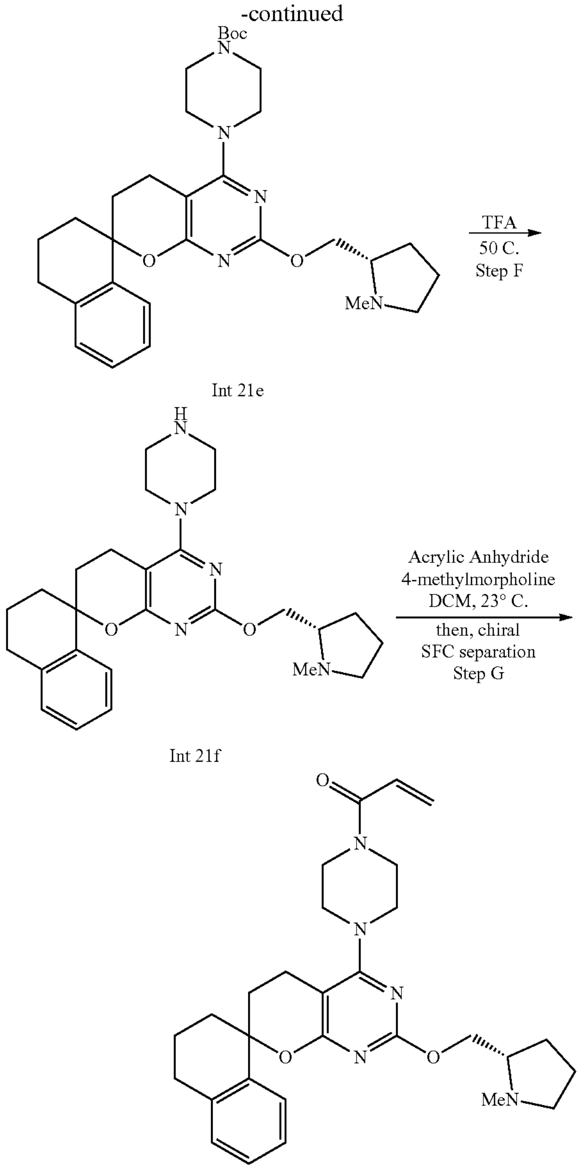

Int 21e

Int 21f

Ex 21a

Step A: 2'-thioxo-2',3,3',4,5',6'-hexahydro-2H-spiro[naphthalene-1,7'-pyrano[2,3-d]pyrimidin]-4'(1'H)-one (Int 21a)

To a mixture of 1-methylene-1,2,3,4-tetrahydronaphthalene (Int A1, 450 mg, 3.12 mmol), 2-thioxodihydropyrimidine-4,6(1H,5H)-dione (675 mg, 4.68 mmol) and formaldehyde (37% in $H_2O$) (0.465 mL, 6.24 mmol) was added water (3 mL). The reaction mixture was stirred at room temperature for 4 h. The white cloudy suspension was lyophilized overnight to yield 2'-thioxo-2',3,3',4,5',6'-hexahydro-2H-spiro[naphthalene-1,7'-pyrano[2,3-d]pyrimidin]-4'(1'H)-one (Int 21a). MS (ESI): $[M+H]^+$ m/z: 301.

Step B: 2'-(methylthio)-3,4,5',6'-tetrahydro-2H-spiro[naphthalene-1,7'-pyrano[2,3-d]pyrimidin]-4'(3'H)-one (Int 21b)

To a solution of 2'-thioxo-2',3,3',4,5',6'-hexahydro-2H-spiro[naphthalene-1,7'-pyrano[2,3-d]pyrimidin]-4'(1'H)-one (Int 21a) (300 mg, 0.999 mmol) in DMSO (5 mL) was added $K_2CO_3$ (207 mg, 1.498 mmol). The reaction was stirred at room temperature for 1 h and iodomethane (0.062 mL, 0.999 mmol) was added. The reaction mixture was then stirred at room temperature over the weekend. The reaction mixture was filtered and the solid collected was dried under vacuum to yield 2'-(methylthio)-3,4,5',6'-tetrahydro-2H-spiro[naphthalene-1,7'-pyrano[2,3-d]pyrimidin]-4'(3'H)-one_(Int 21b). MS (ESI): $[M+H]^+$ m/z: 315.

Step C: tert-butyl 4-(2'-(methylthio)-3,4,5',6'-tetrahydro-2H-spiro[naphthalene-1,7'-pyrano[2,3-d]pyrimidin]-4'-yl)piperazine-1-carboxylate (Int 21c)

To a solution of 2'-(methylthio)-3,4,5',6'-tetrahydro-2H-spiro[naphthalene-1,7'-pyrano[2,3-d]pyrimidin]-4'(3'H)-one (Int 21b) (148 mg, 0.471 mmol) in acetonitrile (1.4 mL) were added tert-butyl piperazine-1-carboxylate (175 mg, 0.941 mmol) and BOP (271 mg, 0.612 mmol) followed by DBU (215 µl, 1.412 mmol). The resulting mixture was heated at 80° C. overnight. The reaction mixture was quenched with water (5 mL) and extracted with EtOAc (3×3 mL). The combined organic layers were concentrated and purified using a 24 g silica gel column eluting with 30% of EtOAc in hexanes to yield tert-butyl 4-(2'-(methylthio)-3,4,5',6'-tetrahydro-2H-spiro[naphthalene-1,7'-pyrano[2,3-d]pyrimidin]-4'-yl)piperazine-1-carboxylate (Int 21c). MS (ESI): $[M+H]^+$ m/z: 483.

Step D: tert-butyl 4-(2'-(methylsulfonyl)-3,4,5',6'-tetrahydro-2H-spiro[naphthalene-1,7'-pyrano[2,3-d]pyrimidin]-4'-yl)piperazine-1-carboxylate (Int 21d)

A mixture of tert-butyl 4-(2'-(methylthio)-3,4,5',6'-tetrahydro-2H-spiro[naphthalene-1,7'-pyrano[2,3-d]pyrimidin]-4'-yl)piperazine-1-carboxylate (145 mg, 0.300 mmol) (Int 21c) (1250 mg, 2.249 mmol) and m-chlorobenzoperoxoic acid (156 mg, 0.901 mmol) in DCM (1.5 mL) was stirred at room temperature for 3 h. The reaction mixture was diluted with DCM, filtered and the filtrate was washed with saturated, aqueous $NaHCO_3$ solution. The combined organic layers were concentrated to yield tert-butyl 4-(2'-(methylsulfonyl)-3,4,5',6'-tetrahydro-2H-spiro[naphthalene-1,7'-pyrano[2,3-d]pyrimidin]-4'-yl)piperazine-1-carboxylate (Int 21d). MS (ESI): $[M+H]^+$ m/z: 515.

Step E: tert-butyl 4-(2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazine-1-carboxylate (Int 21e)

To a mixture of NaH (35.0 mg, 0.874 mmol), (S)-(1-methylpyrrolidin-2-yl)methanol (104 µL, 0.874 mmol) and tert-butyl 4-(2'-(methylsulfonyl)-3,4,5',6'-tetrahydro-2H-spiro[naphthalene-1,7'-pyrano[2,3-d]pyrimidin]-4'-yl)piperazine-1-carboxylate (150 mg, 0.291 mmol) (Int 21d) was added THF (1500 µL) under nitrogen. The reaction mixture was stirred at room temperature for 1 h. The reaction was then diluted with methanol and concentrated. The crude material was purified on a 24 g silica gel column eluting with 30% of methanol in DCM to yield tert-butyl 4-(2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazine-1-carboxylate (Int 21e). MS (ESI): $[M+H]^+$ m/z: 550.

Step F: 2'-(((S)-1-methylpyrrolidin-2-yl methoxy)-4'-(piperazin-1-yl)-3,4,5',6'-tetrahydro-2H-spiro [naphthalene-1,7'-pyrano[2,3-d]pyrimidine] (Int 21f)

A mixture of tert-butyl 4-(2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazine-1-carboxylate (Int 21e) (104 mg, 0.189 mmol) and TFA (219 μl, 2.84 mmol) was heated at 50° C. for 3 h. The crude mixture was concentrated and re-dissolved in 5 mL DCM and neutralized with saturated, aqueous $NaHCO_3$. The organic layer was separated and concentrated to yield 2'-(((S)-1-methylpyrrolidin-2-yl)methoxy)-4'-(piperazin-1-yl)-3,4,5',6'-tetrahydro-2H-spiro[naphthalene-1,7'-pyrano[2,3-d]pyrimidine] (Int 21f).MS (ESI): $[M+H]^+$ m/z: 450.

Step G: 1-(4-(2'-(((S)-1-methylpyrrolidin-2-yl methoxy)-3,4,5',6'-tetrahydro-2H-spiro[naphthalene-1,7'-pyrano[2,3-d]pyrimidin]-4'-yl)piperazin-1-yl) prop-2-en-1-one (Ex. 21a)

To a solution of 2'-(((S)-1-methylpyrrolidin-2-yl) methoxy)-4'-(piperazin-1-yl)-3,4,5',6'-tetrahydro-2H-spiro [naphthalene-1,7'-pyrano[2,3-d]pyrimidine] (Int 21f) (75 mg, 0.167 mmol) in DCM (1500 μl) were added 4-methylmorpholine (55.0 μl, 0.500 mmol)) and acrylic anhydride (23.08 μl, 0.200 mmol) under nitrogen. The reaction mixture was stirred at room temperature for 30 minutes. The reaction mixture was then diluted with DCM, washed with brine solution and concentrated. The crude material was purified on a 24 g silica gel column eluting with 20% of methanol in DCM to yield racemic product. The racemic material was resolved by SFC (Column H; MeOH and 50% MeOH (with 0.1% $NH_4OH$)) to provide 1-(4-(2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-1-yl) prop-2-en-1-one; Peak 1 (Ex. 21a) MS (ESI): $[M+H]^+$ m/z: 504; $^1H$ NMR (499 MHz, DMSO-$d_6$) δ 7.43-7.37 (m, 1H), 7.29-7.19 (m, 2H), 7.16 (d, J=8.5 Hz, 1H), 6.83 (dd, J=16.7, 10.5 Hz, 1H), 6.15 (dd, J=16.7, 2.3 Hz, 1H), 5.72 (dd, J=10.5, 2.3 Hz, 1H), 4.17 (dd, J=10.7, 5.0 Hz, 1H), 3.99 (dd, J=10.7, 6.4 Hz, 1H), 3.86-3.58 (m, 4H), 3.51 (m, 4H), 2.93 (dt, J=8.9, 4.2 Hz, 1H), 2.90-2.70 (m, 3H), 2.49-2.40 (m, 2H), 2.32 (s, 3H), 2.16 (q, J=8.8 Hz, 1H), 2.10-1.94 (m, 4H), 1.94-1.77 (m, 3H), 1.71-1.61 (m, 2H), 1.55 (m, J=13.5, 6.8 Hz, 1H).

Examples 22a, 23a, and 24a were prepared using methods similar to those described above for Example 21.

| Ex. | Alkene Precursor | Structure | Compound Name | $[M + H]^+$ Found | Purification Conditions |
|---|---|---|---|---|---|
| 22a | Int A4 | 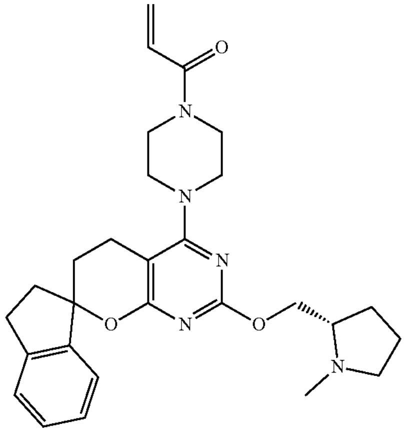 [SMILES: C=CC(=O)N1CCN(c2nc(OC[C@@H]3CCCN3C)nc3c2CCC2(CCc4ccccc42)O3)CC1] Peak 1 | 1-(4-(2'-(((S)-1-methylpyrrolidin-2-yl)methoxy)-2,3,5',6'-tetrahydrospiro [indene-1,7'-pyrano [2,3-d]pyrimidin]-4'-yl)piperazin-1-yl)prop-2-en-1-one | 490 | Column A; Condition: Acetonitrile/ Methanol and 30% Methanol (0.1% $NH_4OH$) |
| 23a | Int A9 | 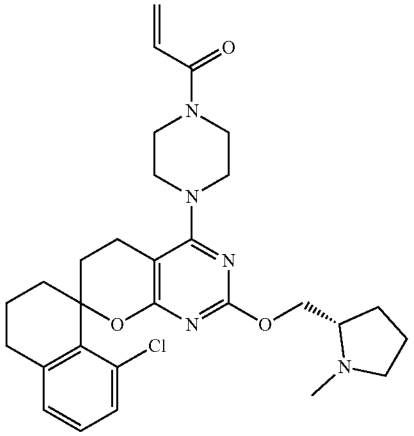 [SMILES: C=CC(=O)N1CCN(c2nc(OC[C@@H]3CCCN3C)nc3c2CCC2(CCCc4cccc(Cl)c42)O3)CC1] Peak 1 | 1-(4-(8-chloro-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-1-yl)prop-2-en-1-one | 538 | Column I; Condition: Acetonitrile/ Methanol and 15% Methanol (0.1% $NH_4OH$) |

-continued

| Ex. | Alkene Precursor | Structure | Compound Name | [M + H]+ Found | Purification Conditions |
|---|---|---|---|---|---|
| 24a | Int A2 | 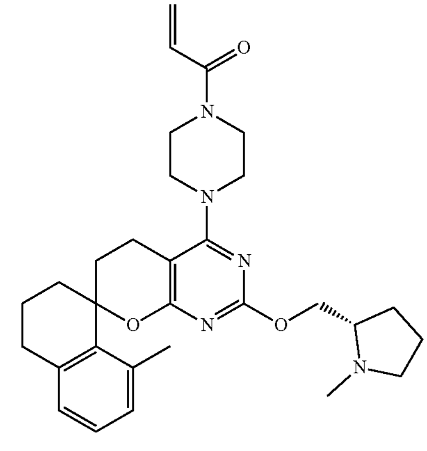 [SMILES: C=CC(=O)N1CCN(c2nc(OC[C@@H]3CCCN3C)nc3c2CCC2(CCCc4cccc(C)c42)O3)CC1] Peak 1 | 1-(4-(8-methyl-2'-(((S)-1-methylpyrrolidin-2-yl)methoxy)-3,4,5',6'-tetrahydro-2H-spiro[naphthalene-1,7'-pyrano[2,3-d]pyrimidin]-4'-yl)piperazin-1-yl)prop-2-en-1-one | 518 | Column A; Condition: Acetonitrile/ Methanol and 30% Methanol (0.1% $NH_4OH$) |

Example 25a/b/c/d: 2-((2S)-1-acryloyl-4-(3-methyl-2'-(((S)-1-methylpyrrolidin-2-yl)methoxy)-2,3,5',6'-tetrahydrospiro [indene-1,7'-pyrano [2,3-d]pyrimidin]-4'-yl)piperazin-2-yl)acetonitrile

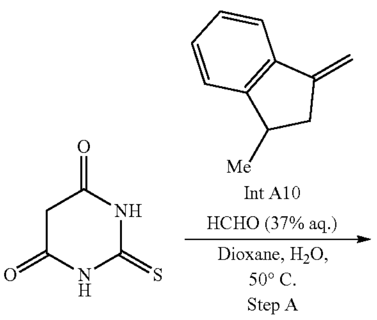

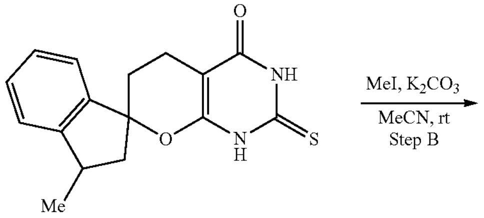

Int 25a

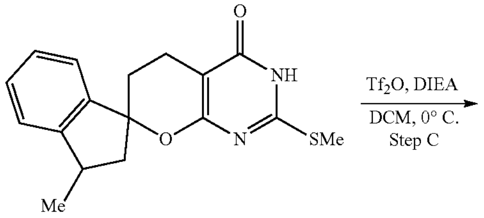

Int 25b

-continued

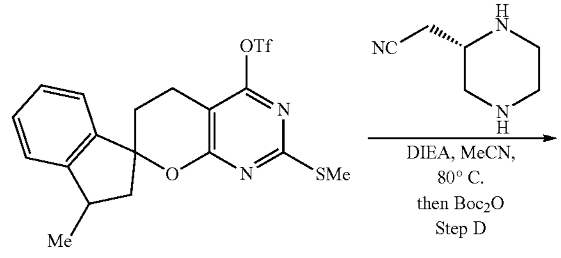

Int 25c

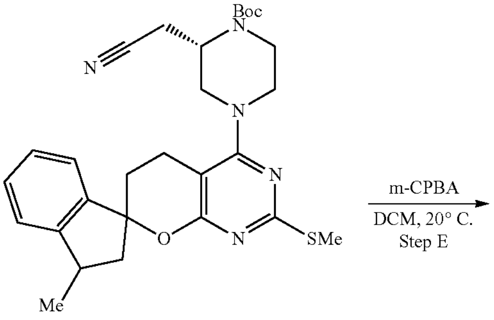

Int 25d

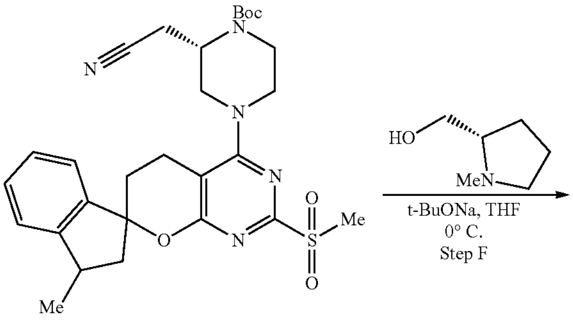

Int 25e

-continued

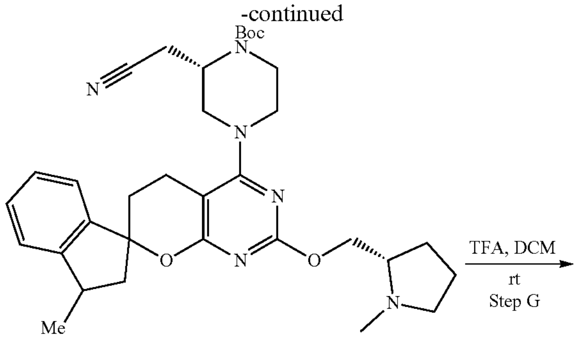

Int 25f

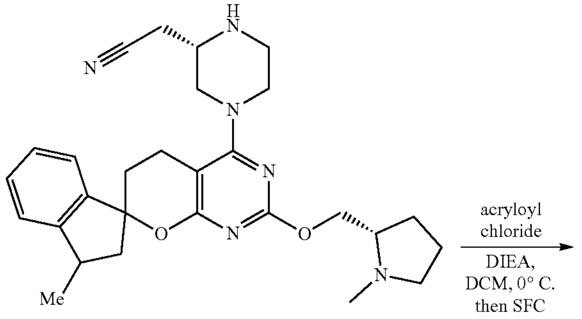

Int 25g

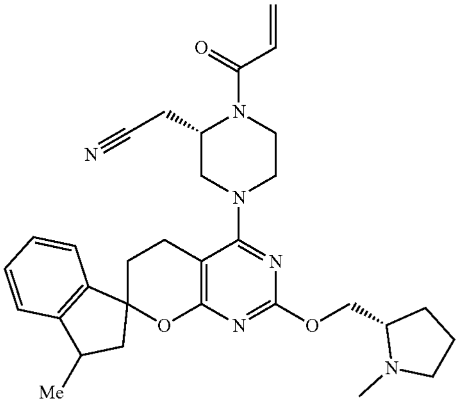

Ex 25a-d

Step A: 3-methyl-2'-thioxo-2,2',3,3',5',6'-hexahydrospiro[indene-1,7'-pyrano[2,3-d]pyrimidin]-4'(1'H)-one (Int 25a)

To a mixture of 1-methyl-3-methylene-2,3-dihydro-1H-indene (Int A10, 2.2 g, 15.26 mmol) in dioxane (30 mL) and water (30 mL) was added 2-thioxodihydropyrimidine-4,6(1H,5H)-dione (3.30 g, 22.9 mmol) and formaldehyde (2.27 mL, 30.5 mmol) (37% in water), and the mixture was stirred at 50° C. for 16 h. The mixture was concentrated in vacuo to afford 3-methyl-2'-thioxo-2,2',3,3',5',6'-hexahydrospiro[indene-1,7'-pyrano[2,3-d]pyrimidin]-4'(1'H)-one (Int 25a) as a solid, which was used in the next step directly without further purification. MS (ESI): m/z (M+H)+301.

Step B: 3-methyl-2'-(methylthio)-2,3,5',6'-tetrahydrospiro[indene-1,7'-pyrano[2,3-d]pyrimidin]-4'(3'H)-one (Int 25b)

To a mixture of 3-methyl-2'-thioxo-2,2',3,3',5',6'-hexahydrospiro[indene-1,7'-pyrano[2,3-d]pyrimidin]-4'(1'H)-one (Int 25a) (4.58 g, 15.3 mmol) in MeCN (40 mL) was added $K_2CO_3$ (2.74 g, 19.8 mmol) and MeI (0.953 mL, 15.3 mmol), and the mixture was stirred at 20° C. for 0.5 h. The reaction mixture was quenched with water (150 mL), and extracted with (DCM/MeOH=10/1) (2×130 mL). The combined organic layers were washed with brine (100 mL), dried over $Na_2SO_4$, filtered and the solvent was evaporated under reduced pressure to afford 3-methyl-2'-(methylthio)-2,3,5',6'-tetrahydrospiro[indene-1,7'-pyrano[2,3-d]pyrimidin]-4'(3'H)-one (Int 25b) which was used in the next step directly without further purification. MS (ESI): m/z (M+H)+315.

Step C: 3-methyl-2'-(methylthio)-2,3,5',6'-tetrahydrospiro[indene-1,7'-pyrano[2,3-d]pyrimidin]-4'-yl trifluoromethanesulfonate ((Int 25c)

To a stirred mixture of 3-methyl-2'-(methylthio)-2,3,5',6'-tetrahydrospiro[indene-1,7'-pyrano[2,3-d]pyrimidin]-4'(3'H)-one (Int 25b) (200 mg, 0.636 mmol) in DCM (5 mL) was added DIEA (0.333 mL, 1.91 mmol), then $Tf_2O$ (0.140 mL, 0.827 mmol) was added dropwise at 0° C., and the mixture was stirred at 0° C. for 0.5 h. The mixture was dissolved in water (20 mL) and extracted with DCM (20 mL×2). The combined organic layers were dried over $Na_2SO_4$, filtered and concentrated in vacuo. The residue was purified by flash silica gel chromatography with an eluent of 0~10% EtOAc/Pet. ether gradient to afford 3-methyl-2'-(methylthio)-2,3,5',6'-tetrahydrospiro[indene-1,7'-pyrano[2,3-d]pyrimidin]-4'-yl trifluoromethanesulfonate (Int 25c). MS (ESI): m/z $(M+H)^+$447.

Step D: (2S)-tert-butyl 2-(cyanomethyl)-4-(3-methyl-2'-(methylthio)-2,3,5',6'-tetrahydrospiro[indene-1,7'-pyrano[2,3-d]pyrimidin]-4'-yl)piperazine-1-carboxylate (Int 25d)

To a solution of 3-methyl-2'-(methylthio)-2,3,5',6'-tetrahydrospiro[indene-1,7'-pyrano[2,3-d]pyrimidin]-4'-yl trifluoromethanesulfonate (Int 25c) (200 mg, 0.448 mmol) in MeCN (5 mL) was added DIEA (0.391 mL, 2.24 mmol) and (S)-2-(piperazin-2-yl)acetonitrile hydrochloride (109 mg, 0.672 mmol), and the mixture was stirred at 80° C. for 1.5 h. The mixture was cooled, and $Boc_2O$ (0.312 mL, 1.34 mmol) was added, then the mixture was stirred at 20° C. for 2 h. The mixture was concentrated in vacuo, and the residue was purified by flash silica gel chromatography with an eluent of 0~10% EtOAc/Pet. ether gradient to afford (2S)-tert-butyl 2-(cyanomethyl)-4-(3-methyl-2'-(methylthio)-2,3,5',6'-tetrahydrospiro[indene-1,7'-pyrano[2,3-d]pyrimidin]-4'-yl)piperazine-1-carboxylate (Int 25d). MS (ESI): m/z $(M+H)^+$522.

Step E: (2S)-tert-butyl 2-(cyanomethyl)-4-(3-methyl-2'-(methylsulfonyl)-2,3,5',6'-tetrahydrospiro[indene-1,7'-pyrano[2,3-d]pyrimidin]-4'-yl)piperazine-1-carboxylate (Int 25e)

To a mixture of (2S)-tert-butyl 2-(cyanomethyl)-4-(3-methyl-2'-(methylthio)-2,3,5',6'-tetrahydrospiro[indene-1,7'-pyrano[2,3-d]pyrimidin]-4'-yl)piperazine-1-carboxylate (Int 25d) (220 mg, 0.422 mmol) in DCM (5 mL) was added m-CPBA (273 mg, 1.27 mmol), and the mixture was stirred at 20° C. for 1 h. The mixture was dissolved in water (20 mL), basified with saturated aqueous $NaHCO_3$ to pH 9, and extracted with DCM (20 mL×2). The combined organic layers were dried over $Na_2SO_4$, filtered and concentrated in vacuo, and the residue was purified by flash silica gel chromatography (with an eluent of 10~60% EtOAc/Pet. ether gradient at 30 mL/min) to afford (2S)-tert-butyl 2-(cyanomethyl)-4-(3-methyl-2'-(methylsulfonyl)-2,3,5',6'-tetrahydrospiro[indene-1,7'-pyrano[2,3-d]pyrimidin]-4'-yl)piperazine-1-carboxylate (Int 25e). MS (ESI): m/z $(M+H)^+$554.

Step F: (2S)-tert-butyl 2-(cyanomethyl)-4-(3-methyl-2'-(((S)-1-methylpyrrolidin-2-yl)methoxy)-2,3,5',6'-tetrahydrospiro[indene-1,7'-pyrano[2,3-d]pyrimidin]-4'-yl)piperazine-1-carboxylate (Int 25f)

To a solution of (S)-(1-methylpyrrolidin-2-yl)methanol (183 mg, 1.59 mmol) in THF (3 mL) was added sodium tert-butoxide (0.497 mL, 0.993 mmol) (2M in THF) dropwise at 0° C. under $N_2$ atmosphere, and the mixture was stirred at 0° C. for 10 min. Then (2S)-tert-butyl 2-(cyanomethyl)-4-(3-methyl-2'-(methylsulfonyl)-2,3,5',6'-tetrahydrospiro[indene-1,7'-pyrano[2,3-d]pyrimidin]-4'-yl)piperazine-1-carboxylate (Int 25e) (220 mg, 0.397 mmol) in THF (2 mL) was added dropwise. The mixture was stirred at 0° C. for 30 min. The mixture was dissolved in water (25 mL), and extracted with EtOAc (25 mL×2). The combined organic layers were dried over $Na_2SO_4$, filtered and concentrated in vacuo to afford (2S)-tert-butyl 2-(cyanomethyl)-4-(3-methyl-2'-(((S)-1-methylpyrrolidin-2-yl)methoxy)-2,3,5',6'-tetrahydrospiro[indene-1,7'-pyrano[2,3-d]pyrimidin]-4'-yl)piperazine-1-carboxylate (Int 25f).

Step G: 2-((2S)-4-(3-methyl-2'-(((S)-1-methylpyrrolidin-2-yl)methoxy)-2,3,5',6'-tetrahydrospiro[indene-1,7'-pyrano[2,3-d]pyrimidin]-4'-yl)piperazin-2-yl) acetonitrile (Int 25g)

To a solution of (2S)-tert-butyl 2-(cyanomethyl)-4-(3-methyl-2'-(((S)-1-methylpyrrolidin-2-yl)methoxy)-2,3,5',6'-tetrahydrospiro[indene-1,7'-pyrano[2,3-d]pyrimidin]-4'-yl) piperazine-1-carboxylate (Int 25f) (220 mg, 0.374 mmol) in DCM (3 mL) was added TFA (2 mL, 26.0 mmol), and the mixture was stirred at 20° C. for 1 h. The mixture was concentrated in vacuo to afford 2-((2S)-4-(3-methyl-2'-(((S)-1-methylpyrrolidin-2-yl)methoxy)-2,3,5',6'-tetrahydrospiro [indene-1,7'-pyrano[2,3-d]pyrimidin]-4'-yl)piperazin-2-yl) acetonitrile (Int 25g). MS (ESI): m/z $(M+H)^+$489.

Step H: 2-((2S)-1-acryloyl-4-(3-methyl-2'-(((S)-1-methylpyrrolidin-2-yl)methoxy)-2,3,5',6'-tetrahydrospiro[indene-1,7'-pyrano[2,3-d]pyrimidin]-4'-yl) piperazin-2-yl)acetonitrile (Ex. 25a/b/c/d)

To a stirred solution of 2-((2S)-4-(3-methyl-2'-(((S)-1-methylpyrrolidin-2-yl)methoxy)-2,3,5',6'-tetrahydrospiro [indene-1,7'-pyrano[2,3-d]pyrimidin]-4'-yl)piperazin-2-yl) acetonitrile (Int 27g) (183 mg, 0.375 mmol) in DCM (3 mL) was added DIEA (0.327 mL, 1.87 mmol), then acryloyl chloride (50.8 mg, 0.562 mmol) was added dropwise, and the mixture was stirred at 0° C. for 10 min. The mixture was concentrated in vacuo, and the residue was purified by Prep-HPLC (Column: Agela DuraShell C18 150 mm×25 mm, 5 um, Condition: water (0.04% $NH_3H_2O$+10 mM $NH_4HCO_3$)-ACN Begin B: 40, End B: 70 Gradient Time (min): 10, 100% B Hold Time (min) 2, FlowRate (mL/min): 25, Injections: 12) to afford 2-((2S)-1-acryloyl-4-(3-methyl-2'-(((S)-1-methylpyrrolidin-2-yl)methoxy)-2,3,5',6'-tetrahydrospiro[indene-1,7'-pyrano[2,3-d]pyrimidin]-4'-yl)piperazin-2-yl)acetonitrile (Ex 25a/b/c/d) as a racemic mixture. MS (ESI): m/z $(M+H)^+$543.

The racemic mixture (100 mg, 0.184 mmol) was separated by preparative SFC (Column E; Condition: 0.1% $NH_3H_2O$ MeOH, Begin B: 40%, End B: 40%, Gradient Time (min), 100% B Hold Time (min), FlowRate (mL/min): 60, Injections: 60) to afford 2-((2S)-1-acryloyl-4-(3-methyl-2'-(((S)-1-methylpyrrolidin-2-yl)methoxy)-2,3,5',6'-tetrahydrospiro[indene-1,7'-pyrano[2,3-d]pyrimidin]-4'-yl)piperazin-2-yl)acetonitrile (50 mg, 0.092 mmol) (Ex 25P1, the first eluting isomer) and 2-((2S)-1-acryloyl-4-(3-methyl-2'-(((S)-1-methylpyrrolidin-2-yl)methoxy)-2,3,5',6'-tetrahydrospiro[indene-1,7'-pyrano[2,3-d]pyrimidin]-4'-yl)piperazin-2-yl)acetonitrile (30 mg, 0.055 mmol) (Ex 25P2, the second eluting isomer), both as oils.

2-((2S)-1-acryloyl-4-(3-methyl-2'-(((S)-1-methylpyrrolidin-2-yl)methoxy)-2,3,5',6'-tetrahydrospiro[indene-1,7'-pyrano[2,3-d]pyrimidin]-4'-yl)piperazin-2-yl)acetonitrile (50 mg, 0.092 mmol) (Ex 25P1) was separated by SFC (Column J, Condition: 0.1% $NH_3H_2O$ EtOH) to afford 2-((2S)-1-acryloyl-4-(3-methyl-2'-(((S)-1-methylpyrrolidin-2-yl)methoxy)-2,3,5',6'-tetrahydrospiro[indene-1,7'-pyrano [2,3-d]pyrimidin]-4'-yl)piperazin-2-yl)acetonitrile (Ex. 25a): $^1$H NMR (400 MHz, MeOD) δ 7.48-7.12 (m, 4H), 6.87-6.79 (m, 1H), 6.30-6.25 (m, 1H), 5.82 (br d, J=11.0 Hz, 1H), 4.83-4.47 (m, 2H), 4.32 (br d, J=5.9 Hz, 2H), 4.12-4.09 (m, 3H), 3.68 (br s, 1H), 3.42-3.39 (m, 1H), 3.29-3.21 (m, 1H), 3.14-3.12 (m, 2H), 3.02-2.80 (m, 3H), 2.76-2.74 (m, 1H), 2.66-2.61 (m, 1H), 2.58-2.50 (m, 3H), 2.44 (q, J=9.3 Hz, 1H), 2.16-1.88 (m, 4H), 1.87-1.77 (m, 2H), 1.76-1.64 (m, 1H), 1.37 (d, J=6.7 Hz, 3H). And 2-((2S)-1-acryloyl-4-(3-methyl-2'-(((S)-1-methylpyrrolidin-2-yl)methoxy)-2,3,5',6'-tetrahydrospiro[indene-1,7'-pyrano[2,3-d]pyrimidin]-4'-yl)piperazin-2-yl)acetonitrile (Ex 25b): $^1$H NMR (400 MHz, MeOD) δ 7.49-7.15 (m, 4H), 6.85-6.81 (m, 1H), 6.30-6.26 (m, 1H), 5.83 (br d, J=11.0 Hz, 1H), 4.83-4.45 (m, 2H), 4.36-4.20 (m, 2H), 4.19-3.98 (m, 2H), 3.74 (br s, 1H), 3.48-3.45 (m, 2H), 3.21-2.73 (m, 7H), 2.68-2.65 (m, 1H), 2.50 (s, 3H), 2.43-2.28 (m, 2H), 2.15-1.99 (m, 2H), 1.86-1.59 (m, 4H), 1.34 (d, J=6.7 Hz, 3H).

2-((2S)-1-acryloyl-4-(3-methyl-2'-(((S)-1-methylpyrrolidin-2-yl)methoxy)-2,3,5',6'-tetrahydrospiro[indene-1,7'-pyrano[2,3-d]pyrimidin]-4'-yl)piperazin-2-yl)acetonitrile (30 mg, 0.055 mmol) (Ex 25P2) was separated by SFC (Column K, Condition: 0.1% $NH_3H_2O$ MeOH, Begin B: 50, End B: 50 Gradient Time (min), 100% B Hold Time (min), FlowRate (mL/min) 80, Injections 170) to afford 2-((2S)-1-acryloyl-4-(3-methyl-2'-(((S)-1-methylpyrrolidin-2-yl) methoxy)-2,3,5',6'-tetrahydrospiro[indene-1,7'-pyrano[2,3-d]pyrimidin]-4'-yl)piperazin-2-yl)acetonitrile (Ex 25c): 1H NMR (400 MHz, MeOD) δ 7.48-7.13 (m, 4H), 6.81 (br s, 1H), 6.30-6.26 (m, 1H), 5.83 (br d, J=10.6 Hz, 1H), 4.79-4.49 (m, 2H), 4.45-4.29 (m, 2H), 4.27-3.97 (m, 3H), 3.59-3.34 (m, 2H), 3.29-3.09 (m, 4H), 3.03 (br s, 2H), 2.93-2.82 (m, 1H), 2.75 (br s, 1H), 2.67-2.55 (m, 4H), 2.19-2.06 (m, 2H), 2.05-1.83 (m, 4H), 1.82-1.71 (m, 1H), 1.38 (d, J=7.0 Hz, 3H). And 2-((2S)-1-acryloyl-4-(3-methyl-2'-(((S)-1-methylpyrrolidin-2-yl)methoxy)-2,3,5',6'-tetrahydrospiro [indene-1,7'-pyrano[2,3-d]pyrimidin]-4'-yl)piperazin-2-yl) acetonitrile (Ex 25d): $^1$H NMR (400 MHz, MeOD) δ 7.48-7.16 (m, 4H), 6.82 (br s, 1H), 6.31-6.26 (m, 1H), 5.84 (br d, J=9.4 Hz, 1H), 4.82-4.49 (m, 2H), 4.39-4.17 (m, 3H), 4.15-3.91 (m, 2H), 3.55-3.36 (m, 2H), 3.26-3.03 (m, 4H), 3.01-2.71 (m, 3H), 2.65-2.63 (m, 1H), 2.57-2.30 (m, 5H), 2.14-2.01 (m, 2H), 1.95-1.61 (m, 4H), 1.35 (d, J=7.0 Hz, 3H).

Examples 26-28 in the table below were prepared using procedures similar to those described in example 25 from the indicated alkenes.

| Ex. | Alkene Precursor | Structure | Compound Name | [M + H]+ Found | Purification Conditions |
|---|---|---|---|---|---|
| 26a | Int A11 | 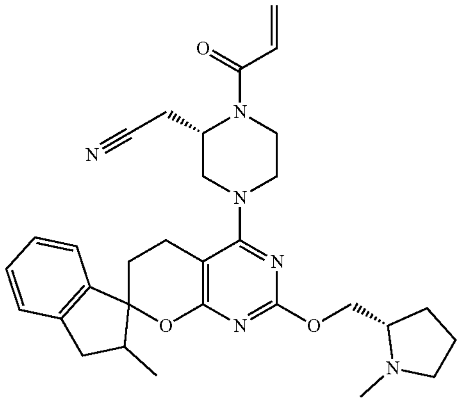 [SMILES: C=CC(=O)N1CCN(c2nc(OC[C@@H]3CCCN3C)nc3c2CCC2(O3)c3ccccc3CC2C)C[C@@H]1CC#N]<br>Peak 1 | 2-((2S)-4-acryloyl-1-(2-methyl-2'-(((S)-1-methylpyrrolidin-2-yl)methoxy)-2,3,5',6'-tetrahydrospiro[indene-1,7'-pyrano[2,3-d]pyrimidin]-4'-yl)piperazin-2-yl)acetonitrile | 543 | Column L, Condition: 0.1% $NH_4OH$/ IPA |
| 26b | Int A11 | 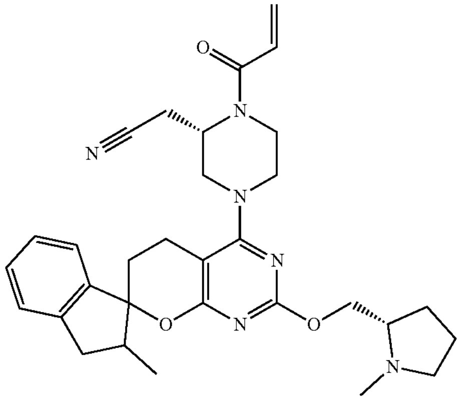 [SMILES: C=CC(=O)N1CCN(c2nc(OC[C@@H]3CCCN3C)nc3c2CCC2(O3)c3ccccc3CC2C)C[C@@H]1CC#N]<br>Peak 3 | 2-((2S)-4-acryloyl-1-(2-methyl-2'-(((S)-1-methylpyrrolidin-2-yl)methoxy)-2,3,5',6'-tetrahydrospiro[indene-1,7'-pyrano[2,3-d]pyrimidin]-4'-yl)piperazin-2-yl)acetonitrile | 543 | |
| 26c | Int A11 | 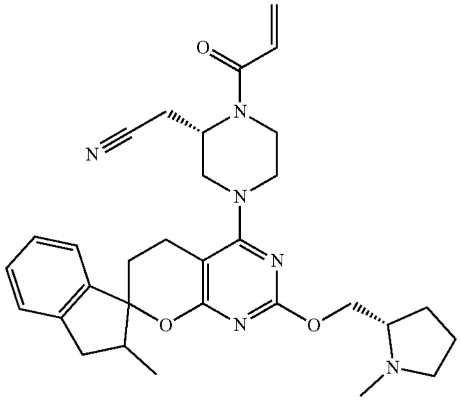 [SMILES: C=CC(=O)N1CCN(c2nc(OC[C@@H]3CCCN3C)nc3c2CCC2(O3)c3ccccc3CC2C)C[C@@H]1CC#N]<br>Peak 2, then Peak 1 | 2-((2S)-4-acryloyl-1-(2-methyl-2'-(((S)-1-methylpyrrolidin-2-yl)methoxy)-2,3,5',6'-tetrahydrospiro[indene-1,7'-pyrano[2,3-d]pyrimidin]-4'-yl)piperazin-2-yl)acetonitrile | 543 | First Separation: Column L, Condition: 0.1% $NH_4OH$/ IPA |

-continued

| Ex. | Alkene Precursor | Structure | Compound Name | $[M + H]^+$ Found | Purification Conditions |
|---|---|---|---|---|---|
| 26d | Int A11 | 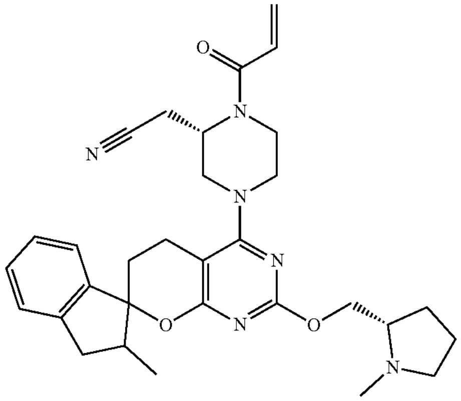 [SMILES: C=CC(=O)N1CCN(c2nc(OC[C@@H]3CCCN3C)nc3c2CCC2(O3)c3ccccc3CC2C)C[C@@H]1CC#N] Peak 2, then Peak 2 | 2-((2S)-4-acryloyl-1-(2-methyl-2'-(((S)-1-methylpyrrolidin-2-yl)methoxy)-2,3,5',6'-tetrahydrospiro[indene-1,7'-pyrano[2,3-d]pyrimidin]-4'-yl)piperazin-2-yl)acetonitrile | 543 | Second Separation: Column E; Condition: 0.1% $NH_4OH$/ EtOH |
| 27a | Int A12 | 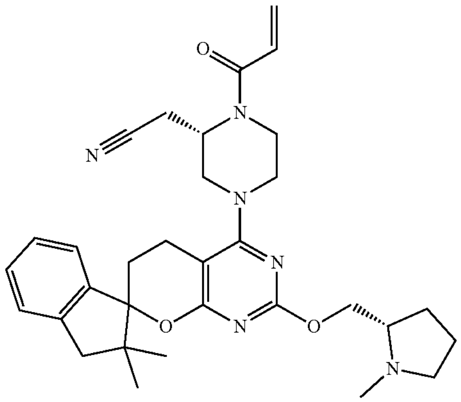 [SMILES: C=CC(=O)N1CCN(c2nc(OC[C@@H]3CCCN3C)nc3c2CCC2(O3)c3ccccc3CC2(C)C)C[C@@H]1CC#N] Peak 1 | 2-((2S)-1-acryloyl-4-(2,2-dimethyl-2'-(((S)-1-methylpyrrolidin-2-yl)methoxy)-2,3,5',6'-tetrahydrospiro[indene-1,7'-pyrano[2,3-d]pyrimidin]-4'-yl)piperazin-2-yl)acetonitrile | 557 | Column F Condition: 0.1% $NH_4OH$/ EtOH |
| 27b | Int A12 | 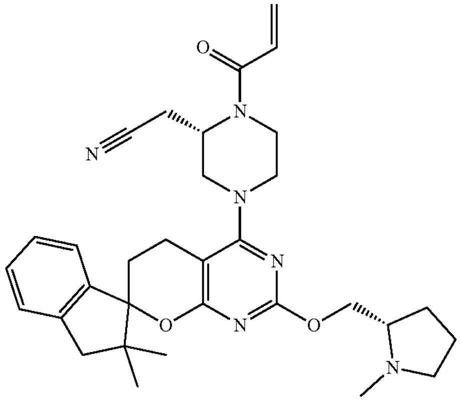 [SMILES: C=CC(=O)N1CCN(c2nc(OC[C@@H]3CCCN3C)nc3c2CCC2(O3)c3ccccc3CC2(C)C)C[C@@H]1CC#N] Peak 2 | 2-((2S)-1-acryloyl-4-(2,2-dimethyl-2'-(((S)-1-methylpyrrolidin-2-yl)methoxy)-2,3,5',6'-tetrahydrospiro[indene-1,7'-pyrano[2,3-d]pyrimidin]-4'-yl)piperazin-2-yl)acetonitrile | 557 | |

-continued

| Ex. | Alkene Precursor | Structure | Compound Name | [M + H]+ Found | Purification Conditions |
|---|---|---|---|---|---|
| 28a | Int A13 | 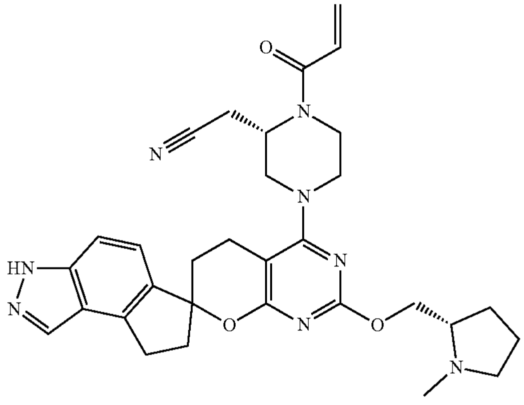 [SMILES: C=CC(=O)N1CCN(c2nc(OC[C@@H]3CCCN3C)nc3c2CCC2(CCc4c2ccc2[nH]ncc42)O3)C[C@@H]1CC#N] Peak 2 | 2-((2S)-1-acryloyl-4-(2'-(((S)-1-methylpyrrolidin-2-yl)methoxy)-5',6',7,8-tetrahydro-3H-spiro[cyclopenta[e]indazole-6,7'-pyrano[2,3-d]pyrimidin]-4'-yl)piperazin-2-yl)acetonitrile | 569 | Column E; Condition: 0.1% $NH_4OH$/EtOH |
| 28b | Int A13 | 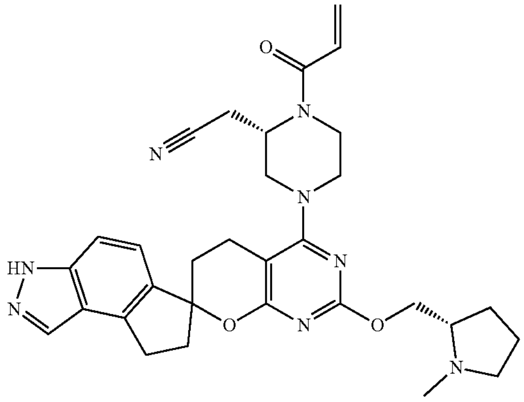 [SMILES: C=CC(=O)N1CCN(c2nc(OC[C@@H]3CCCN3C)nc3c2CCC2(CCc4c2ccc2[nH]ncc42)O3)C[C@@H]1CC#N] Peak 1 | 2-((2S)-1-acryloyl-4-(2'-(((S)-1-methylpyrrolidin-2-yl)methoxy)-5',6',7,8-tetrahydro-3H-spiro[cyclopenta[e]indazole-6,7'-pyrano[2,3-d]pyrimidin]-4'-yl)piperazin-2-yl)acetonitrile | 569 | |

Example 29: 2-((S)-1-acryloyl-4-(2'-(((S)-1-methylpyrrolidin-2-yl)methoxy)-1,3,5',6'-tetrahydrospiro[indene-2,7'-pyrano[2,3-d]pyrimidin]-4'-yl)piperazin-2-yl)acetonitrile

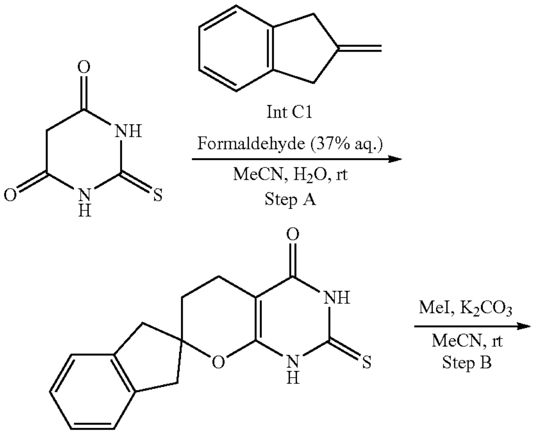

Int 29a

-continued

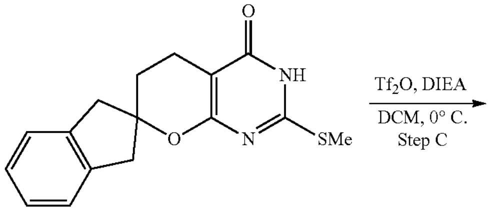

Int 29b

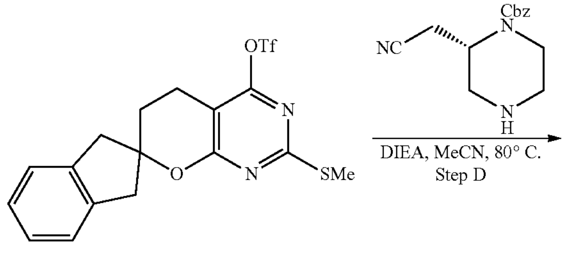

Int 25c

-continued

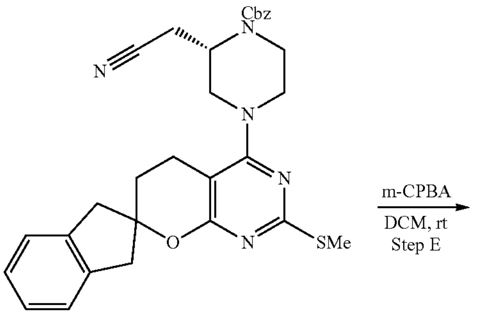

Int 29d

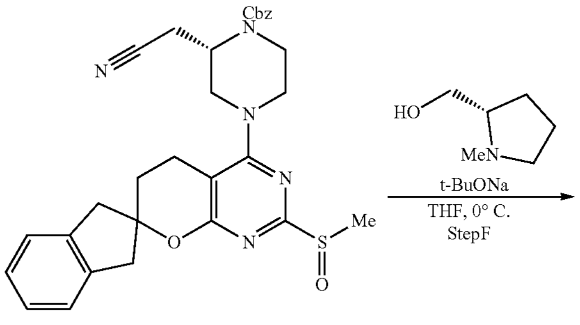

Int 29e

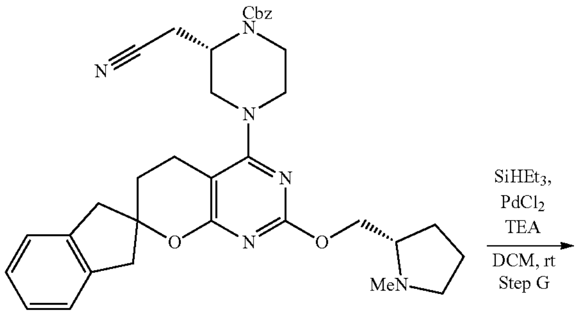

Int 29f

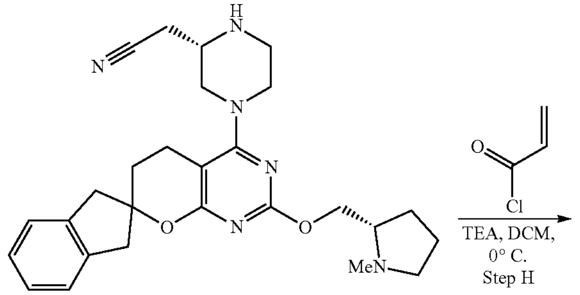

Int 29g

-continued

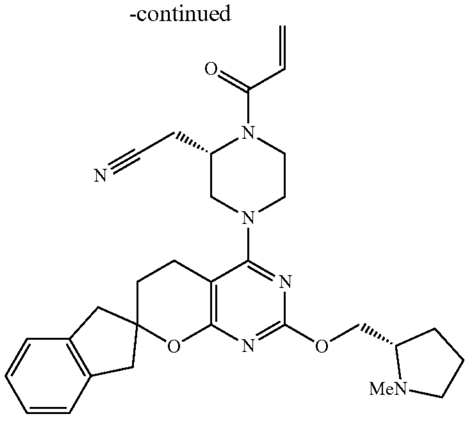

Ex 29

Step A: 2'-thioxo-1,2',3,3',5',6'-hexahydrospiro[indene-2,7'-pyrano[2,3-d]pyrimidin]-4'(1'H)-one (Int 29a)

A mixture of 2-methylene-2,3-dihydro-1H-indene (Int C1, 1.8 g, 13.8 mmol), 2-thioxodihydropyrimidine-4,6(1H, 5H)-dione (2.99 g, 20.7 mmol) and formaldehyde (37% in water, 2.06 mL, 27.7 mmol) in water (30 mL) and dioxane (8.0 mL) was stirred at 25° C. for 17 h. The mixture was filtered and the cake was dried in vacuo to give 2'-thioxo-1,2',3,3',5',6'-hexahydrospiro[indene-2,7'-pyrano[2,3-d]pyrimidin]-4'(1'H)-one (Int 29a). MS (ESI): m/z (M+H)+287.

Step B: 2'-(methylthio)-1,3,5',6'-tetrahydrospiro[indene-2,7'-pyrano[2,3-d]pyrimidin]-4'(3'H)-one (Int 29b)

A mixture of 2'-thioxo-1,2',3,3',5',6'-hexahydrospiro[indene-2,7'-pyrano[2,3-d]pyrimidin]-4'(1'H)-one (Int 29a) (2.2 g, 7.68 mmol), potassium carbonate (1.38 g, 9.99 mmol) and methyl iodide (0.576 mL, 9.22 mmol) in MeCN (40 mL) was stirred at 25° C. for 1 h to give a yellow mixture. The reaction mixture was quenched with brine (50 mL), and extracted with DCM/MeOH=10/1 (3×50 mL). The combined organic layers were washed with brine (100 mL), dried over $Na_2SO_4$, filtered and the solvent was evaporated under reduced pressure to give 2'-(methylthio)-1,3,5',6'-tetrahydrospiro[indene-2,7'-pyrano[2,3-d]pyrimidin]-4'(3'H)-one (Int 29b). MS (ESI): m/z (M+H)*301.

Step C: 2'-(methylthio)-1,3,5',6'-tetrahydrospiro[indene-2,7'-pyrano[2,3-d]pyrimidin]-4'-yl trifluoromethanesulfonate (Int 29c)

To a mixture of 2'-(methylthio)-1,3,5',6'-tetrahydrospiro[indene-2,7'-pyrano[2,3-d]pyrimidin]-4'(3'H)-one (Int 29b) (800 mg, 2.66 mmol) and N-ethyl-N-isopropylpropan-2-amine (1033 mg, 7.99 mmol) in DCM (100 mL) was added trifluoromethanesulfonic anhydride (1127 mg, 4.00 mmol) at 0° C. After addition, the mixture was stirred at 0° C. for 10 min to give yellow mixture. The solvent was removed under reduced pressure, and the residue was dissolved in water (50 mL) and EtOAc (50 mL). The organic layer was separated and the aqueous was re-extracted with EtOAc (50 mL×3), and the combined organic layers were washed with brine (100 mL), dried over anhydrous $Na_2SO_4$, filtered and concentrated under reduced pressure. The residue was purified by flash silica gel chromatography with an eluent of 4% ethyl acetate/Pet. ether gradient to give 2'-(methylthio)-1,3,5',6'-tetrahydrospiro[indene-2,7'-pyrano[2,3-d]pyrimidin]-4'-yl trifluoromethanesulfonate (Int 29c).

Step D: benzyl (S)-2-(cyanomethyl)-4-(2'-(methylthio)-1,3,5',6'-tetrahydrospiro[indene-2,7'-pyrano[2,3-d]pyrimidin]-4'-yl)piperazine-1-carboxylate (Int 29d)

A mixture of 2'-(methylthio)-1,3,5',6'-tetrahydrospiro[indene-2,7'-pyrano[2,3-d]pyrimidin]-4'-yl trifluoromethanesulfonate (Int 29c) (400 mg, 0.925 mmol), (S)-benzyl 2-(cyanomethyl)piperazine-1-carboxylate (360 mg, 1.39 mmol) and DIEA (0.485 mL, 2.77 mmol) in MeCN (10 mL) was stirred at 80° C. for 17 h to give a yellow mixture. The solvent was removed under reduced pressure, and the residue was dissolved in water (50 mL) and EtOAc (50 mL). The organic layer was separated and the aqueous layer was re-extracted with EtOAc (50 mL×3), and the combined organic layers were washed with brine (100 mL), dried over anhydrous $Na_2SO_4$, filtered and concentrated under reduced pressure. The residue was purified by preparative TLC (ethyl acetate/Pet. ether=1/3, v/v) to give benzyl (S)-2-(cyanomethyl)-4-(2'-(methylthio)-1,3,5',6'-tetrahydrospiro[indene-2,7'-pyrano[2,3-d]pyrimidin]-4'-yl)piperazine-1-carboxylate (Int 29d) MS (ESI): m/z (M+H)+542.

Step E: benzyl (2S)-2-(cyanomethyl)-4-(2'-(methylsulfinyl)-1,3,5',6'-tetrahydrospiro[indene-2,7'-pyrano[2,3-d]pyrimidin]-4'-yl)piperazine-1-carboxylate (Int 29e)

A mixture of benzyl (S)-2-(cyanomethyl)-4-(2'-(methylthio)-1,3,5',6'-tetrahydrospiro[indene-2,7'-pyrano[2,3-d]pyrimidin]-4'-yl)piperazine-1-carboxylate (Int 29d) (300 mg, 0.554 mmol) and m-CPBA (155 mg, 0.720 mmol) in DCM (10 mL) was stirred at 25° C. for 1 h to give a yellow mixture. The solvent was removed under reduced pressure, and the residue was dissolved in water (30 mL) and EtOAc (30 mL). The organic layer was separated and the aqueous was re-extracted with EtOAc (30 mL×3), and the combined organic layers were washed with brine (100 mL), dried over anhydrous $Na_2SO_4$, filtered and concentrated under reduced pressure to give crude. The crude product was purified by preparative TLC (ethyl acetate/Pet. ether=1/1, v/v) to give benzyl (2S)-2-(cyanomethyl)-4-(2'-(methylsulfinyl)-1,3,5',6'-tetrahydrospiro[indene-2,7'-pyrano[2,3-d]pyrimidin]-4'-yl)piperazine-1-carboxylate (Int 29e) MS (ESI): m/z (M+H)*558.

Step F: benzyl (S)-2-(cyanomethyl)-4-(2'-(((S)-1-methylpyrrolidin-2-yl methoxy)-1,3,5',6'-tetrahydrospiro[indene-2,7'-pyrano[2,3-d]pyrimidin]-4'-yl)piperazine-1-carboxylate (Int 29f)

To a solution of (S)-(1-methylpyrrolidin-2-yl)methanol (207 mg, 1.793 mmol) in THF (3.0 mL) was added sodium 2-methylpropan-2-olate (0.448 mL, 0.897 mmol) at 0° C. under $N_2$ atmosphere. Then benzyl (2S)-2-(cyanomethyl)-4-(2'-(methylsulfinyl)-1,3,5',6'-tetrahydrospiro[indene-2,7'-pyrano[2,3-d]pyrimidin]-4'-yl)piperazine-1-carboxylate (Int 29e) (250 mg, 0.448 mmol) in THF (3.00 mL) was added. The mixture was stirred at 0° C. for 0.5 h. The reaction mixture was quenched with water (10 mL) and extracted with EtOAc (10 mL×3). The combined organic phases were washed with brine (30 mL), dried over anhydrous $Na_2SO_4$, filtered and concentrated under reduced pressure to give crude benzyl (S)-2-(cyanomethyl)-4-(2'-(((S)-1-methylpyrrolidin-2-yl)methoxy)-1,3,5',6'-tetrahydrospiro[indene-2,7'-pyrano[2,3-d]pyrimidin]-4'-yl)piperazine-1-carboxylate (Int 29f) MS (ESI): m/z (M+H)+609.

Step G: 2-((S)-4-(2'-(((S)-1-methylpyrrolidin-2-yl)methoxy)-1,3,5',6'-tetrahydrospiro[indene-2,7'-pyrano[2,3-d]pyrimidin]-4'-yl)piperazin-2-yl)acetonitrile (Int 29g)

To a stirred mixture of benzyl (S)-2-(cyanomethyl)-4-(2'-(((S)-1-methylpyrrolidin-2-yl)methoxy)-1,3,5',6'-tetrahydrospiro[indene-2,7'-pyrano[2,3-d]pyrimidin]-4'-yl)piperazine-1-carboxylate (Int 29f) (20 mg, 0.033 mmol) in DCM (2 mL) was added triethylsilane (0.026 mL, 0.164 mmol), TEA (0.023 mL, 0.164 mmol) and palladium(II) chloride (2.91 mg, 0.016 mmol). Then the mixture was stirred at 25° C. for 1 h. The mixture was filtered and the filtrate was concentrated to give the crude as an oil. The oil was purified by preparative HPLC (Column: YMC-Actus Triart C18 100 mm×30 mm×5 um; Condition: water (0.1% TFA)-ACN Begin B 17, End B 47; Gradient Time (min): 11; 100% B Hold Time (min): 1.1; FlowRate (mL/min) 40) to give 2-((S)-4-(2'-(((S)-1-methylpyrrolidin-2-yl)methoxy)-1,3,5',6'-tetrahydrospiro[indene-2,7'-pyrano[2,3-d]pyrimidin]-4'-yl)piperazin-2-yl)acetonitrile (Int 29g) MS (ESI): m/z (M+H)+475.

Step H: 2-((S)-1-acryloyl-4-(2'-(((S)-1-methylpyrrolidin-2-yl)methoxy)-1,3,5',6'-tetrahydrospiro[indene-2,7'-pyrano[2,3-d]pyrimidin]-4'-yl)piperazin-2-yl)acetonitrile (Ex. 29)

To a mixture of 2-((S)-4-(2'-(((S)-1-methylpyrrolidin-2-yl)methoxy)-1,3,5',6'-tetrahydrospiro[indene-2,7'-pyrano[2,3-d]pyrimidin]-4'-yl)piperazin-2-yl)acetonitrile (Int 29g) (40 mg, 0.084 mmol) and TEA (0.035 mL, 0.253 mmol) in DCM (2 mL) was added acryloyl chloride (11.44 mg, 0.126 mmol) at 0° C. After addition, the mixture was stirred at 0° C. for 0.5 h. LCMS showed desired product was generated. The mixture was concentrated and the residue was purified by preparative HPLC (Column Agela: DuraShell C18 150 mm×25 mm, 5 um; Condition: water (0.05% $NH_3H_2O$+10 mM $NH_4HCO_3$)-ACN to afford 2-((S)-1-acryloyl-4-(2'-(((S)-1-methylpyrrolidin-2-yl)methoxy)-1,3,5',6'-tetrahydrospiro[indene-2,7'-pyrano[2,3-d]pyrimidin]-4'-yl)piperazin-2-yl)acetonitrile. (Ex 29): MS (ESI): m/z $(M+H)^+$518. $^1H$ NMR (500 MHz, METHANOL-$d_4$) δ 7.25-7.14 (m, 4H), 6.84 (br s, 1H), 6.31 (br d, J=17.0 Hz, 1H), 5.86 (br d, J=10.5 Hz, 1H), 5.27-4.99 (m, 3H), 4.41-4.05 (m, 4H), 3.28-3.15 (m, 7H), 3.03-2.79 (m, 5H), 2.58 (s, 3H), 2.50-2.53 (m, 1H), 2.21-2.09 (m, 3H), 1.91-1.83 (m, 2H), 1.77-1.69 (m, 1H).

Example 30: 2-((S)-1-acryloyl-4-(2'-(((S)-1-methylpyrrolidin-2-yl)methoxy)-5',6'-dihydrospiro[fluorene-9,7'-pyrano[2,3-d]pyrimidin]-4'-yl)piperazin-2-yl)acetonitrile

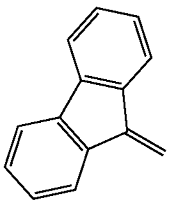

Int A14

+

-continued

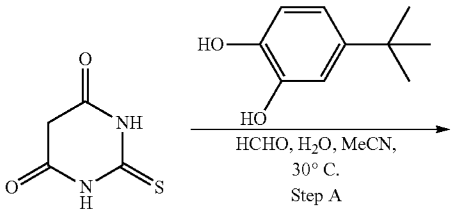

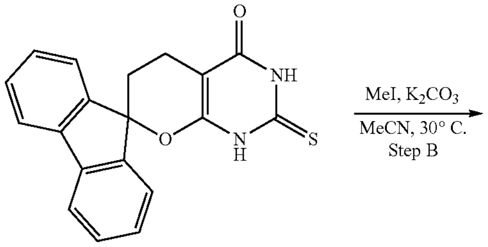

Int 30a

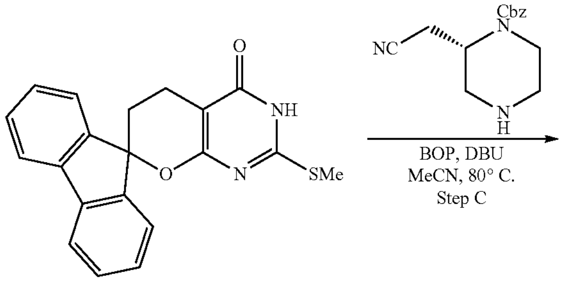

Int 30b

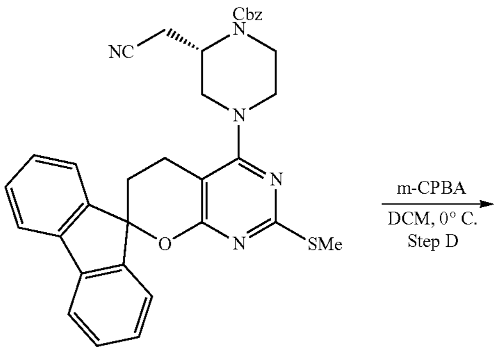

Int 30c

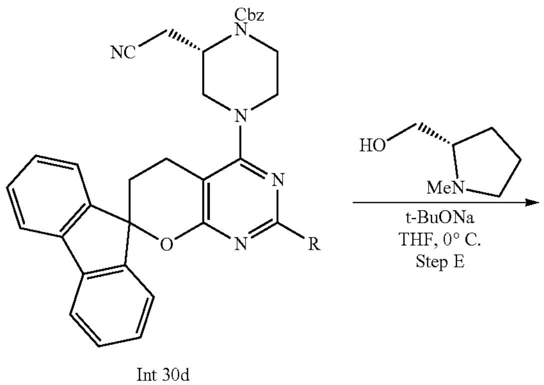

Int 30d
R = SOMe or $SO_2Me$

-continued

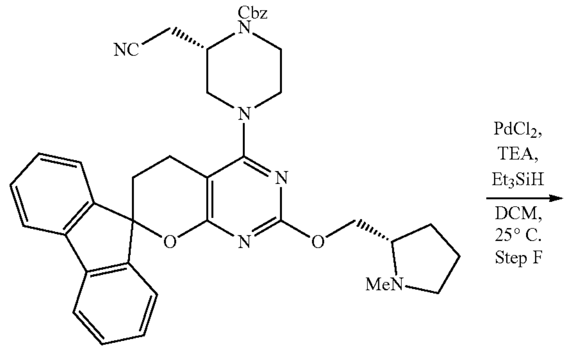

Int 30e

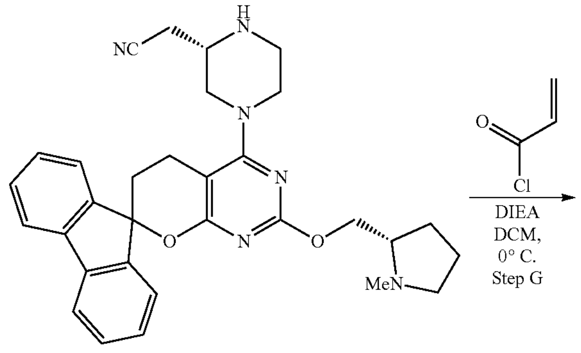

Int 30f

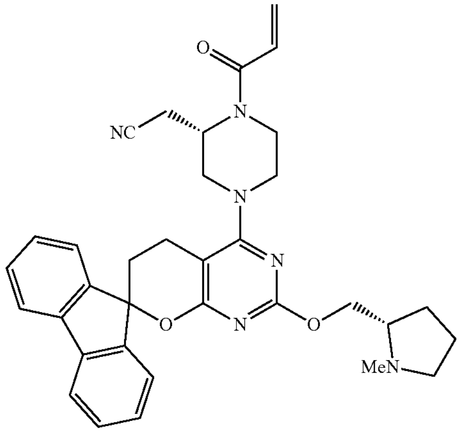

Ex 30

Step A: 2'-thioxo-2',3',5',6'-tetrahydrospiro[fluorene-9,7'-pyrano[2,3-d]pyrimidin]-4'(1'H)-one (Int 30a)

To a solution of 9-methylene-9H-fluorene (Int A14, 500 mg, 2.81 mmol) in MeCN (1.0 mL) and water (14.0 mL) were added 4-(tert-butyl)benzene-1,2-diol (46.6 mg, 0.281 mmol), 2-thioxodihydropyrimidine-4,6(1H,5H)-dione (607 mg, 4.21 mmol) and formaldehyde (0.427 mL, 5.61 mmol, 37% in water) at 30° C. under $N_2$ atmosphere. The mixture was stirred at 30° C. for 15 h. The mixture was extracted with DCM/MeOH (10:1) (3×200 mL), dried over $Na_2SO_4$, filtered and the solvent was evaporated under reduced pressure to give crude 2'-thioxo-2',3',5',6'-tetrahydrospiro[fluorene-9,7'-pyrano[2,3-d]pyrimidin]-4'(1'H)-one (Int 30a). MS (ESI): m/z $(M+H)^+$335.

Step B: 2'-(methylthio)-5',6'-dihydrospiro[fluorene-9,7'-pyrano[2,3-d]pyrimidin]-4'(3'H)-one (Int 30b)

To a solution of 2'-thioxo-2',3',5',6'-tetrahydrospiro[fluorene-9,7'-pyrano[2,3-d]pyrimidin]-4'(1'H)-one (Int 30a) (1.0 g, 2.034 mmol) in MeCN (10 mL) was added $K_2CO_3$ (0.422 g, 3.05 mmol) at 30° C. under $N_2$ atmosphere. The mixture was stirred at 30° C. for 1 h. Then iodomethane (0.095 mL, 1.525 mmol) was added and the mixture was stirred at 30° C. for 3 h. The mixture was diluted with water (20 mL), extracted with DCM/MeOH (10:1) (3×50 mL), dried over $Na_2SO_4$, filtered and the solvent was evaporated under reduced pressure to give crude 2'-(methylthio)-5',6'-dihydrospiro[fluorene-9,7'-pyrano[2,3-d]pyrimidin]-4'(3'H)-one (Int 30b) MS (ESI): m/z (M+H)+349.

Step C: benzyl (S)-2-(cyanomethyl)-4-(2'-(methylthio)-5',6'-dihydrospiro[fluorene-9,7'-pyrano[2,3-d]pyrimidin]-4'-yl)piperazine-1-carboxylate (Int 30c)

To a solution of 2'-(methylthio)-5',6'-dihydrospiro[fluorene-9,7'-pyrano[2,3-d]pyrimidin]-4'(3'H)-one (Int 30b) (100 mg, 0.287 mmol) in MeCN (2.0 mL) were added DBU (0.130 mL, 0.861 mmol), BOP (165 mg, 0.373 mmol) and (S)-benzyl 2-(cyanomethyl)piperazine-1-carboxylate (149 mg, 0.574 mmol) at 30° C. under $N_2$ atmosphere, and the mixture was stirred at 80° C. for 15 h. The mixture was cooled, quenched with water (5 mL), and extracted with EtOAc (3×5 mL). The combined organic layer was washed with brine (2×10 mL), dried over $Na_2SO_4$, the solvent was evaporated under reduced pressure to give crude product, which was purified by flash silica gel chromatography with an eluent of 0~30% ethyl acetate/petroleum ether gradient to give benzyl (S)-2-(cyanomethyl)-4-(2'-(methylthio)-5',6'-dihydrospiro[fluorene-9,7'-pyrano[2,3-d]pyrimidin]-4'-yl)piperazine-1-carboxylate (Int 30c). MS (ESI): m/z $(M+H)^+$590.

Step D: benzyl (2S)-2-(cyanomethyl)-4-(2'-(methylsulfinyl)-5',6'-dihydrospiro[fluorene-9,7'-pyrano[2,3-d]pyrimidin]-4'-yl)piperazine-1-carboxylate or benzyl (S)-2-(cyanomethyl)-4-(2'-(methylsulfonyl)-5',6'-dihydrospiro[fluorene-9,7'-pyrano[2,3-d]pyrimidin]-4'-yl)piperazine-1-carboxylate (Int 30d)

To a solution of benzyl (S)-2-(cyanomethyl)-4-(2'-(methylthio)-5',6'-dihydrospiro[fluorene-9,7'-pyrano[2,3-d]pyrimidin]-4'-yl)piperazine-1-carboxylate (Int 30c) (102.6 mg, 0.174 mmol) in DCM (2.0 mL) was added m-CPBA (60.0 mg, 0.348 mmol) at 0° C., and the mixture was stirred at 0° C. for 2 h. The mixture was evaporated under reduced pressure to give the crude product, which was purified by preparative TLC (petroleum ether: ethyl acetate 1:1) to give benzyl (2S)-2-(cyanomethyl)-4-(2'-(methylsulfinyl)-5',6'-dihydrospiro[fluorene-9,7'-pyrano[2,3-d]pyrimidin]-4'-yl)piperazine-1-carboxylate and benzyl (S)-2-(cyanomethyl)-4-(2'-(methylsulfonyl)-5',6'-dihydrospiro[fluorene-9,7'-pyrano[2,3-d]pyrimidin]-4'-yl)piperazine-1-carboxylate (Int 30d) MS (ESI): m/z $(M+H)^+$606; 622.

Step E: benzyl (S)-2-(cyanomethyl)-4-(2'-(((S)-1-methylpyrrolidin-2-yl methoxy)-5',6'-dihydrospiro[fluorene-9,7'-pyrano[2,3-d]pyrimidin]-4'-yl)piperazine-1-carboxylate (Int 30e)

To a solution of (S)-(1-methylpyrrolidin-2-yl)methanol (66.2 mg, 0.575 mmol) in THF (1.0 mL) was added sodium 2-methylpropan-2-olate (0.239 mL, 0.479 mmol) (2.0 M in THF) at 0° C. under $N_2$ atmosphere. After being stirred for 10 min, benzyl (2S)-2-(cyanomethyl)-4-(2'-(methylsulfinyl)-5',6'-dihydrospiro[fluorene-9,7'-pyrano[2,3-d]pyrimidin]-4'-yl)piperazine-1-carboxylate (Int 30d) (116 mg, 0.192 mmol) (the mixture of sulphone and sulfoxide) in THF (1.0 mL) was added to the above mixture, and the mixture was stirred at 0° C. for 1 h. The mixture was evaporated under reduced pressure to give the crude product, which was purified by preparative TLC (DCM:MeOH=10:1) to give benzyl (S)-2-(cyanomethyl)-4-(2'-(((S)-1-methylpyrrolidin-2-yl)methoxy)-5',6'-dihydrospiro[fluorene-9,7'-pyrano[2,3-d]pyrimidin]-4'-yl)piperazine-1-carboxylate (Int 30e). MS (ESI): m/z $(M+H)^+$657.

Step F: 2-((S)-4-(2'-(((S)-1-methylpyrrolidin-2-yl)methoxy)-5',6'-dihydrospiro[fluorene-9,7'-pyrano[2,3-d]pyrimidin]-4'-yl)piperazin-2-yl)acetonitrile (Int 30f)

To a solution of benzyl (S)-2-(cyanomethyl)-4-(2'-(((S)-1-methylpyrrolidin-2-yl)methoxy)-5',6'-dihydrospiro[fluorene-9,7'-pyrano[2,3-d]pyrimidin]-4'-yl)piperazine-1-carboxylate (Int 30e) (45 mg, 0.070 mmol) in DCM (1.0 mL) were added triethylamine (0.019 mL, 0.139 mmol), triethylsilane (24.27 mg, 0.209 mmol) and palladium (II) chloride (1.234 mg, 6.96 μmol) at 25° C., and the mixture was stirred at 25° C. for 20 min. The mixture was quenched with MeOH (2.0 mL), filtered, and the filtrate was evaporated under reduced pressure to give crude product 2-((S)-4-(2'-(((S)-1-methylpyrrolidin-2-yl)methoxy)-5',6'-dihydrospiro[fluorene-9,7'-pyrano[2,3-d]pyrimidin]-4'-yl)piperazin-2-yl)acetonitrile (Int 30f) MS (ESI): m/z (M+H)+523.

Step G: 2-((S)-1-acryloyl-4-(2'-(((S)-1-methylpyrrolidin-2-yl)methoxy)-5',6'-dihydrospiro[fluorene-9,7'-pyrano[2,3-d]pyrimidin]-4'-yl)piperazin-2-yl)acetonitrile (Int 30g)

To a solution of 2-((S)-4-(2'-(((S)-1-methylpyrrolidin-2-yl)methoxy)-5',6'-dihydrospiro[fluorene-9,7'-pyrano[2,3-d]pyrimidin]-4'-yl)piperazin-2-yl)acetonitrile (Int 30f) (30 mg, 0.057 mmol) in $CH_2Cl_2$ was added DIEA (30.1 μl, 0.172 mmol) at 25° C. Then the mixture was cooled to 0° C., and acryloyl chloride (5.20 mg, 0.057 mmol) was added, and the mixture was stirred at 0° C. for 5 min. The mixture was evaporated under reduced pressure to give the crude product, which was purified by reverse preparative HPLC (Column: Agela DuraShell C18 150 mm×25 mm, 5 um; Condition: water (0.05% $NH_3H_2O$+10 mM $NH_4HCO_3$)-ACN; followed by preparative TLC ($SiO_2$, DCM:MeOH=10:1) to give 2-((S)-1-acryloyl-4-(2'-(((S)-1-methylpyrrolidin-2-yl)methoxy)-5',6'-dihydrospiro[fluorene-9,7'-pyrano[2,3-d]pyrimidin]-4'-yl)piperazin-2-yl)acetonitrile as an oil. MS (ESI): m/z (M+H)+577. $^1H$ NMR (400 MHz, METHANOL-$d_4$) δ: 7.76 (d, J=7.4 Hz, 2H), 7.50-7.41 (m, 4H), 7.34-7.27 (m, 2H), 6.81 (br s, 1H), 6.29 (br d, J=16.8 Hz, 1H), 5.84 (br d, J=10.2 Hz, 1H), 5.08 (br s, 1H), 4.59 (br s, 1H), 4.33 (br d, J=5.9 Hz, 2H), 4.25-4.19 (m, 1H), 4.14 (br d, J=12.5 Hz, 1H), 3.69 (br s, 1H), 3.40 (br s, 1H), 3.23 (br s, 1H), 3.15-2.97 (m, 4H), 2.84-2.79 (m, 1H), 2.52 (s, 3H), 2.48-2.35 (m, 2H), 2.27 (br dd, J=6.7, 14.1 Hz, 1H), 2.18-2.03 (m, 2H), 1.87-1.79 (m, 2H), 1.70 (br dd, J=7.2, 12.3 Hz, 1H).

Biological Assays:

Procedure for SOS-Catalyzed Nucleotide Exchange Assay

The SOS-catalyzed nucleotide exchange assay utilizes a preformed complex of recombinant biotinylated KRAS protein containing G12C/C51S/C80L/C118S mutations (183 amino acids; biotin on K10; leader sequence which is an AviTag; referred to as SEQ ID NO: 1 or "Biotinylated KRAS G12C protein" hereafter), Bodipy-GDP, and Terbium-streptavidin. Compounds are added to this complex and then after 60 minutes incubation time, the mixture is treated with recombinant SOS protein and unlabeled GTP. Small molecule inhibitors stabilize the Bodipy-GDP complex whereas the untreated protein rapidly exchanges Bodipy-GDP for unlabeled GTP resulting in reduced TR-FRET signal.

Biotinylated KRAS G12C protein (SEQ ID NO: 1) is diluted to 2 μM in an EDTA buffer (20 mM HEPES, 150 mM sodium chloride, 10 mM EDTA, and 0.01% Tween) and incubated at room temperature for one hour. This mixture is then further diluted to 90 nM in an assay buffer (20 mM HEPES, 150 mM sodium chloride, 10 mM magnesium chloride, and 0.005% Tween) containing 15 nM of Terbium-Streptavidin (Invitrogen, catalog #PV3577) and 900 nM of Bodipy-GDP and incubated at room temperature for six hours. This solution is referred to as Biotinylated KRAS G12C mixture.

Each test compound (10 mM stock in DMSO) is diluted in DMSO to make a 10-point, 3-fold dilution series in a 384-well low dead volume microplate (Labcyte, catalog #LP-0200). Once titrations are made, 10 nL of the diluted compounds is acoustically dispensed into a 384-well plate (Corning, catalog #3820) using an Echo 550 (Labcyte).

Each well of the plate receives 3 μL Biotinylated KRAS G12C mixture that had been incubating for six hours and 3 μL of assay buffer using a BioRAPTR (Beckman Coulter) and is incubated at room temperature for 60 minutes. Each well then receives 3 μL of 240 nM recombinant human SOS protein and 9 mM GTP (Sigma, G8877) in assay buffer and is incubated at room temperature for 60 minutes.

The time-resolved fluorescence resonance energy transfer signal of the plate is measured on an Envision (PerkinElmer) plate reader: Excitation filter=340 nm; emission1=495 nm; emission2=520 nm; dichroic mirror=D400/D505; delay time=100 μs. The signal of each well is determined as the ratio of the emission at 520 nm to that at 495 nm. Percent effect of each well is determined after normalization to control wells containing DMSO (no effect) or a saturating concentration of inhibitor (max effect). The apparent effect as a function of compound concentration is fit to a four parameter logistic equation.

Procedure for Cellular Phospho-ERK Assay

NCI-H358 cells (ATCC® CRL-5807™) were cultured in T150 flask in growth medium (RPMI medium 1640-(ThermoFisher Scientific 61870) containing 10% fetal bovine serum (ThermoFisher Scientific 10091148)). The cells were harvested in growth medium after TrypLE (ThermoFisher scientific 12604021) digestion and were seeded in 384-well collagen coated cell culture plate (Corning 356702) at a density of 15,000 cells/well, and incubated at 37° C., 5% $CO_2$ overnight. The compound dose-response titrations were prepared and appropriate amounts of compounds were dispensed in a 384-well intermediate plate using an Echo 550 liquid handler. RPMI medium 1640-GlutaMAX™-I were added to the intermediate plate and transferred to 384-well cell culture plate, which was incubated at 37° C., 5% $CO_2$ for 2 hours. After removal of medium from the plate, cells were lysed in lysis buffer from SureFire® Ultra™ Multiplex p-Erk and total Erk assay kit (PerkinElmer MPSU-PTERK) containing Halt™ Protease and Phosphotase inhibitor cocktail (ThermoFisher Scientific 78446) at room temperature with constant shaking at 300 rpm for 30 minutes. The cell lysates were then transferred to OptiPlate-384 plate (PerkinElmer 6005620) and the phosphorylation of Erk and total Erk levels were detected by Alpha SureFire Ultra Multiplex p-Erk kit PerkinElmer MPSU-PTERK) following the manufacturer's protocol. Assay plates were read on an EnVision Multimode Plate Reader (PerkinElmer), and the ratio of p-Erk vs total Erk in each well was used as the final readout. Dose response curves were analyzed using a 4-parameter logistic model to calculate $IC_{50}$ values using spotfire software.

TABLE 1

In vitro apparent potency ($IC_{50}$) in the SOS-catalyzed nucleotide exchange assay with a preincubation time of 60 minutes prior to addition of SOS. In vitro potency in the cellular phospho-ERK assay after 2 hour incubation.

| Compound | $IC_{50}$ (nM) at 60 min (SOS) | $IC_{50}$ (nM) pERK (Cell) |
|---|---|---|
| 1a | 6.375 | 494.9 |
| 1b | 54.92 | 2858 |
| 2a | 13.67 | 154.1 |
| 2b | 14.72 | 267.9 |
| 3a | 14.51 | 505.9 |
| 3b | 51.02 | 1125 |
| 4a | 14.95 | 310.9 |
| 4b | 164.1 | 2504 |
| 5a | 18.71 | 1252 |
| 5b | 274.5 | 5979 |
| 6a | 180.9 | 3102 |
| 6b | 413.2 | 4370 |
| 7a | 77.32 | 1619 |
| 7b | 118.7 | 2150 |
| 8 | 990.4 | 23390 |
| 9a | 40.5 | 1935 |
| 9b | 34.2 | 1171 |
| 9c | 109.8 | 1839 |
| 9d | 149.2 | 2411 |
| 10a | 145.1 | 6635 |
| 10b | 50 | 4531 |
| 11a | 46.7 | 1801 |
| 11b | 660.9 | 28550 |
| 12a | 99.7 | 1327 |
| 12b | 728 | 5623 |
| 13a | 575.9 | 4980 |
| 14a | 2081 | 4205 |
| 15a | 43.4 | 637.5 |
| 15b | 83.95 | 1811 |
| 16a | 18.89 | 246.4 |
| 16b | 109 | 1651 |
| 17a | 822.8 | 6677 |
| 18b | 267.8 | 1523 |
| 19a | 8471 | 30000 |
| 20a | 41.81 | 1466 |
| 20b | 80.39 | 2758 |
| 21a | 5337 | 10160 |
| 22a | 6319 | 24590 |
| 23a | 5072 | 26490 |
| 24a | 2392 | 12880 |
| 25a | 14.2 | 1101 |
| 25b | 11.6 | 2743 |
| 25c | 253 | 10960 |
| 25d | 113 | 8134 |
| 26a | 2871 | 19230 |
| 26b | 159.3 | 9619 |
| 26c | 658.6 | 18730 |
| 26d | 129.3 | 9746 |
| 27a | 1076 | 30000 |
| 27b | 4490 | 28620 |
| 28a | 7844 | >30000 |
| 28b | 2330 | 29350 |
| 29 | 5007 | 19180 |
| 30 | 68.6 | 1291 |

Protein Sequence
Biotinylated KRAS G12C protein (SEQ ID NO: 1)
GLNDIFEAQKIEWHETEYKLVVVGACGVGKSALTIQLIQNHFVDEYDPT

IEDSYRKQVVIDGETSLLDILDTAGQEEYSAMRDQYMRTGEGFLLVFAI

NNTKSFEDIHHYREQIKRVKDSEDVPMVLVGNKSDLPSRTVDTKQAQDL

ARSYGIPFIETSAKTRQGVDDAFYTLVREIRKHKEK

---

We claim:

1. A compound of the Formula (I)

(I)

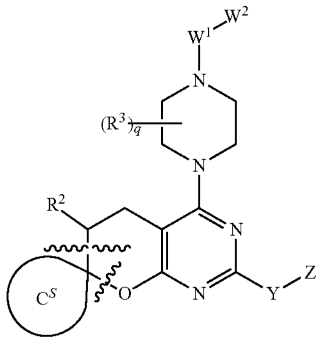

wherein:

the substructure

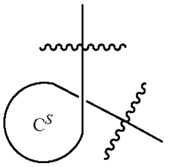

is

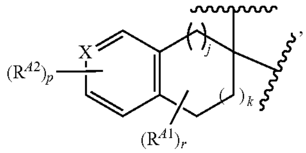

,

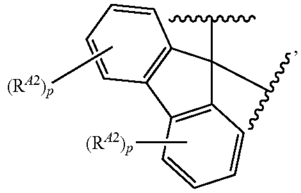

, or

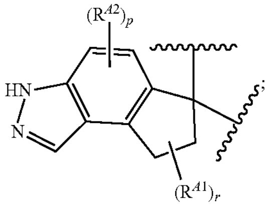

;

X is C(H) or N;

$R^{A1}$ is fluoro, $C_1$-$C_3$ alkyl, or $C_1$-$C_3$ fluoroalkyl;

$R^{A2}$ is halo, $C_1$-$C_3$ alkyl, $C_1$-$C_3$ fluoroalkyl, $C_1$-$C_3$ alkoxy, hydroxy or cyano;

the subscript j is 0 or 1;

the subscript k is 0, 1 or 2;

the subscript r is 0, 1, 2, or 3;

the subscript p is 0, 1, 2, 3, or 4;

$R^2$ is H, $C_1$-$C_3$ alkyl, or fluoro;

each $R^3$ is independently:

(a) $C_1$-$C_4$ alkyl, $C_1$-$C_4$ cyanoalkyl, $C_1$-$C_4$ fluoroalkyl, $C_1$-$C_4$ hydroxyalkyl, $C_1$-$C_4$ alkylphenyl, oxo, or carboxy;

(b) or, alternatively, two $R^3$ substituents, together with the carbon atoms to which they are attached, can form a 3- to 6-membered bicyclo- or spirocyclic ring system with the illustrated piperazine ring;

the subscript q is 0, 1, 2, or 3;

$W^1$ is —C(O)— or —$S(O)_2$—;

$W^2$ is a group of the formula:

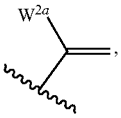

,

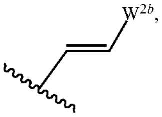

,

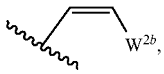

,

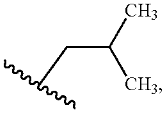

, or

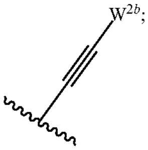

;

wherein $W^{2a}$ is H, $CH_3$, F, cyano, $CH_2OH$, $CH_2CH_2OH$, or $CH_2Br$;

$W^{2b}$ is $CH_3$;

Y is —$O(C(R^y)_2)_m$—, —C(O)—N(H)—$(C(R^y)_2)_m$—, or absent;

each $R^y$ is independently H or $C_1$-$C_3$ alkyl, or alternatively two $R^y$ together with the carbon atom to which they are attached form a cyclopropyl, cyclobutyl, cyclopentyl or cyclohexyl ring;

the subscript m is 1, 2, or 3;

Z is (a)

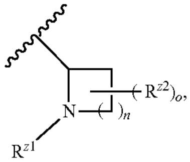

, wherein $R^{z1}$ is $C_1$-$C_3$ alkyl;

each $R^{z2}$ is independently fluoro or $C_1$-$C_3$ alkyl;

the subscript n is 1, 2, or 3;

the subscript o is 0, 1, or 2;

(b) —$N(R^{z3})_2$; or (c) —$C(O)N(R^{z3})_2$, wherein each $R^{z3}$ is independently H or $C_1$-$C_3$ alkyl; or alternatively, two $R^{z3}$, together with the nitrogen atom to which they are attached, form a ring $C^z$, wherein ring $C^z$ is an aziridinyl, azetidinyl, pyrrolidinyl, piperidinyl, or azepinyl ring;

wherein ring $C^z$ is unsubstituted or substituted by 1 to 3 fluoro, $C_1$-$C_3$ alkyl, amino, —N(H)($C_1$-$C_3$ alkyl), or —$N(C_1$-$C_3$ alkyl$)_2$;

or a pharmaceutically salt thereof.

2. The compound of claim 1 or the pharmaceutically acceptable salt thereof, wherein the group —$W^1$—$W^2$ is —C(O)—C(H)═$CH_2$.

3. The compound of claim 1, or the pharmaceutically acceptable salt thereof, wherein the subscript q is 0 or 1 and $R^3$ is methyl or $—CH_2CN$.

4. The compound of claim 1 or the pharmaceutically acceptable salt thereof, wherein the substructure

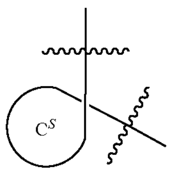

is

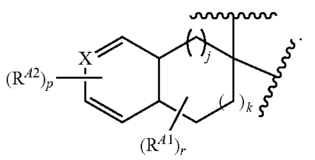

5. The compound of claim 4 or the pharmaceutically acceptable salt thereof, wherein the subscript j is 0 and the subscript k is 2.

6. The compound of claim 4 or the pharmaceutically acceptable salt thereof, wherein the subscript j is 0 and the subscript k is 1.

7. The compound of claim 4 or the pharmaceutically acceptable salt thereof, wherein X is C(H).

8. The compound of claim 1 or the pharmaceutically acceptable salt thereof, wherein the substructure

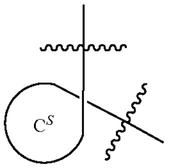

is

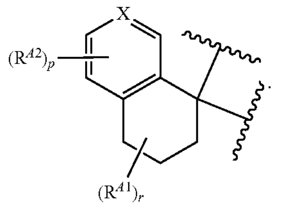

9. The compound of claim 1 or the pharmaceutically acceptable salt thereof, wherein $R^2$ is H.

10. The compound of claim 1 or the pharmaceutically acceptable salt thereof, wherein Y is $—O(C(R^y)_2)_m—$ and the subscript m is 1 or 2.

11. The compound of claim 10 or the pharmaceutically acceptable salt thereof,
wherein Z is

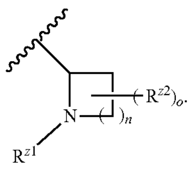

12. The compound of claim 11 or the pharmaceutically acceptable salt thereof, wherein the subscript n is 2.

13. The compound of claim 1 or the pharmaceutically acceptable salt thereof, wherein the group —Y—Z is

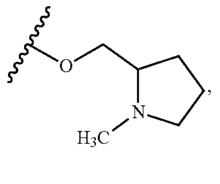

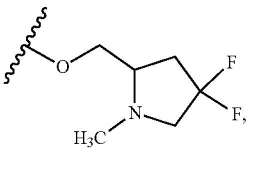

-continued

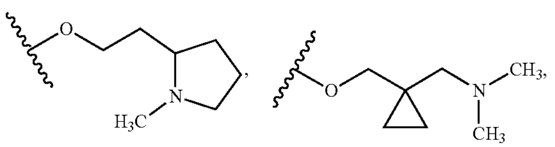

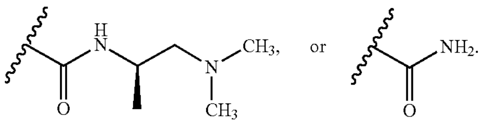

14. A compound selected from the group consisting of:

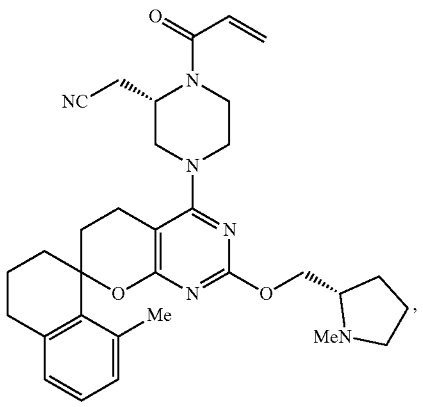

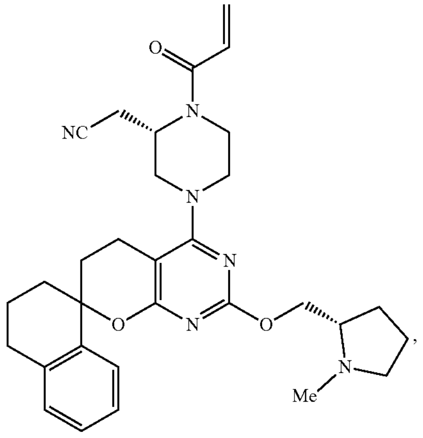

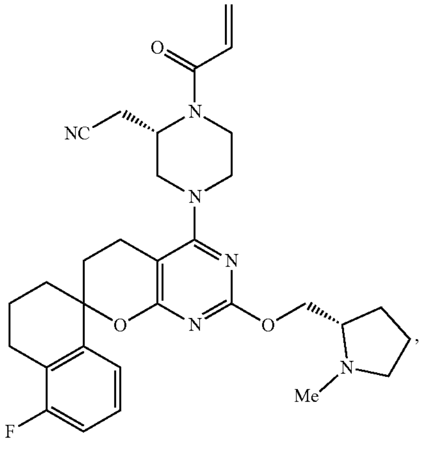

-continued
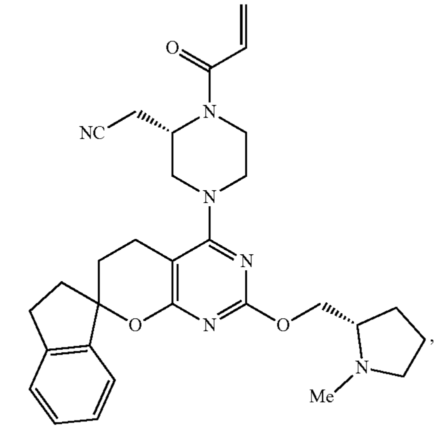
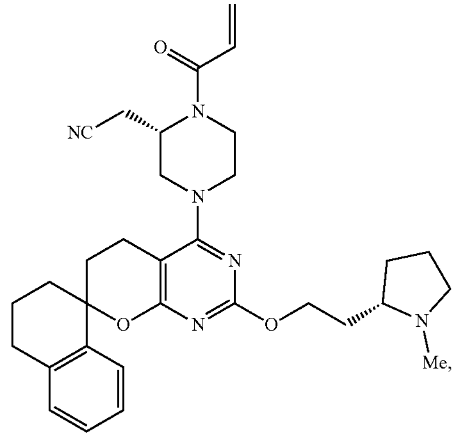
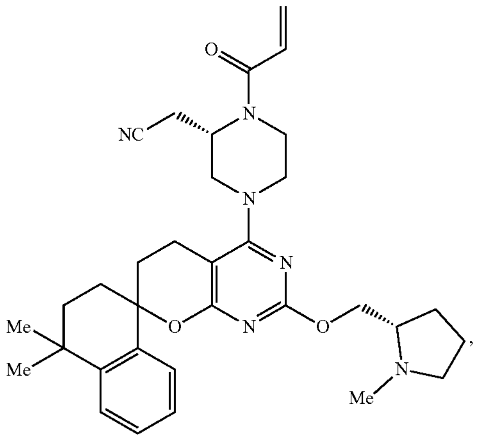
-continued
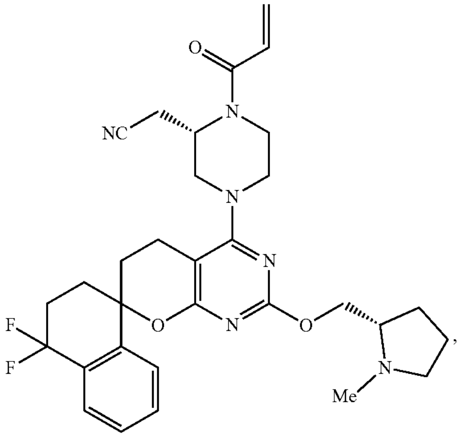
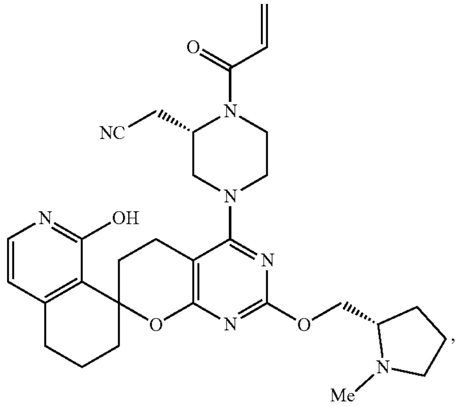
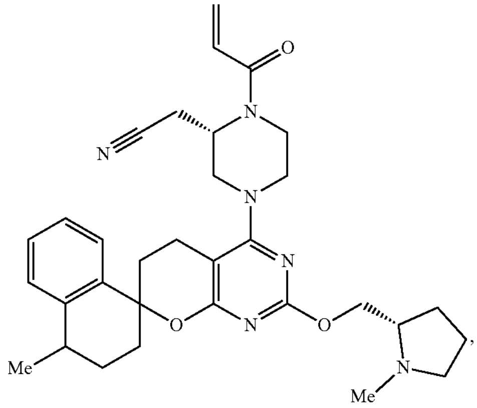
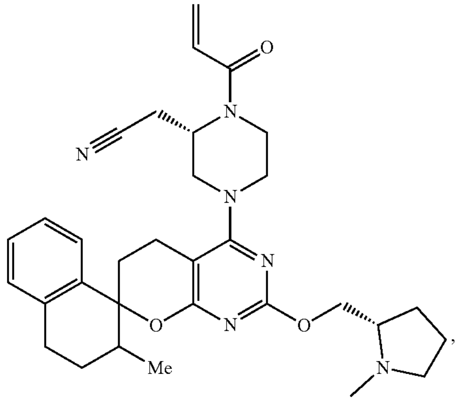

-continued
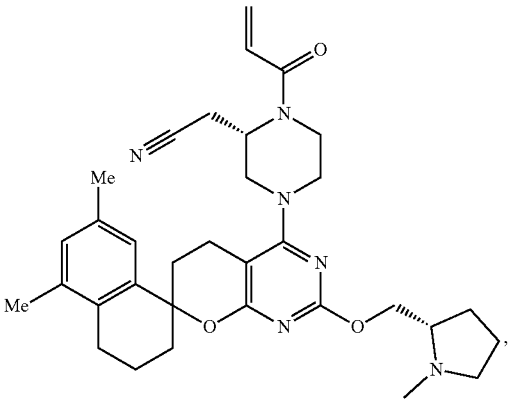
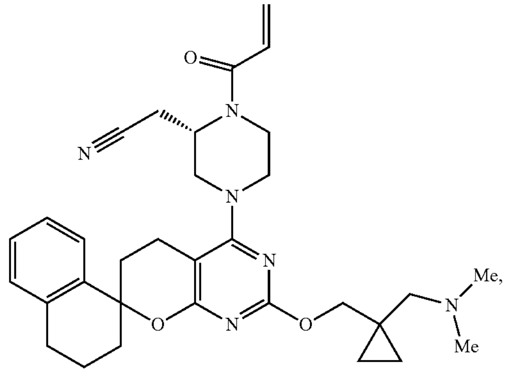
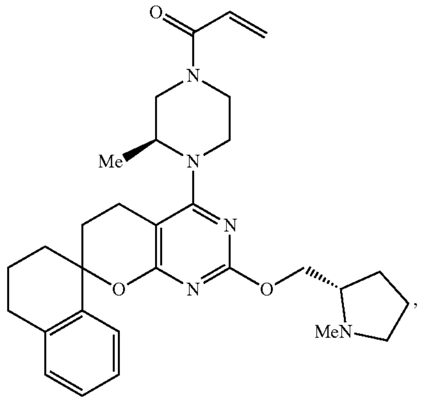
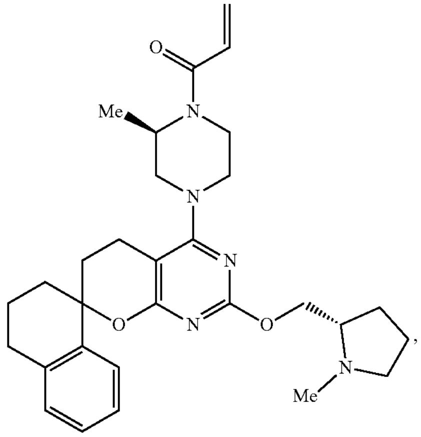
-continued
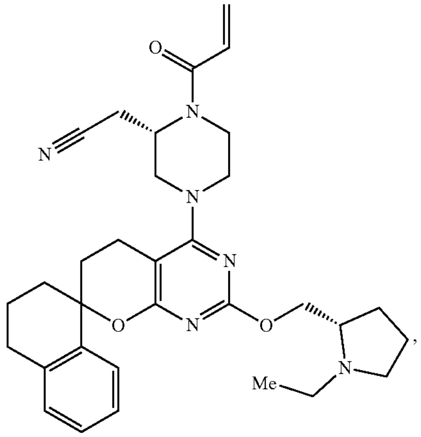
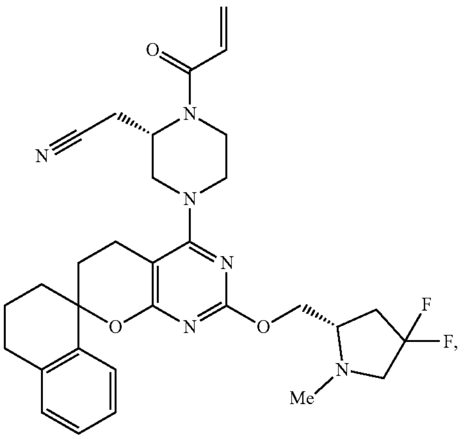
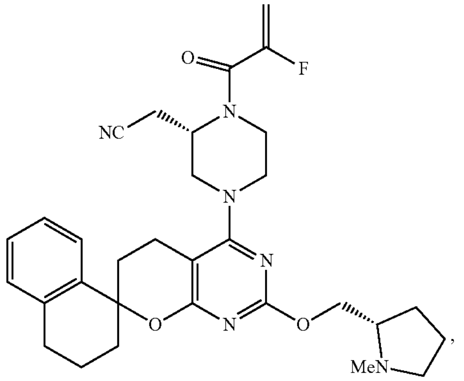
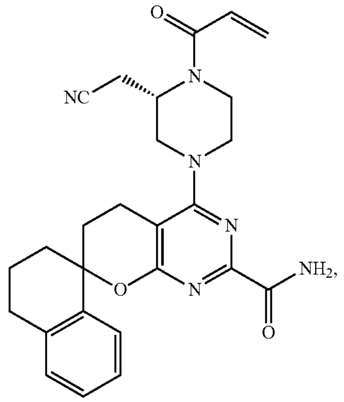

-continued
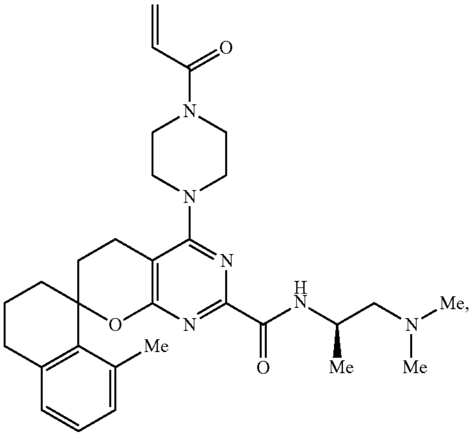
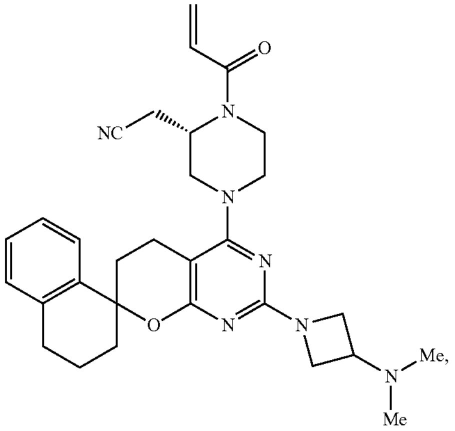
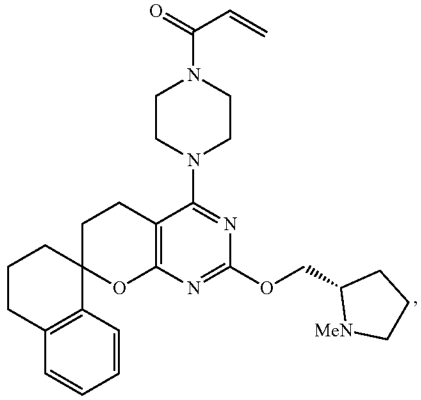
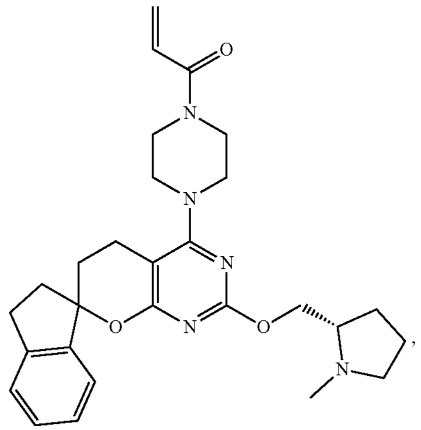
-continued
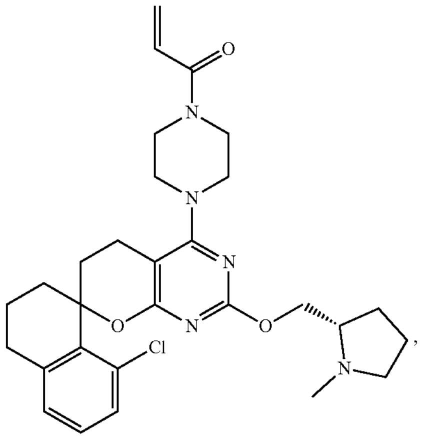
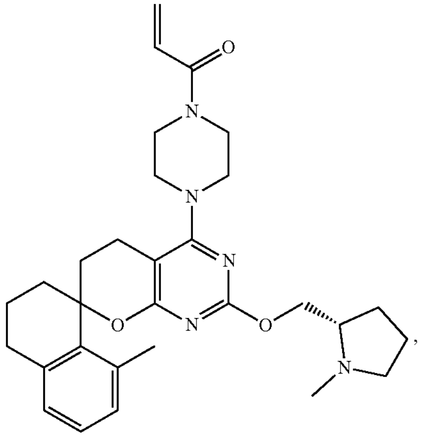
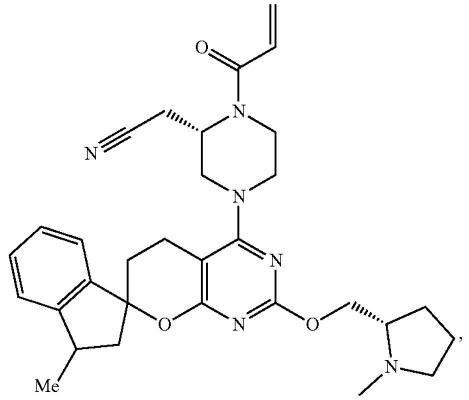
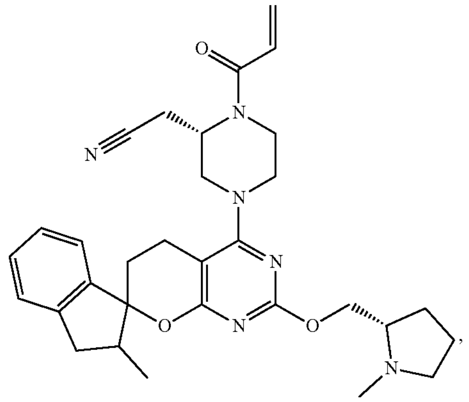

-continued

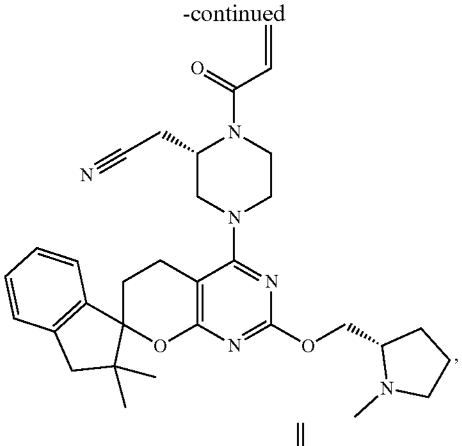

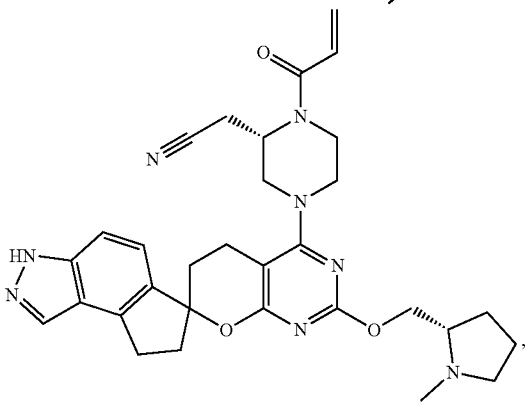

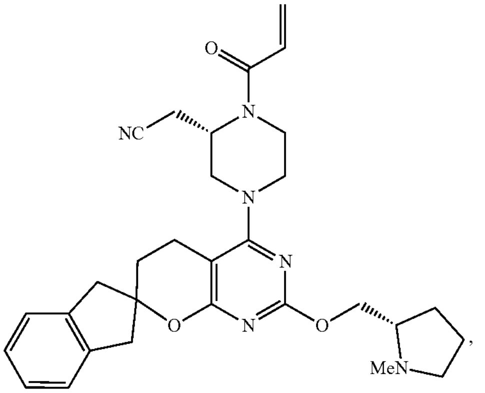

or

-continued

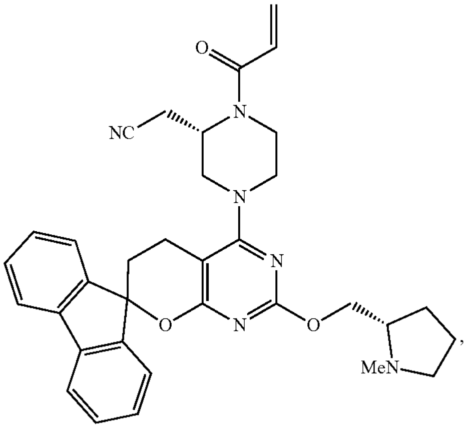 [SMILES: C=CC(=O)N1CCN(c2nc(OC[C@@H]3CCCN3C)nc3c2CCC2(O3)c3ccccc3-c3ccccc32)C[C@@H]1CC#N]

or the pharmaceutically acceptable salt thereof.

15. A pharmaceutical composition comprising the compound of claim 1 or the pharmaceutically acceptable salt thereof, and a pharmaceutically acceptable carrier.

16. A method of inhibiting KRAS G12C protein comprising contacting KRAS G12C protein with the compound of claim 1, or the pharmaceutically acceptable salt thereof, to inhibit the activity of the KRAS G12C protein.

17. A method of treating cancer comprising administering a therapeutically effective amount of the compound of claim 1, or the pharmaceutically acceptable salt thereof, to a subject in need of such treatment.

18. The method of claim 17, further comprising administering an additional active agent to the subject, wherein the additional active agent is an anti-cancer agent.

19. The pharmaceutical composition of claim 15, further comprising an additional active agent, wherein the additional active agent is an anti-cancer agent.

* * * * *

SEQUENCE LISTING

```
<160> NUMBER OF SEQ ID NOS: 1

<210> SEQ ID NO 1
<211> LENGTH: 183
<212> TYPE: PRT
<213> ORGANISM: Artificial
<220> FEATURE:
<223> OTHER INFORMATION: Synthetic Protein
<220> FEATURE:
<221> NAME/KEY: biotin
<222> LOCATION: (10)..(10)

<400> SEQUENCE: 1

Gly Leu Asn Asp Ile Phe Glu Ala Gln Lys Ile Glu Trp His Glu Thr
1               5                   10                  15

Glu Tyr Lys Leu Val Val Val Gly Ala Cys Gly Val Gly Lys Ser Ala
            20                  25                  30

Leu Thr Ile Gln Leu Ile Gln Asn His Phe Val Asp Glu Tyr Asp Pro
        35                  40                  45

Thr Ile Glu Asp Ser Tyr Arg Lys Gln Val Val Ile Asp Gly Glu Thr
    50                  55                  60

Ser Leu Leu Asp Ile Leu Asp Thr Ala Gly Gln Glu Glu Tyr Ser Ala
65                  70                  75                  80

Met Arg Asp Gln Tyr Met Arg Thr Gly Glu Gly Phe Leu Leu Val Phe
                85                  90                  95

Ala Ile Asn Asn Thr Lys Ser Phe Glu Asp Ile His His Tyr Arg Glu
            100                 105                 110

Gln Ile Lys Arg Val Lys Asp Ser Glu Asp Val Pro Met Val Leu Val
        115                 120                 125

Gly Asn Lys Ser Asp Leu Pro Ser Arg Thr Val Asp Thr Lys Gln Ala
    130                 135                 140

Gln Asp Leu Ala Arg Ser Tyr Gly Ile Pro Phe Ile Glu Thr Ser Ala
145                 150                 155                 160

Lys Thr Arg Gln Gly Val Asp Asp Ala Phe Tyr Thr Leu Val Arg Glu
                165                 170                 175

Ile Arg Lys His Lys Glu Lys
            180
```